United States Patent
Ichim et al.

(10) Patent No.: US 9,091,696 B2
(45) Date of Patent: Jul. 28, 2015

(54) MODULATION OF NR2F6 AND METHODS AND USES THEREOF

(71) Applicants: Christine Victoria Ichim, Kitchener (CA); Richard Alexander Wells, Toronto (CA)

(72) Inventors: Christine Victoria Ichim, Kitchener (CA); Richard Alexander Wells, Toronto (CA)

(73) Assignee: Regen Biopharma, Inc., La Mesa, CA (US)

( * ) Notice: Subject to any disclaimer, the term of this patent is extended or adjusted under 35 U.S.C. 154(b) by 13 days.

(21) Appl. No.: 13/652,395

(22) Filed: Oct. 15, 2012

(65) Prior Publication Data

US 2013/0225425 A1    Aug. 29, 2013

Related U.S. Application Data

(63) Continuation of application No. 12/619,290, filed on Nov. 16, 2009, now abandoned.

(60) Provisional application No. 61/114,764, filed on Nov. 14, 2008.

(51) Int. Cl.
| | |
|---|---|
| *A61K 38/00* | (2006.01) |
| *C12N 15/63* | (2006.01) |
| *G01N 33/68* | (2006.01) |
| *A61K 31/00* | (2006.01) |
| *A61K 31/7088* | (2006.01) |
| *G01N 33/574* | (2006.01) |

(52) U.S. Cl.
CPC ............ *G01N 33/6872* (2013.01); *A61K 31/00* (2013.01); *A61K 31/7088* (2013.01); *G01N 33/57426* (2013.01); *G01N 33/6875* (2013.01); *G01N 2333/70567* (2013.01); *G01N 2800/22* (2013.01)

(58) Field of Classification Search
None
See application file for complete search history.

(56) References Cited

PUBLICATIONS

Bandukwala Immunity, 2008, v.29, pp. 167-168.*
Feldman et al., Transplant. Proc. 1998, 30, 4126-4127.*
Mestas et al J. of Immunology, 2004, 172, pp. 2731-238.*

* cited by examiner

*Primary Examiner* — Michail Belyavskyi
(74) *Attorney, Agent, or Firm* — Marc Baumgartner; Baumgartner Patent Law

(57) ABSTRACT

The application provides methods of modulating NR2F6 in a cell or animal in need thereof by administering an effective amount of a NR2F6 modulator.

12 Claims, 72 Drawing Sheets

U937-GFP

U937-NR2F6

| CD49b⁻ LT HSC | GFP | NR2F6 | | CD34⁻ LT HSC | GFP | NR2F6 |
|---|---|---|---|---|---|---|
| Percent GFP+ KSL cells: | 9.2% | 53.4% | | Percent GFP+ KSL cells: | 4.1% | 11.7% |
| Percent total GFP+ BM cells | 0.24% | 0.73% | | Percent total GFP+ BM cells | 0.25% | 1.34% |

NR2F6

GFP

NR2F6

GFP

NR2F6

GFP

MODULATION OF NR2F6 AND METHODS AND USES THEREOF

RELATED APPLICATIONS

This application claims the benefit of U.S. non-provisional application Ser. No. 12/619,290, filed Nov. 16, 2009 which claims the benefit under 35 USC §119(e) of U.S. provisional application No. 61/114,764 filed Nov. 14, 2008, both of which are incorporated herein in their entireties.

FIELD

The present disclosure relates to methods and compositions for modulating NR2F6 for therapeutic applications. In particular, the disclosure relates to methods and compositions comprising modulators of NR2F6 for modulating stem cell growth, proliferation and differentiation and for treating associated conditions and diseases.

BACKGROUND

Primary cancer cells exhibit heterogeneity in clonogenicity, the capacity to proliferate and form colonies in vitro. The cancer stem cell (CSC) model accounts for this heterogeneity by proposing that each cancer consists of a small population of cells capable of unlimited growth and self-renewal, known as CSCs, and a much larger population of cells, descendants of the CSCs, that have lost self-renewal capacity and are undergoing terminal differentiation. Evidence supporting this model has been reported for several malignancies including acute myelogenous leukemia, brain cancer and breast cancer. The CSC model has important implications for cancer therapy; eradication of CSCs, the cells responsible for maintenance of the neoplasm, would be necessary and sufficient to achieve cure.

Myelodysplastic syndrome (MDS) is a clonal disorder of haematopoietic tissue, characterized by peripheral blood cytopenias, apoptosis of bone marrow haematopoietic progenitors, abnormal blood cell morphology (dysplasia) and a marked propensity to evolve into acute leukemia. The central paradox of MDS biology resides in the observation that the MDS clone, which is characterized by reduced numbers of mature progeny and by maturing progenitors that exhibit impaired clonogenicity and a high rate of apoptosis, nonetheless comes to dominate the bone marrow at the expense of residual normal haematopoiesis and thereby causes disease. The cancer stem cell model suggests a resolution to this paradox, namely that the MDS clone, despite the defects seen in its differentiating members, out-competes normal haematopoiesis because of a selective advantage at the stem cell level. It is hypothesized that this competitive advantage consists in an increased capacity of MDS stem cells for self-renewal.

The natural history of MDS is highly heterogenous, with some cases causing chronic cytopenias and others rapidly progressing to acute leukemia. Patients diagnosed with MDS have a life expectancy of 6 months to 5 years, and despite the recent development of some promising new therapies that offer hope for a small subset of patients with MDS, the mainstay of treatment for this disease remains supportive for palliative care with blood transfusion. Thus, most patients diagnosed with MDS face the prospect of a shortened life expectancy, impaired quality of life because of dependency on transfusions, and dread and uncertainty regarding the onset of acute leukemia.

Acute leukemia (AL) is an aggressive cancer of the blood forming cells in the bone marrow. It may arise secondary to preexisting hematopoietic conditions such as MDS, or de novo. Despite the many advances made in the understanding of leukemia biology over the past three decades, therapy for AML remains, in most cases, debilitating and ineffective. Further progress in improving the efficacy of anti-leukemia therapy hinges upon the identification of methods that allow for the targeting of the leukemia stem cell. Leukemia is a disease characterised by impairment of differentiation. Leukemia stem cells are the culprit of the disease. These rare cells (<1% of the population) are the only leukemia cells that are immortal. These cells are responsible for the initiation and maintenance of the leukemia. Eradication of the leukemia stem cell therefore, would be necessary and sufficient for cure. The rest of the leukemia cells in an AML patient are non-stem leukemia cells, these comprise the vast majority of the patient's leukemia cell burden. Non-stem leukemia cells are "benign" cells that either have a finite ability to divide or have lost the ability to divide altogether. Non-stem leukemia cells arise from the differentiation of leukemia stem cells. In contrast to current therapies that target both leukemia stem and non-stem cells, differentiation therapy aims at inhibiting the ability of leukemia stem cells to self-renew and inducing the differentiation of leukemia stem cells into non-stem leukemia cells. Differentiation therapy promises to be much more effective, selective and less toxic than chemotherapy.

NR2F6, known also as EAR-2, is an orphan nuclear receptor and a member of the chicken ovalbumin upstream promoter (COUP) family of nuclear receptors. The nuclear receptors (NRs) comprise a very large family of ligand activated transcription factors. Multiple lines of evidence suggest a role for NR signalling in the transcriptional regulation of haematopoiesis. Acute promyelocytic leukemia is invariably associated with gene fusions involving the retinoic acid receptor α (RARα) and one of five different partners, PML, PLZF, NPM, NuMA, and STAT5b. Patients with this disease respond to treatment with the RARα ligand, all trans retinoic acid (ATRA). Dominant negative mutants of RARα enhance mast cell development and reduce granulocyte and macrophage development in multipotential haematopoietic cell lines, and also block myeloid development in transduced murine bone marrow. Although targeted disruption of RARα in the mouse has little effect on haematopoiesis, in vitro studies revealed an increased proportion of morphologically immature granulocytes in RARα1/RARγ double mutants. In addition to this, in vitro studies suggest a role for the thyroid hormone receptor in erythropoiesis and for the PPARγ in monocyte/macrophage development. A role for the vitamin D receptor in myeloid differentiation is suggested by 1,25-dihydroxyvitamin D3-induced terminal differentiation and cell cycle arrest of a variety of leukaemic cell lines. Although little is known of the downstream genes regulated by NRs in haematopoiesis, evidence suggests that the cdk inhibitor p21 and the transcription factor C/EBPε may be targets of RARα in myelopoiesis.

NR2F6, known also as EAR-2, is an orphan nuclear receptor that was cloned in a search for homologues of the retroviral oncogene v-erbA using low stringency hybridization (see Miyajima, N., et al., (Identification of two novel members of erbA superfamily by molecular cloning: the gene products of the two are highly related to each other. Nucleic Acids Res, 16 (23): p. 11057-74. 1988)). EAR-2 is a member of the chicken ovalbumin upstream promoter (COUP) family of nuclear receptors. The COUPs function in vitro as transcriptional repressors, antagonizing the activation ability of a wide range of nuclear receptors that play prominent roles in differentiation. Accordingly, aberrant expression of COUP-TFI inhibits retinoid-induced epithelial and neuronal differentiation in vitro (Please see Kyakumoto, S., M. Ota, and N. Sato (Inhibition of retinoic acid-inducible transcription by COUP-TFI in human salivary gland adenocarcinoma cell line HSG. Biochem Cell Biol, 77 (6): p. 515-26. 1999), Neuman, K., et al., (Orphan receptor COUP-TF I antagonizes retinoic acid-induced neuronal differentiation. J Neurosci Res, 41 (1): p. 39-48. 1995) and Adam, F., et al., (COUP-TFI (chicken ovalbumin upstream promoter-transcription factor I) regulates cell migration and axogenesis in differentiating P19 embryonal carcinoma cells. Mol Endocrinol, 14 (12): p. 1918-33. 2000)). The roles of COUP-TFI and COUP-TFII in mammalian development have been studied by targeted deletion in the mouse. COUP-TFI deficient mice exhibit numerous defects in axonal development, including failure of development of the nucleus of the 9th cranial nerve. COUP-TFII deletion causes widespread defects in angiogenesis and cardiac development, leading to embryonic lethality in midgestation. Seven-up (svp), the *Drosophila* COUP family homologue, is also important in embryonic development; with null mutations of seven-up being embryonic lethal. svp is involved in decisions of cell fate determination during the development of the photoreceptors in the ommatidium of the eye and regulates proliferation during the development of the malpighian tubules by regulating the expression of cell cycle regulators.

In contrast to the related proteins COUP-TFI and COUP-TFII, the function of EAR-2 has not been well characterized. EAR-2 functions as a transcriptional repressor in vitro, inhibiting the transactivating ability of numerous genes including the thyroid hormone receptor (See Zhu, X. G. et al. (The orphan nuclear receptor Ear-2 is a negative coregulator for thyroid hormone nuclear receptor function. *Mol Cell Biol* 20, 2604-18. 2000)). Like many nuclear receptors, EAR-2 heterodimerizes with the retinoid X receptor-α (RXR-α), although the relevance of this interaction in EAR-2 function is unclear (See Ladias, (J. A. Convergence of multiple nuclear receptor signaling pathways onto the long terminal repeat of human immunodeficiency virus-1. *J Biol Chem* 269, 5944-51 1994)).

The role for EAR-2 in haematopoiesis has not been studied in vivo. A previous study has shown interaction of NR2F6 with the key haematopoietic transcription factor RUNX1 (also known as AML1) (See Ahn et al. (Negative regulation of granulocytic differentiation in the myeloid precursor cell line 32Dcl3 by ear-2, a mammalian homolog of *Drosophila* seven-up, and a chimeric leukemogenic gene, AML1/ETO. *Proc Natl Acad Sci USA* 95, 1812-7. 1998)). Targeted deletion of RUNX1, a component of the core binding factor complex, results in abrogation of definitive haematopoiesis and embryonic lethality and RUNX1 rearrangements result from several commonly seen chromosome translocations in acute leukemia. EAR-2 interacts physically with RUNX1 and represses its transcriptional activating ability in the murine myeloblast cell line 32Dcl3. The effect of NR2F6 in primary mouse or human bone marrow, let alone in vivo is unclear. EAR-2 is down regulated in 32Dcl3 cells induced to mature with G-CSF, and forced expression of the EAR-2 protein blocks 32Dcl3 differentiation.

The function of NR2F6 has not been well characterized. NR2F6 functions as a transcriptional repressor in vitro, inhibiting the transactivating ability of numerous proteins including the thyroid hormone receptor. Like many nuclear receptors, NR2F6 heterodimerizes with the retinoid X receptor-α (RXR-α), although the relevance of this interaction in NR2F6 function is unclear (See Ladias, J. A. (Convergence of multiple nuclear receptor signaling pathways onto the long terminal repeat of human immunodeficiency virus-1. J Biol Chem 269, 5944-51 1994)). A recent report describes the initial characterization of an NR2F6 deficient mouse generated by targeted disruption of the NR2F6 locus (See Warnecke, M et al. (Abnormal development of the locus coeruleus in Ear2(Nr2f6)-deficient mice impairs the functionality of the forebrain clock and affects nociception. Genes Dev 19, 614-25 2005)). NR2F6 deficient mice are viable and fertile, but show agenesis of the locus coeruleus, a midbrain nucleus that regulates circadian behaviour and nociception. In situ mRNA hybridization in NR2F6–/– animals places NR2F6 downstream of Mash1 and upstream of Phox2a and Phox2b in the specification of the locus coeruleus. Although NR2F6 expression is seen outside the central nervous system, this report contains no description of any phenotypic analysis outside the nervous system.

SUMMARY

The present inventors have found that the orphan nuclear receptor NR2F6 is a critical regulator of blood stem cell self-renewal and differentiation, and the maturation of healthy progenitor cells. NR2F6 regulates self-renewal, differentiation and maturation in states of pathology. This makes the modulation of NR2F6 an ideal target for influencing the function of leukemia stem and progenitor cells and myelodsplastic syndrome stem and progenitor cells.

Accordingly, in one aspect, the present disclosure provides a method of modulating stem cell growth, proliferation and/or differentiation comprising administering an effective amount of a NR2F6 inhibitor to a cell or animal in need thereof.

In one embodiment, the NR2F6 modulator is a NR2F6 inhibitor. Accordingly, in an embodiment, the present disclosure provides a method of inhibiting self-renewal of stem cells and/or inducing terminal differentiation of stem cells comprising administering an effective amount of a NR2F6 inhibitor to a cell or animal in need thereof.

In one embodiment, the inhibitor is an antisense nucleic acid sequence of the gene encoding NR2F6 as shown in SEQ ID NO: 1 or 4 or variants thereof. In another embodiment, the inhibitor is a blocking antibody that binds the NR2F6 amino acid sequence as shown in SEQ ID NO:2 or 10 SEQ ID NO:3. In yet another embodiment, the inhibitor is a shRNA molecule that inhibits expression of NR2F6, optionally as shown in SEQ ID NO:5 or 6.

The stem cells may be cancer stem cells, leukemia stem cells or myelodysplastic stem cells.

In one embodiment, the method is for treating or preventing a hematologic condition. In an embodiment, treating a hematologic condition comprises preventing the progression of the hematologic condition.

In another embodiment, the hematologic condition is acute leukemia, chronic leukemia or myelodysplastic syndrome.

In yet another embodiment, the method is for inducing differentiation of granulocytic, erythroid or megakaryocytic lineages.

In a further embodiment, the method is for reducing the number of progenitor cells. In one embodiment, the method is for treating conditions associated with leukocytosis.

In yet another embodiment, the method is for potentiating retinoic acid signaling.

In yet a further embodiment, the method is for treating disorders characterized by excessive or hyperactive mast cells.

In another aspect, the NR2F6 modulator is a NR2F6 activator.

Accordingly, in one embodiment, there is provided a method of stem cell expansion comprising administering an effective amount of a NR2F6 activator to a cell or animal in need thereof. In an embodiment, the stem cells are hematopoietic stem cells. In another embodiment, the stem cells are derived from peripheral blood, bone marrow, umbilical cord blood, embryonic stem cells or menstrual blood. In yet another embodiment, the method is used for bone marrow transplantation or cell therapies.

In another embodiment, the method is for repressing retinoic acid signaling.

In yet a further embodiment, the method is for treating dermatitis.

In another aspect, the disclosure provides a shRNA molecule comprising the sequence as shown in SEQ ID NO:5 or 6. In another embodiment, the disclosure provides a shRNA molecule consisting of the sequence as shown in SEQ ID NO:5 or 6.

Also provided are uses, pharmaceutical compositions and diagnostic methods.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1A:
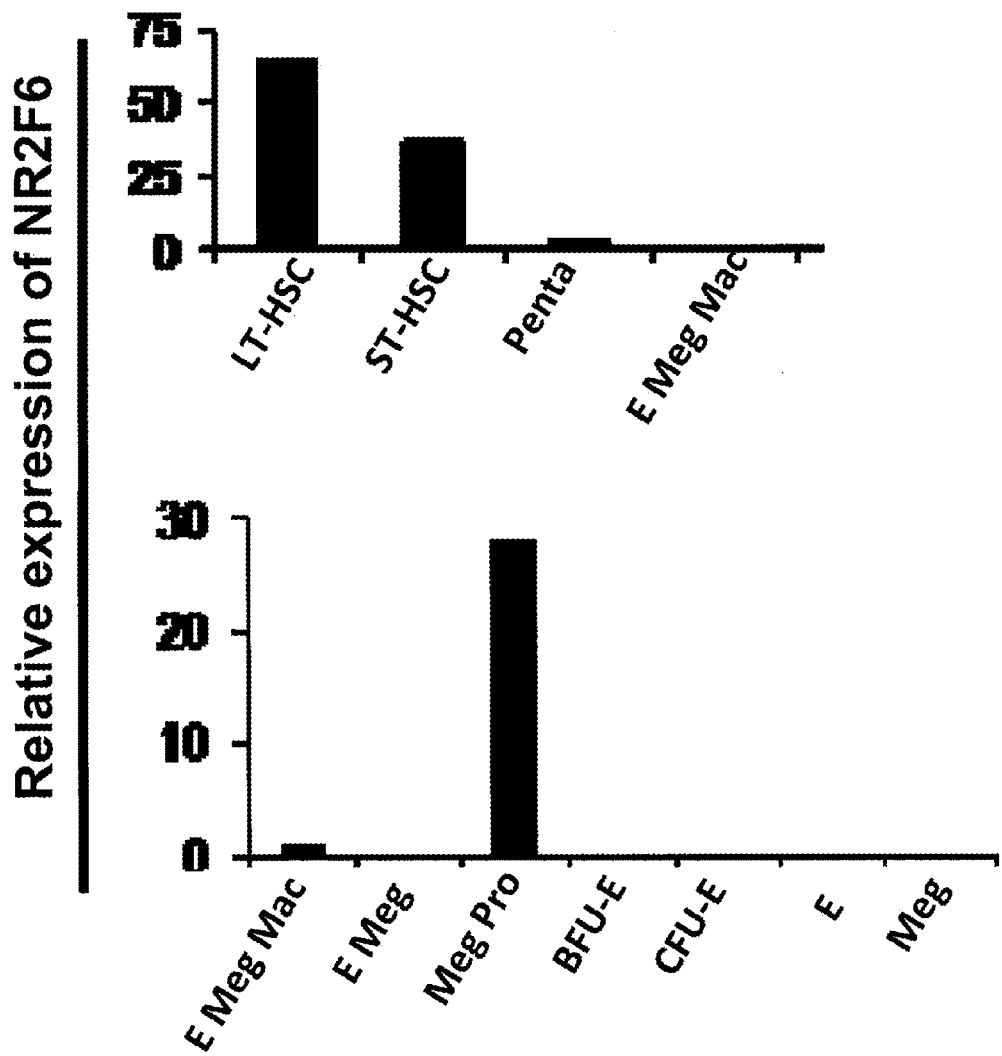
FIGS. 1A and 1B show that NR2F6 is highly expressed in both long and short term haematopoietic stem cells and that expression of NR2F6 in bone marrow from patients with acute myelogenous leukemia (AML), chronic myelomonocytic leukemia (CMML) and myelodysplastic syndrome (MDS) is greater compared to control. * denotes $p<0.05$ and ** denotes $p<0.01$ relative to normal (ANOVA & Tukey post-hoc test).

The term "NR2F6" as used herein refers to nuclear receptor subfamily2, group F, member 6 and is also referred to as v-erbA-related gene or ear-2 and includes, without limitation, the protein encoded by the gene having the sequence as shown in SEQ ID NO:1 (human) or SEQ ID NO:4 (mouse) or variants thereof and the protein having the amino acid sequence as shown in SEQ ID NO:2 (human) or SEQ ID NO:3 (mouse) or variants thereof.

The term "a cell" as used herein includes a plurality of cells and refers to all types of cells including hematopoietic and cancer cells. Administering a compound to a cell includes in vivo, ex vivo and in vitro treatment.

The term "stem cell" as used herein refers to a cell that has the ability for self-renewal and can give rise to specialized cells.

The term "effective amount" as used herein means a quantity sufficient to, when administered to an animal, effect beneficial or desired results, including clinical results, and as such, an "effective amount" depends upon the context in which it is being applied. For example, in the context of inhibiting self-renewal of stem cells, it is the amount of the NR2F6 inhibitor sufficient to achieve such an inhibition as compared to the response obtained without administration of the NR2F6 inhibitor.

The term "nucleic acid molecule" is intended to include unmodified DNA or RNA or modified DNA or RNA. For example, the nucleic acid molecules or polynucleotides of the disclosure can be composed of single- and double stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "animal" as used herein includes all members of the animal kingdom, preferably mammal. The term "mammal" as used herein is meant to encompass, without limitation, humans, domestic animals such as dogs, cats, horses, cattle, swine, sheep, goats, and the like, as well as wild animals. In an embodiment, the mammal is human.

Methods and Uses

The present inventors have found that NR2F6 is a regulator of blood stem cell self-renewal and differentiation, and of the maturation of healthy progenitor cells.

Accordingly, the present disclosure provides a method of modulating stem cell growth, proliferation and/or differentiation comprising administering an effective amount of a NR2F6 modulator to a cell or animal in need thereof.

In one aspect, the NR2F6 modulator is a NR2F6 inhibitor. In another aspect, the NR2F6 modulator is a NR2F6 activator.

Accordingly, the present disclosure provides a method of inhibiting self-renewal of stem cells comprising administering an effective amount of an inhibitor of NR2F6 to a cell or animal in need thereof. The present disclosure also provides the use of a NR2F6 inhibitor for inhibiting self-renewal of stem cells in a cell or animal in need thereof. The present disclosure further provides the use of a NR2F6 inhibitor in the preparation of a medicament for inhibiting self-renewal of stem cells in a cell or animal in need thereof. The present disclosure also provides a NR2F6 inhibitor for use in inhibiting self-renewal of stem cells in a cell or animal in need thereof.

In another embodiment, the present disclosure provides a method of inducing terminal differentiation of stem cells comprising administering an effective amount of an inhibitor of NR2F6 to a cell or animal in need thereof. The present disclosure also provides the use of a NR2F6 inhibitor for inducing terminal differentiation of stem cells in a cell or animal in need thereof. The present disclosure further provides the use of a NR2F6 inhibitor in the preparation of a medicament for inducing terminal differentiation of stem cells in a cell or animal in need thereof. The present disclosure also provides a NR2F6 inhibitor for use in inducing terminal differentiation of stem cells in a cell or animal in need thereof.

In one embodiment, the stem cells are cancer stem cells, leukemia stem cells or myelodysplastic stem cells.

The term "inhibiting self renewal of stem cells" as used herein includes but is not limited to preventing or decreasing the clonal longevity, clonogenicity, serial replating ability, clonogenic growth and/or transplantability of the stem cells.

The present inventors have also found that over-expression of NR2F6 in the bone marrow of animals greatly enhanced self-renewal ability of hematopoietic stem cells and resulted in stem cell expansion. Accordingly, the present disclosure also provides a method of stem cell expansion comprising administering an effective amount of an activator of NR2F6 to a cell or animal in need thereof. The present disclosure also provides the use of a NR2F6 activator for stem cell expansion in a cell or animal in need thereof. The present disclosure further provides the use of a NR2F6 activator in the preparation of a medicament for stem cell expansion in a cell or animal in need thereof. The present disclosure also provides a NR2F6 activator for use in activating stem cell expansion in a cell or animal in need thereof.

The term "stem cell expansion" as used herein means the maintenance, survival and/or proliferation of cells in an undifferentiated state or inhibiting differentiation and includes both ex vivo, in vitro and in vivo stem cell expansion. In one embodiment, stem cell expansion is useful for bone marrow transplantation and/or immunotherapy. In another embodiment, the stem cells are hematopoietic stem cells, optionally from the peripheral blood, bone marrow, umbilical cord blood, embryonic stem cells or menstrual blood.

Stem cell expansion is particularly useful for bone marrow transplantation and/or cellular therapies, including but not limited to generation of sufficient numbers of leukocytes for the purposes of immunotherapy, transfusion post chemotherapy, treatment of HIV and AIDS. Stem cell expansion is also useful for the expansion of autologous, allogeneic, cord blood, peripheral blood or menstrual blood stem cells for the transplantation following chemotherapy for the treatment of leukemia, solid tumours and/or non-malignant disease including but not limited to b-thalassaemia and sickle cell anemia. Expansion of stem cells is optionally in combination with soluble factors including but not limited to c-kit, IL-3, IL-11, flt-3 ligand, IL-6, and/or TPO.

In one embodiment, a NR2F6 activator is administered to suitable mammalian hematopoietic stem cells for maintaining the stem cells in an undifferentiated state while stimulating their expansion. Examples of suitable stem cells include haematopoietic stem cells from the peripheral blood, bone marrow, umbilical cord blood, embryonic stem cells or menstrual blood.

In another embodiment, a NR2F6 activator is administered to suitable mammalian hematopoietic stem cells for maintaining the stem cells in an undifferentiated state while stimulating their expansion for the purposes of cellular therapies, including but not limited to generation of sufficient numbers of leukocytes for the purposes of immunotherapy, transfusion post-chemotherapy, and/or treatment of HIV and AIDS.

In yet another embodiment, a NR2F6 activator is administered to suitable mammalian hematopoietic stem cells for maintaining the stem cells in an undifferentiated state while stimulating the expansion of either autologous, allogeneic, cord blood, peripheral blood, or menstrual blood stem cells for the transplantation following chemotherapy for the treatment of leukemia.

In a further embodiment, a NR2F6 activator is administered to suitable mammalian hematopoietic stem cells for maintaining the stem cells in an undifferentiated state while stimulating the expansion of either autologous, allogeneic, cord blood, peripheral blood, or menstrual blood stem cells for the transplantation following chemotherapy for the treatment of solid tumours.

In even yet another embodiment, a NR2F6 activator is administered to suitable mammalian hematopoietic stem cells for maintaining the stem cells in an undifferentiated state while stimulating the expansion of either autologous, allogeneic, cord blood, peripheral blood, or menstrual blood stem cells for the transplantation following treatment of non-malignant diseases including but not limited to beta-thalassaemia and sickle cell anemia.

The present inventors have shown that over-expression of NR2F6 in a portion of mouse bone marrow cells recapitulates a group of hematological conditions termed myelodysplastic syndromes. Further, overexpression of NR2F6 in bone marrow cells results in bone marrow failure and a rapidly fatal acute leukemia. Accordingly, in another aspect, the present disclosure provides a method of treating or preventing a hematologic condition comprising administering an effective amount of a modulator of NR2F6, such as a NR2F6 inhibitor or activator, to a cell or animal in need thereof. The present disclosure also provides the use of a NR2F6 modulator for treating or preventing a hematologic condition in a cell or animal in need thereof. The present disclosure further provides the use of a NR2F6 modulator in the preparation of a medicament for treating or preventing a hematologic condition in a cell or animal in need thereof. The present disclosure also provides a NR2F6 modulator for use in treating or preventing a hematologic condition in a cell or animal in need thereof.

The term "hematologic condition" as used herein refers generally to diseases of impaired blood cell self-renewal, quiescence, proliferation, differentiation, and/or maturation. These include, but are not limited to, acute leukemia, chronic leukemia, pre-leukemic conditions, myeloproliferative disorders, chronic myelomonocytic leukemia, myelodysplastic syndrome and other dysplasias, bone marrow failure disorders, anemia, idiopathic or secondary aplastic anemia, bone marrow aplasia, neutropenia, thrombocytopenia, leukocytosis, and pancytopenia.

In one embodiment, the hematologic condition is acute leukemia, chronic leukemia or myelodysplastic syndrome (MDS).

In an embodiment, the NR2F6 modulator is an inhibitor that restores the ability of bone marrow to develop into fully mature, non-dysplastic blood cells. In another embodiment, the NR2F6 inhibitor induces the functional maturation of myelodysplastic syndrome cells. In yet another embodiment, the NR2F6 inhibitor is used to treat or prevent conditions that produce insufficient quantities of blood cells including anemia and bone marrow aplasia, idiopathic or secondary aplastic anemia, thrombocytopenia, neutropenia and pancytopenia.

In another embodiment, the NR2F6 inhibitor is used to treat or prevent splenomegaly and hepatomegaly secondary to a proliferative or dysplastic disease of the bone marrow.

In yet another embodiment, the NR2F6 inhibitor is used to treat or prevent diseases of aberrant cellular proliferation or aberrant cellular differentiation.

The term "treating or preventing" as used herein refers to improving the condition, such as reducing or alleviating symptoms associated with the condition or improving the prognosis or survival of the subject.

Conventional treatment may also be used in combination with the methods and uses of the disclosure. The currently used agents used for treatment of hematopoietic conditions include, without limitation, lenalidomide, thalidomide, 5-azacitidine (Vidaza), lenalidomide (Revlimid), erythropoietin, gm-csf, g-csf, IL-3, ATG, ALG, methylprednisolone and cyclosporine, daunorubicin (Cerubidine®), doxorubicin (Adriamycin®), cytarabine (araC; Cytosar-U®), 6-thioguanine (Tabloid®), idarubicin (Idamycin®), mitoxantrone (Novantrone®), etoposide (VePesid®), amsacrine (AMSA), cytarabine (ara-C; Cytosar-U®), and 6-thioguanine (Tabloid®), all-trans retinoic acid (ATRA), hydroxyurea (Hydrea®), busulfan (Myleran®), prednisone, vincristine sulfate (Oncovin®), Interferon alpha, vincristine (Oncovin®), L-asparaginase (Elspar®), Cyclophosphamide (Neosar®), 6-thioguanine (Tabloid®), 6-mercaptopurine (6-MP; Purinethol®).

The present inventors have also shown that NR2F6 functions to inhibit leukemia cell differentiation. The present inventors have shown direct evidence that knocking down expression of NR2F6 induces the spontaneous differentiation, maturation and death of human leukemia cells. Accordingly, in another aspect, the present disclosure provides a method of inducing cell differentiation comprising administering an effective amount of an inhibitor of NR2F6 to a cell or animal in need thereof. The present disclosure also provides the use of a NR2F6 inhibitor for inducing cell differentiation in a cell or animal in need thereof. The present disclosure further provides the use of a NR2F6 inhibitor in the preparation of a medicament for inducing cell differentiation in a cell or animal in need thereof. The present disclosure also provides a NR2F6 inhibitor for use in inducing cell differentiation in a cell or animal in need thereof.

The term "inducing cell differentiation" as used herein means inducing the cell to differentiate or mature from a stem cell or progenitor to later lineage cell stages and includes, without limitation, hematopoietic differentiation, myelodysplastic syndrome stem and progenitor cell differentiation, maturation of myelodysplastic syndrome cells, granulocytic differentiation, erythroid differentiation, and megakaryocytic differentiation. In one embodiment, terminal differentiation is induced. In another embodiment, inducing cell differentiation comprises increasing the sensitivity of the cells to undergo terminal or morphological differentiation.

In an embodiment, the method induces differentiation of the granulocytic, erythroid, or megakaryocytic lineages for the treatment of cytopenia.

In another embodiment, the present disclosure provides a method of reducing the number of progenitors comprising administering an effective amount of an inhibitor of NR2F6 to a cell or animal in need thereof. The present disclosure also provides the use of a NR2F6 inhibitor for reducing the number of progenitors in a cell or animal in need thereof. The present disclosure further provides the use of a NR2F6 inhibitor in the preparation of a medicament for reducing the number of progenitors in a cell or animal in need thereof. The present disclosure also provides a NR2F6 inhibitor for use in reducing the number of progenitors in a cell or animal in need thereof.

Reduction of the number of progenitors is useful for the treatment of conditions characterized by leukocytosis. In one embodiment, the progenitors are immature granulocyte progenitors, immature erythroid progenitors or immature megakaryocyte progenitors.

In another aspect, the present disclosure provides a method of preventing the progression of a hematologic condition comprising administering an effective amount of an inhibitor of NR2F6 to a cell or animal in need thereof. The present disclosure also provides the use of a NR2F6 inhibitor for preventing the progression of a hematologic condition in a cell or animal in need thereof. The present disclosure further provides the use of a NR2F6 inhibitor in the preparation of a medicament for preventing the progression of a hematologic condition in a cell or animal in need thereof. The present disclosure also provides a NR2F6 inhibitor for use in preventing the progression of a hematologic condition in a cell or animal in need thereof.

The term "preventing the progression of a hematologic condition" means blocking or delaying the progression of the condition and includes, without limitation, the transformation of preleukemic states, chronic leukemic states and MDS into acute leukemia.

The present inventors have found that NR2F6 functions to repress retinoic acid signaling. Accordingly, in another embodiment, the present disclosure provides a method of potentiating retinoic acid signaling comprising administering an effective amount of an inhibitor of NR2F6 to a cell or animal in need thereof. The present disclosure also provides the use of a NR2F6 inhibitor for potentiating retinoic acid signaling in a cell or animal in need thereof. The present disclosure further provides the use of a NR2F6 inhibitor in the preparation of a medicament for potentiating retinoic acid signaling in a cell or animal in need thereof. The present disclosure also provides a NR2F6 inhibitor for use in potentiating retinoic acid signaling in a cell or animal in need thereof.

The phrase "potentiating retinoic acid signaling" as used herein means potentiating the actions of natural or synthetic retinoids. Potentiating retinoic acid signaling is useful for treating or preventing conditions, including but not limited to, leukemia, in particular, acute promyelocytic leukemia, cutaneous T-cell lymphoma, nevoid basal carcinoma syndrome, non-small cell lung cancer as well as for treating or preventing dermatological conditions, including but not limited to, acne vulgaris, psoriasis, symmetrical progressive erythrokeratomderma, pityriasis rubra pilaris, kid syndrome, palmoplantar keratoderma, epidermolytic hyperkeratosis, xeroderma pigmentosum, epidermodysplasia verruciformis, Darier's disease, skin discolouration, flat warts, ichthyosis, and other disorders of keratinisation as well as for cosmetic applications, including but not limited to, treating or preventing premature aging of the skin caused by overexposure to the sun (photodamage) including but not limited to sunspots.

In an embodiment, a NR2F6 inhibitor is formulated for topical administration in combination with natural or synthetic retinoid compounds for use in cosmetic applications including but not limited to improving premature aging of the skin caused by overexposure to the sun (photodamage) including but not limited to sunspots.

In another embodiment, a NR2F6 inhibitor is formulated for oral, intravenous, or subcutaneous administration in combination with natural or synthetic retinoid compounds for the treatment of cutaneous T-cell lymphoma, nevoid basal cell carcinoma, non-small cell lung cancer, and acute promyeolcytic leukemia.

In another embodiment, the present disclosure provides a method of repressing retinoic acid signaling comprising administering an effective amount of an activator of NR2F6 to a cell or animal in need thereof. The present disclosure also provides the use of a NR2F6 activator for repressing retinoic acid signaling in a cell or animal in need thereof. The present disclosure further provides the use of a NR2F6 activator in the preparation of a medicament for repressing retinoic acid signaling in a cell or animal in need thereof. The present disclosure also provides a NR2F6 activator for use in repressing retinoic acid signaling in a cell or animal in need thereof.

Repression of retinoic acid signaling is useful in treating psychological disorders, including but not limited to Vitamin A or synthetic retinoid induced neurotoxicity, psychosis, depression or suicidal ideation. Repression of retinoic acid signaling induced by Vitamin A or synthetic retinoids is also useful for stimulating neurogenesis, improving serotonin signaling and/or for treating or preventing acute toxicity induced by vitamin A or synthetic retinoids.

In another aspect, the present disclosure provides a method of treating disorders characterized by excessive or hyperactive mast cells comprising administering an effective amount of an inhibitor of NR2F6 to a cell or animal in need thereof. The present disclosure also provides the use of a NR2F6 inhibitor for treating disorders characterized by excessive or hyperactive mast cells in a cell or animal in need thereof. The present disclosure further provides the use of a NR2F6 inhibitor in the preparation of a medicament for treating disorders characterized by excessive or hyperactive mast cells in a cell or animal in need thereof. The present disclosure also provides a NR2F6 inhibitor for use in for treating disorders characterized by excessive or hyperactive mast cells in a cell or animal in need thereof. In one embodiment, the disorders characterized by excessive or hyperactive mast cells are mastocytosis, allergy or asthma.

The NR2F6 modulator can be a NR2F6 activator or a NR2F6 inhibitor.

The term "NR2F6 activator" as used herein includes all substances that can increase expression or activity of NR2F6 and includes, without limitation, additional NR2F6 nucleic acid or protein or fragments thereof, small molecule activators, antibodies (and fragments thereof), and other substances that can activate NR2F6 expression or activity.

The term "NR2F6 inhibitor" as used herein includes any substance that is capable of inhibiting the expression or activity of NR2F6 and includes, without limitation, antisense nucleic acid molecules, siRNAs or shRNAs, proteins, antibodies (and fragments thereof), small molecule inhibitors and other substances directed at NR2F6 expression or activity. In an embodiment, the NR2F6 inhibitor is a protein kinase, phosphatase or inhibitor of protein kinase.

In one embodiment, inhibition of NR2F6 is through the use of histone deacetylase inhibitor drugs. Examples of these drugs include depsipeptide, butyrate derivatives, valproic acid, and suberoylanilide hydroxamic acid. Furthermore, it is apparent to one skilled in the art that natural or synthetic ligands that antagonistically modulate NR2F6 would have an additive effect with histone deacetylase inhibitor drugs.

In an embodiment, the NR2F6 inhibitor is an antisense nucleic acid molecule that inhibits expression of NR2F6. In another embodiment, the inhibitor is an antisense nucleic acid sequence of the gene encoding human NR2F6 as shown in SEQ ID NO:1 or of the gene encoding mouse NR2F6 as shown in SEQ ID NO:4 or variants thereof. In yet another embodiment, the NR2F6 inhibitor is a siRNA molecule or shRNA molecule that inhibits expression of NR2F6. In one embodiment, the NR2F6 inhibitor is an shRNA as shown in SEQ ID NO:5 or SEQ ID NO:6 or variants thereof. In yet a further embodiment, the NR2F6 inhibitor is an aptamer that binds and inhibits NR2F6 activity. Also provided herein are shRNA molecules comprising the sequence as shown in SEQ ID NO:5 or 6 or variants thereof. In another embodiment the shRNA molecule consists of the sequence as shown in SEQ ID NO:5 or 6.

The term "antisense nucleic acid" as used herein means a nucleotide sequence that is complementary to its target e.g. a NR2F6 transcription product. The nucleic acid can comprise DNA, RNA or a chemical analog, that binds to the messenger RNA produced by the target gene. Binding of the antisense nucleic acid prevents translation and thereby inhibits or reduces target protein expression. Antisense nucleic acid molecules may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The term "siRNA" refers to a short inhibitory RNA that can be used to silence gene expression of a specific gene. The siRNA can be a short RNA hairpin (e.g. shRNA) that activates a cellular degradation pathway directed at mRNAs corresponding to the siRNA. Methods of designing specific siRNA molecules or shRNA molecules and administering them are known to a person skilled in the art. It is known in the art that efficient silencing is obtained with siRNA duplex complexes paired to have a two nucleotide 3' overhang. Adding two thymidine nucleotides is thought to add nuclease resistance. A person skilled in the art will recognize that other nucleotides can also be added.

Aptamers are short strands of nucleic acids that can adopt highly specific 3-dimensional conformations. Aptamers can exhibit high binding affinity and specificity to a target molecule. These properties allow such molecules to specifically inhibit the functional activity of proteins and are included as agents that inhibit NR2F6.

In another embodiment, the NR2F6 modulator is an antibody specific to NR2F6. In one embodiment, the inhibitor is a blocking antibody that binds the NR2F6 amino acid sequence as shown in SEQ ID NO:2 or SEQ ID NO:3 or a variant thereof. In another embodiment, the activator is an antibody that binds the NR2F6 amino acid sequences as shown in SEQ ID NO:2 or 3 or a variant thereof and activates NR2F6.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and Domain Antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Antibodies to such proteins may be prepared using techniques known in the art such as those described by Kohler and Milstein, Nature 256, 495 (1975) and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the present disclosure, antibodies are understood to include monoclonal antibodies, polyclonal antibodies, antibody fragments (e.g., Fab, and F(ab')2) and recombinantly produced binding partners.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Continuous cultures of fused cells secreting antibody of predefined specificity. Nature 256:495-497, 1975) as well as other techniques such as the human B-cell hybridoma technique (Kozbor, D, and Roder, J: The production of monoclonal antibodies from human lymphocytes. Immunology Today 4:3 72-79, 1983), the EBV-hybridoma technique to produce human monoclonal antibodies (Cole et al. Monoclonal Antibodies in Cancer Therapy (1985) Allen R. Bliss, Inc., pages 77-96) and screening of combinatorial antibody libraries (Huse, W, Sastry, L, Iverson, S, Kang, A, Alting-Mees, M, Burton, D, Benkovic, S, and Lerner, R: Generation of a large combinatorial library of the immunoglobulin repertoire in phage lambda. Science 246:4935 1275-1282, 1989). Hybridoma cells can be screened immunochemically for production of antibodies specifically reactive with the protein or fragment thereof and the monoclonal antibodies can be isolated. Therefore, the disclosure also contemplates hybridoma cells secreting monoclonal antibodies with specificity for NR2F6 or a fragment thereof.

For producing recombinant antibodies (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

Chimeric antibody derivatives, i.e., antibody molecules that combine a non-human animal variable region and a human constant region are also contemplated within the scope of the disclosure. Chimeric antibody molecules can include, for example, the antigen binding domain from an antibody of a mouse, rat, or other species, with human constant regions. Conventional methods may be used to make chimeric antibodies containing the immunoglobulin variable region which recognizes NR2F6 or a fragment thereof (See, for example, Morrison et al. (Chimeric Human Antibody Molecules: Mouse Antigen-Binding Domains with Human Constant Region Domains. *PNAS* 81:21 6851-6855, 1984), and Takeda et al. (Construction of chimaeric processed immunoglobulin genes containing mouse variable and human constant region sequences. *Nature* 314:452-454), and the patents of Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with NR2F6 or a fragment thereof as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al. (Construction and Testing of Mouse—Human Heteromyelomas for Human Monoclonal Antibody Production. *PNAS* 80:12 7308-7312, 1983), Kozbor et al., supra; Olsson et al. (*Methods in Enzymol,* 92:3-16 1982) and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against NR2F6 or a fragment thereof may also be generated by screening expression libraries encoding immunoglobulin genes, or portions thereof, expressed in bacteria with peptides produced from the nucleic acid molecules encoding NR2F6 or a fragment thereof. For example, complete Fab fragments, VH regions and FV regions can be expressed in bacteria using phage expression libraries (See for example Ward et al. (Binding activities of a repertoire of single immunoglobulin variable domains secreted from *Escherichia coli. Nature* 348: 544-546, 1989), Huse et al., supra and McCafferty et al (Phage antibodies: filamentous phage displaying antibody variable domains. *Nature* 25 348:552-555, 1989)).

Antibodies may also be prepared using DNA immunization. For example, an expression vector containing a nucleic acid encoding NR2F6 or a fragment thereof may be injected into a suitable animal such as mouse. The protein will therefore be expressed in vivo and antibodies will be induced. The antibodies can be isolated and prepared as described above for protein immunization.

The term "variant" as used herein includes modifications, substitutions, additions, derivatives, analogs, fragments or chemical equivalents of the NR2F6 nucleic acid or amino acid sequences disclosed herein that perform substantially the same function in substantially the same way. For instance, the variants of the NR2F6 peptides would have the same function, for example, of inhibiting cell differentiation or potentiating retinoic acid signaling or for enhancing stem cell expansion or repressing retinoic acid signaling. Variants of NR2F6 peptide inhibitors would have the same function as being useful to inhibit NR2F6. Variants of NR2F6 peptide activators would have the same function as being useful to activate NR2F6.

Variants also include peptides with amino acid sequences that are substantially or essentially identical to the amino acid sequences of SEQ ID NO:2 or 3 or nucleic acid molecules with nucleic acid sequence that are substantially or essentially identical to the nucleic acid sequence of SEQ ID NO:1 or 4.

The term "substantially identical" or "essentially identical" as used herein means an amino acid sequence that, when optimally aligned, for example using the methods described herein, share at least 75%, 80%, 85%, 90%, 95%, 96%, 97%, 98%, 99%, or 100% sequence identity with a second amino acid sequence.

The term "sequence identity" as used herein refers to the percentage of sequence identity between two polypeptide and/or nucleotide sequences.

To determine the percent identity of two amino acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues at corresponding amino acid positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, *Proc. Natl. Acad. Sci.* U.S.A. 87:2264-2268, modified as in Karlin and Altschul, 1993, *Proc. Natl. Acad. Sci.* U.S.A. 90:5873-5877. Such an algorithm is incorporated into the NBLAST and XBLAST programs of Altschul et al., 1990, *J. Mol. Biol.* 215:403. BLAST nucleotide searches can be performed with the NBLAST nucleotide program parameters set, e.g., for score=100, wordlength=12 to obtain nucleotide sequences homologous to a nucleic acid molecule of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, *Nucleic Acids Res.* 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The percentage of identity between two polypeptide sequences, the amino acid sequences of such two sequences are aligned, for example using the Clustal W algorithm (Thompson, J D, Higgins D G, Gibson T J, 1994, *Nucleic Acids Res.* 22(22): 4673-4680.), together with BLOSUM 62 scoring matrix (Henikoff S, and Henikoff J. G., 1992, *Proc. Natl. Acad. Sci.* USA 89: 10915-10919.) and a gap opening penalty of 10 and gap extension penalty of 0.1, so that the highest order match is obtained between two sequences wherein at least 50% of the total length of one of the sequences is involved in the alignment.

Other methods that may be used to align sequences are the alignment method of Needleman and Wunsch (Needleman and Wunsch. *J. Mol. Biol.,* 1970, 48:443), as revised by Smith and Waterman (Smith and Waterman. *Adv. Appl. Math.* 1981, 2:482) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton *SIAM J. Applied Math.* 1988, 48: 1073) and those described in Computational Molecular Biology (Computational Molecular Biology, Lesk, e.d. Oxford University Press, New York, 1988, *Biocomputing: Informatics and Genomics Projects*). Generally, computer programs will be employed for such calculations.

The disclosure further encompasses nucleic acid molecules that differ from any of the nucleic acid molecules disclosed herein in codon sequences due to the degeneracy of the genetic code.

The NR2F6 inhibitors or activators described herein may also contain or be used to obtain or design "peptide mimetics". For example, a peptide mimetic may be made to mimic the function of a NR2F6 activator or inhibitor. "Peptide mimetics" are structures which serve as substitutes for peptides in interactions between molecules (See Morgan et al (1989), *Ann. Reports Med. Chem.* 24:243-252 for a review). Peptide mimetics include synthetic structures which mayor may not contain amino acids and/or peptide bonds but retain the structural and functional features. Peptide mimetics also include molecules incorporating peptides into larger molecules with other functional elements (e.g., as described in WO 99/25044). Peptide mimetics also include peptoids, oligopeptoids (Simon et al (1972) Proc. Natl. Acad. Sci. USA 89:9367) and peptide libraries containing peptides of a designed length representing all possible sequences of amino acids corresponding to a NR2F6 inhibitor peptide.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of the secondary structures of the proteins described herein. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

The nucleic acid molecules disclosed herein may be incorporated in a known manner into an appropriate expression vector which ensures good expression of the polypeptides. Various constructs can be used to deliver nucleic acid molecules described herein. For example retroviral constructs such as lentiviral constructs are useful for expressing physiological levels of protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The disclosure therefore includes a recombinant expression vector containing a nucleic acid molecule disclosed herein, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors may also contain a selectable marker gene which facilitates the selection of host cells transformed or transfected with a recombinant molecule disclosed herein. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of the recombinant expression vectors disclosed herein and in particular to determine the effect of a mutation on expression and phenotype. It will be appreciated that selectable markers can be introduced on a separate vector from the nucleic acid of interest.

Suitable host cells include a wide variety of prokaryotic and eukaryotic host cells. For example, the proteins of the disclosure may be expressed in bacterial cells such as *E. coli*, insect cells (using baculovirus), yeast cells or mammalian cells. Other suitable host cells can be found in Goeddel (Goeddel, Gene Expression Technology: Methods in Enzymology 185, Academic Press, San Diego, Calif. 1990).

25 Pharmaceutical Compositions

Another aspect of the present disclosure is a pharmaceutical composition comprising a NR2F6 modulator, such as a NR2F6 inhibitor or NR2F6 activator, for use in the methods described herein. Accordingly, the disclosure provides a pharmaceutical composition comprising an effective amount of a NR2F6 inhibitor or NR2F6 activator in admixture with a pharmaceutically acceptable carrier or diluent. In one embodiment, the pharmaceutical composition is used to inhibit NR2F6. In another embodiment, the pharmaceutical composition is used to activate NR2F6. In another embodiment, the pharmaceutical composition is used to treat hematopoietic conditions as described herein.

The term "pharmaceutically acceptable" as used herein means compatible with the treatment of animals, including, humans.

The present disclosure also provides a composition comprising a NR2F6 inhibitor in combination with a natural or synthetic vitamin A analogue.

The NR2F6 inhibitors or NR2F6 activators may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present disclosure is defined as an amount effective, at dosages and for periods of time necessary to achieve the desired result. For example, a therapeutically active amount of a substance may vary according to factors such as the disease state, age, sex, and weight of the individual, and the ability of inhibitor to elicit a desired response in the individual. Dosage regime may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, intramuscular, etc.), oral administration, inhalation, intranasal, transdermal administration (such as topical cream or ointment, etc.), or suppository applications. In one embodiment, the active substance is administered by inhalation or intranasally. In another embodiment, the active substance is administered topically. Depending on the route of administration, the active substance may be coated in a material to protect the compound from the action of enzymes, acids and other natural conditions which may inactivate the compound. The active substance may be formulated into delayed release formulations such that NR2F6 can be inhibited or activated for longer periods of time than a conventional formulation.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences (2000-20th edition) Mack Publishing Company). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Diagnostic Methods

The present inventors have found that NR2F6 is overexpressed in patients with acute leukemia, chronic myelomonocytic leukemia and myelodysplastic syndromes. Accordingly, in another aspect, the disclosure provides a method of monitoring or assessing a hematological condition comprising (a) determining the level of NR2F6 expression in a sample from a subject; and (b) comparing the level of expression of NR2F6 from the sample with a control; wherein an increase in expression of NR2F6 in the sample from the subject as compared to the control is indicative of a hematological condition.

The term "monitoring or assessing" as used herein includes, monitoring the occurrence, development, treatment and/or progression of the hematological condition. In an embodiment, the hematological condition is MDS or leukemia.

The term "sample" as used herein refers to any fluid, cell or tissue sample from a subject. In one embodiment, the sample is blood.

The term "subject" as used herein refers to any member of the animal kingdom, optionally, a human.

The term "control" as used herein refers to a sample from a subject or a group of subjects who are either known as having a particular condition or trait or as not having a particular condition or trait. The control can vary depending on what is being monitored, assessed or diagnosed. The term "control" as used herein can also refer to a predetermined standard or reference range of values.

The term "difference in expression of NR2F6 in the sample from the subject as compared to the control" means that NR2F6 is differentially expressed in the sample from the subject as compared to the control.

The term "differentially expressed" or "differential expression" as used herein refers to a difference in the level of expression of NR2F6. The term "difference in the level of expression" refers to an increase or decrease in the measurable expression level of NR2F6 as compared with the measurable expression level of NR2F6 in a second sample or control. The term can also refer to an increase or decrease in the measurable expression level of NR2F6 in a population of samples as compared with the measurable expression level of NR2F6 in a second population of samples. In one embodiment, the differential expression can be compared using the ratio of the level of expression of NR2F6 as compared with the expression level of the NR2F6 of a control, wherein the ratio is not equal to 1.0. For example, a protein is differentially expressed if the ratio of the level of expression in a first sample as compared with a second sample is greater than or less than 1.0. For example, a ratio of greater than 1, 1.2, 1.5, 1.7, 2, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, NR2F6 is identified as being differentially expressed as between a first and second population when the p-value is less than 0.1, preferably less than 0.05, more preferably less than 0.01, even more preferably less than 0.005, the most preferably less than 0.001.

"Determining the expression of NR2F6" can be readily accomplished by a person skilled in the art. In one embodiment, a probe that hybridizes to the mRNA sequence of the NR2F6 nucleic acid sequence as shown in SEQ ID NOs:1 or 4 or variants thereof can be used to detect and quantify the amount of NR2F6 mRNA in the sample.

A nucleotide probe may be labelled with a detectable marker such as a radioactive label which provides for an adequate signal and has sufficient half life such as 32P, 3H, 14C or the like. Other detectable markers which may be used include antigens that are recognized by a specific labeled antibody, fluorescent compounds, enzymes, antibodies specific for a labeled antigen, and chemiluminescent compounds. An appropriate label may be selected having regard to the rate of hybridization and binding of the probe to the nucleotide to be detected and the amount of nucleotide available for hybridization.

Hybridization conditions which may be used in methods of the disclosure are known in the art and are described for example in Sambrook J, Fritch E F, Maniatis T. In: Molecular Cloning, A Laboratory Manual, 1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker.

In another embodiment, primers that are able to amplify the NR2F6 sequence can be used in a quantitative PCR assay to determine the expression level of NR2F6. In one embodiment, forward and reverse primers used for amplifying NR2F6 are 5'-TCTCCCAGCTGTTCTTCATGC-3' (SEQ ID NO:7) and 5'-CCAGTTGAAGGTACTCCCCG-3' (SEQ ID NO:8).

The length and bases of primers for use in a PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the disclosure are oligonucleotides, i.e., molecules containing two or more deoxyribonucleotides of the nucleic acid molecules of the disclosure which occur naturally as in a purified restriction endonuclease digest or are produced synthetically using techniques known in the art such as for example phosphotriester and phosphodiester methods (See Good et al. Nucl. Acid Res 4:2157, 1977) or automated techniques (See for example, Conolly, B. A. Nucleic Acids Res. 15:15(7): 3131, 1987). The primers are capable of acting as a point of initiation of synthesis when placed under conditions which permit the synthesis of a primer extension product which is complementary to a DNA sequence of the disclosure, i.e., in the presence of nucleotide substrates, an agent for polymerization such as DNA polymerase and at suitable temperature and pH. Preferably, the primers are sequences that do not form secondary structures by base pairing with other copies of the primer or sequences that form a hairpin configuration. The primer optionally comprises between about 7 and 25 nucleotides.

The primers may be labelled with detectable markers which allow for detection of the amplified products. Suitable detectable markers are radioactive markers such as P-32, S-35, 1-125, and H-3, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the disclosure or oligonucleotide fragment thereof, which is to be amplified. Restriction site linkers may also be incorporated into the primers allowing for digestion of the amplified products with the appropriate restriction enzymes facilitating cloning and sequencing of the amplified product.

In yet another embodiment, antibodies that bind NR2F6 as shown in SEQ ID NO:2 or 3 or variants or homologs thereof can be used to detect NR2F6 protein levels.

The antibodies may be labelled with a detectable marker including various enzymes, fluorescent materials, luminescent materials and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, 1131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

Antibodies reactive against NR2F6 protein may be used to detect NR2F6 in various samples, for example they may be used in any known immunoassays which rely on the binding interaction between an antigenic determinant of a protein of the disclosure and the antibodies. Examples of such assays are radioimmunoassays, western immunoblotting, enzyme immunoassays (e.g., ELISA), immunofluorescence, immunoprecipitation, latex agglutination, hemagglutination, and histochemical tests. Thus, the antibodies may be used to identify or quantify the amount of a protein in a sample.

Model Organisms

In another aspect, overexpression of NR2F6 in an animal may provide a model for diseases such as myelodysplastic syndrome. Progress in understanding MDS has been hampered by the lack of suitable cell lines or animal models for this disease. A mouse model that accurately recapitulates the essential qualities of MDS—stem cell competitive advantage, dysplastic haematopoiesis, peripheral blood cytopenias, and progression to acute leukemia—would be tremendously valuable for investigations of the pathological mechanisms of these qualities and for preclinical testing of new MDS therapies. In this embodiment over-expression of NR2F6 in a chimerical mouse model provides an animal model for the study of MDS. Specific transplantation of murine haematopoietic cells engineered to overexpress NR2F6 causes myelodysplastic syndrome and promotes the development of acute myelogenous leukemia. This model, recapitulates the morphological abnormalities of MDS haematopoiesis as well as the transition of MDS to acute leukemia. This model is based on unregulated expression of the orphan nuclear receptor NR2F6 in murine haematopoietic stem and progenitor cells (HSCs).

Accordingly, in one embodiment, the present disclosure provides a cell transformed with a NR2F6 gene operatively linked to a promoter that drives overexpression of the gene. In another embodiment, the present disclosure provides a transgenic animal comprising the cell having the NR2F6 gene operatively linked to a promoter that drives overexpression of the gene. In an embodiment, the animal is a rodent, optionally, a mouse.

"Operatively linked" is intended to mean that the nucleic acid is linked to regulatory sequences in a manner which allows expression of the nucleic acid.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Materials & Methods
Cell Lines

U937 cells were purchased from ATCC and grown in RPMI supplemented with 10% FBS. 32Dcl3 cells were purchased from ATCC and grown in RPMI with 1 ng/mL of rmIL-3. The 293GPG retroviral packaging cell line (a gift of Richard Mulligan, Harvard University) was grown in DMEM medium supplemented with 10% FBS, tetracycline (1 mg/mL), G418 (0.3 mg/mL) and puromycin (2 mg/mL).

Generation of Retroviruses

NR2F6 cDNA (a kind gift from John Ladias, Harvard University) was subcloned into the pcDNA3.1V5/HIS vector (Invitrogen). V5-tagged NR2F6 was subsequently subcloned into the MMP retrovector such that it lay upstream of an IRES (internal ribosome entry sequence)-GFP cassette. VSV-G pseudotyped retroviral particles were generated by transient transfection of 293GPG cells with 25 ug of plasmid in lipofectamine 2000. Viral supernatant was collected for seven days from cultures of these cells in media containing high glucose DMEM with 10% FBS that contained no tetracycline, G418 or puromycin. Viral stocks were concentrated by centrifugation at 16,500 RPM for 90 minutes. In some experiments producer cell lines that stably express the MMP-NR2F6 or MMP-GFP retroviral construct were generated for the production of viral stock. Virus was produced from these cell lines by culturing in high glucose DMEM that contained no tetracycline, G418 or puromycin. Following 7 days of culture viral stock was concentrated by centrifugation at 16,500 RPM for 90 minutes. For U937 and 32D infections, cells were infected at a multiplicity of infection (MOI) of 2. GFP positive cells were harvested by FACS 48 h after infection.

Patient Material

Leukemia and healthy BM cells, collected with informed consent and with institutional ethics board approval and stored in our tissue bank, were used to assess expression of NR2F6. The French-American British classification of the AML samples consisted of 6 AML-M4, 7 AML-M4eo, 1 AML-M3 and 1 AML-M1.

Real-time PCR

RNA was isolated from $1 \times 10^6$ cells using Trizol reagent (Invitrogen) and first strand cDNA was synthesized using SuperScript reverse transcriptase (Qiagen) according to manufacturer's instructions. Real time PCR was performed according to manufacturer's instructions using SYBR Green Master Mix (Applied Biosystems, Foster City, Calif.) and analysed using the delta-delta CT method. The forward and reverse primers used for NR2F6 are 5'-TCTCCCAGCTGT-TCTTCATGC-3' (SEQ ID NO:7) and 5'-CCAGTTGAAGG-TACTCCCCG-3' (SEQ ID NO:8), respectively, and for GAPDH 5'-GGCCTCCAAGGAGTAAGACC-3' (SEQ ID NO:9) and 5'-AGGGGTCTACATGGCAACTG-3' (SEQ ID NO:10). Threshold cycle ($C_T$) values were calculated in each sample for NR2F6 and normalized to the $C_T$ for the housekeeping gene GAPDH (delta-$C_T$). The relative quantity of NR2F6 expression in samples relative to control was be determined as the delta-$C_T$ of the sample subtracted from the delta-$C_T$ of control, to the exponent 2(delta-delta-$C_T$). For analysis of NR2F6 expression in patient samples the mean delta-$C_T$ of all normal samples was used to calculate delta-delta-$C_T$ values.

Differentiation Assessment and Induction

Differentiation was induced in the U937 cell line by treatment with 10 nM TPA (Sigma), 1 uM ATRA (Sigma), or 1.25% v/v DMSO (Sigma) respectively. Immunostaining for the maturation marker CD11b (eBioscience) was performed for twenty minutes in the dark according to manufacturer's instructions and cells were analysed by flow cytometry. Nitroblue tetrazolium (NBT) reduction test (Sigma) was performed according to the manufacturer's instructions, with a minimum of 300 cells scored per slide in three different fields of view. Each experimental timepoint was conducted in triplicate.

Bone Marrow Transduction

Using the retroviral constructs described above, expression of NR2F6 was forced in primary murine BM cells and monitor the effects on differentiation using colony assays. Donor 12-week old C57BI/6 mice were given 5 fluorouracil, 150 μg/g body mass, by intraperitoneal injection and humanely killed ninety-six hours later. Bone marrow was collected from femurs and tibiae and cultured in Iscove's Modified Dulbecco's Medium supplemented with foetal bovine serum (5%), c-Kit ligand conditioned medium (3%), Flt-3 (30 ng/mL), and TPO (30 ng/mL), conditions that minimize differentiation but initiate cycling of long-term repopulating cells. After 24 hours of culture, the cells were infected with MMP-GFP or MMP-NR2F6 retroviral supernatant at a multiplicity of infection (MOI) of 100. Forty-eight hours after retroviral infection GFP-positive cells were collected by fluorescence activated cell sorting (FACS).

Methylcellulose Colonies

Following bone marrow transduction with MMP-GFP or MMP-NR2F6 GFP positive cells were collected by FACS and plated in methylcellulose medium supplemented with cytokines (c-Kit ligand, IL-3, IL-6, and erythropoietin) that favour multi-lineage terminal differentiation (Methocult GF 3434, Stem Cell Technologies). Colony formation was evaluated after 12-14 days; clusters containing more than 30 cells will be scored as a colony. Accuracy of colony identification and morphological maturity of colony cells was confirmed by spreading and staining individual colonies on glass slides. Cultures were evaluated for their number of colonies, colony lineage (granulocyte-monocyte, erythroid, or mixed) and morphology. GFP expression was confirmed by fluorescence microscopy. Differences in colony numbers between NR2F6 and controls will be tested for statistical significance with Student's t-test. Secondary colony formation was tested by harvesting an entire primary colony cultures, washing the cells two times with PBS, and plating 10,000 cells in methylcellulose a second time. Secondary colonies were enumerated 12-14 days following a secondary plating.

Ex Vivo Suspension Culture

Following transduction of mouse bone marrow with MMP-GFP or MMP-NR2F6, cells were placed unsorted into cultured in IMDM with 5% FBS, 10% v/v IL-3 conditioned medium from WEHI cells, 1 ng/mL IL-6 and 3% v/v c-kit ligand conditioned medium. Following ten days of culture the cells were washed twice with PBS, stained with either fluorescently labelled c-kit or with fluorescently labelled CD11b and GR-1, and analysed by flow cytometry.

Hematopoietic Stem Cell Transplants

Bone marrow transplant recipients were generated that received either chimerical NR2F6 or GFP transduced grafts or grafts that contained 100% sorted bone marrow cells.

To generate recipients transplanted with bone marrow grafts containing a chimera of transduced and wild-type cells 5FU-primed C57BI/6 bone marrow cells were transduced with either MMP-GFP or MMP-NR2F6 as described above. Cells were then sorted by FACS. Transduced (GFP or NR2F6) and untransduced donor cells were mixed at a ratio of between 10:90 to 30:70 (transduced:untransduced), maintaining a constant total graft size of between $4 \times 10^4$ to $1 \times 10^5$ cells per recipient. All recipients of a given cohort received the same graft size. Primary chimerical transplants were performed as described. In some experiments chimerical transplant recipients were harvest at 4-6 weeks post transplant for analysis, and bone marrow was transplanted into another lethally irradiated mouse by tail-vein injection. Secondary recipients of chimerical bone marrow were harvested at either early time points 4-6 weeks or at late time points 12-16 weeks.

To generate recipients transplanted with bone marrow grafts containing 100% transduced bone marrow cells 5FU-primed C57Bl/6 bone marrow cells were transduced with either MMP-GFP or MMP-NR2F6 as described above. Cells were then sorted by FACS and introduced into recipient mice by tail vein injection at a dosage of between $4 \times 10^4$ and $1 \times 10^5$ cells per recipient. All recipients of a given cohort received the same graft size. Recipient C57Bl/6 mice were treated with 900 cGy prior to transplantation—it was previously determined that this radiation dose is the lowest reliably lethal dose for this strain.

For the competitive transplant experiment (FIG. 25) animals were prepared as described in the generation of recipients transplanted with bone marrow grafts containing a chimera of transduced and wild-type cells. The percentage of marked cells was determined based on expression of GFP using flow cytometry.

Histological Sections and Cytospins

Immediately following sacrifice of animals tissues were rinsed in PBS and fixed for 24 hours in buffered formalin before being given off to the Sunnybrook Research Institute Histology facility for paraffin embedding, slicing and staining with hematoxylin and eosin. Bone tissues were decalcified following fixation before further processing. Cytospins were prepared by centrifuging single celled suspensions onto glass slides using a Shandon cytocentrifuge. Cytospins were air dried, and fixed in methanol before staining with May-Gruwald and Giemsa stains. Cytospins were coverslipped following treatment with a toluene-based synthetic resin mounting medium.

Peripheral Blood Counts:

Bone marrow transplant recipients that received grafts containing 100% transduced bone marrow cells were bleed at 4 weeks post-transplant from the Saphenous vein. Alternatively, moribund animals were bled by cardiac puncture just prior to death. To give matched data, a GFP control animal was analysed with every NR2F6 moribund animal analysed. Blood was collected using a heparinized capillary tube and taken to the Toronto Centre for Phenogenomics for acquisition of haematological parameters on a Hemavet analyser.

Analysis of Hematopoietic Stem Cell Subsets:

Bone marrow transplant recipients that received grafts containing 100% transduced bone marrow cells were humanely sacrificed at four weeks post-transplant. Red blood cells were lysed and bone marrow washed two times with PBS. Bone marrow cells were then stained with biotin CD3, biotin CD45R/B220 (RA3-6B2), biotin CD11b (M1/70), biotin erythroid marker (TER-119), biotin Ly-6G (RB6-8C5), c-kit APC, sca-1 PE-Cy7 and either CD34 PE or CD49b PE (all eBioscience) in the dark. Bone marrow was washed once and incubated with streptavidin PE-Cy5 for 20 minutes in the dark. Bone marrow was washed twice and analysed using flow cytometry on a Becton Dickinson LSR II. All samples analysed were gated based on FSC/SSC and GFP+ cells. The population of lineage$^-$ Sca-1$^+$ c-kit$^+$ (LSK) is highly enriched for hematopoietic stem cell activity. This population was analysed and further subdivided based on the expression of the CD34 and CD49b antigen. Whereas the CD34$^{-/low}$ and the CD49b$^{-/low}$ population of LSK cells are enriched for long-term hematopoietic stem cells, the CD34$^+$ and CD49b+ population of LSK cells are composed of short term hematopoietic stem cells.

Results

To assess the pattern of expression of NR2F6 in normal hematopoiesis and we used Q-PCR to measure expression of NR2F6 transcripts in a graded series of pluripotent, multipotent, oligopotent, and unipotent murine haematopoietic cells (cDNAs were a kind gift from Dr. Norman Iscove). NR2F6 transcripts were most abundant in long-term hematopoietic stem cells and became progressively less abundant with differentiation, with the exception of committed megakaryocyte progenitors, in which expression was high (FIG. 1A). These observations are consistent with NR2F6 having a role in the maintenance of the undifferentiated state of primitive hematopoietic cells. Expression of NR2F6 mRNA is shown relative to GAPDH. Long-term repopulating HSCs (LT-HSC), short-term repopulating HSCs (ST-HSC), pentapotent progenitor (Penta), committed non-lymphoid progenitor (E Meg Mac), erythroid/megakaryocyte progenitor (E Meg), committed megakaryocyte progenitor (Meg Pro), BFU-E, CFU-E, megakaryocyte (Meg). All expression levels are relative to expression of NR2F6 in E Meg Mac.

Figure 1B:
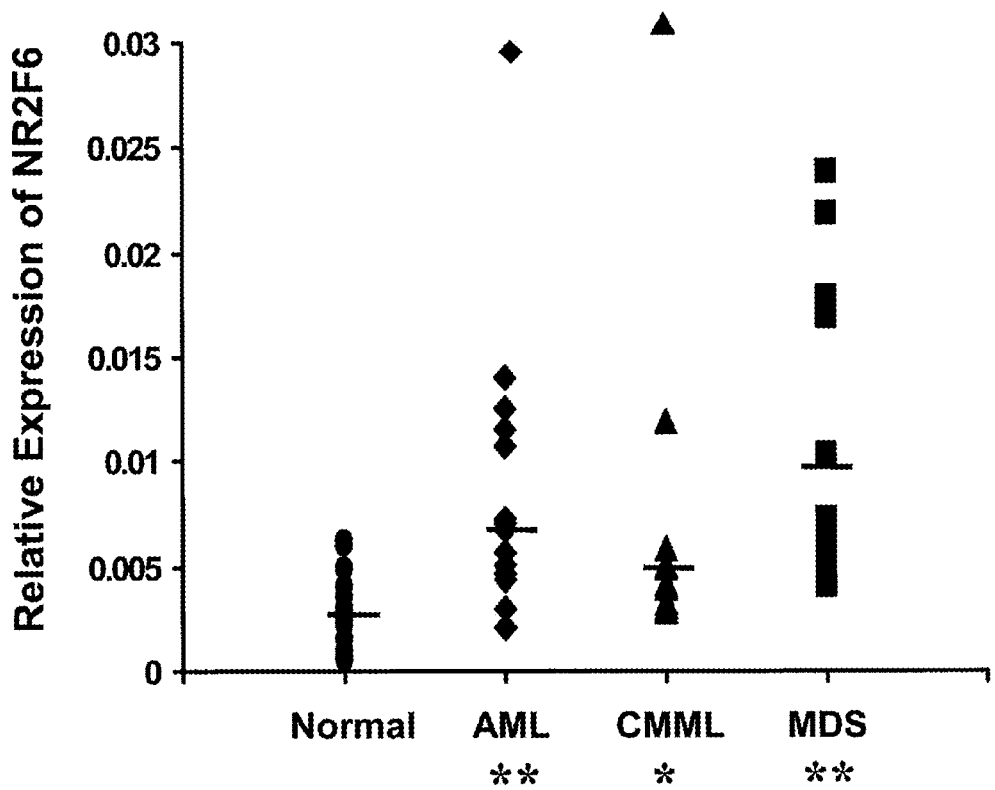

Bone marrow from patients with acute myelogenous leukemia (AML), chronic myelomonocytic leukemia (CMML) and myelodysplastic syndrome (MDS) have greater expression of NR2F6 mRNA than bone marrow from healthy human controls (FIG. 1B). These data support the notion that NR2F6 may be used as a biomarker for the diagnosis and/or prognosis of patients with leukemia, CMML and MDS.

Figure 2:
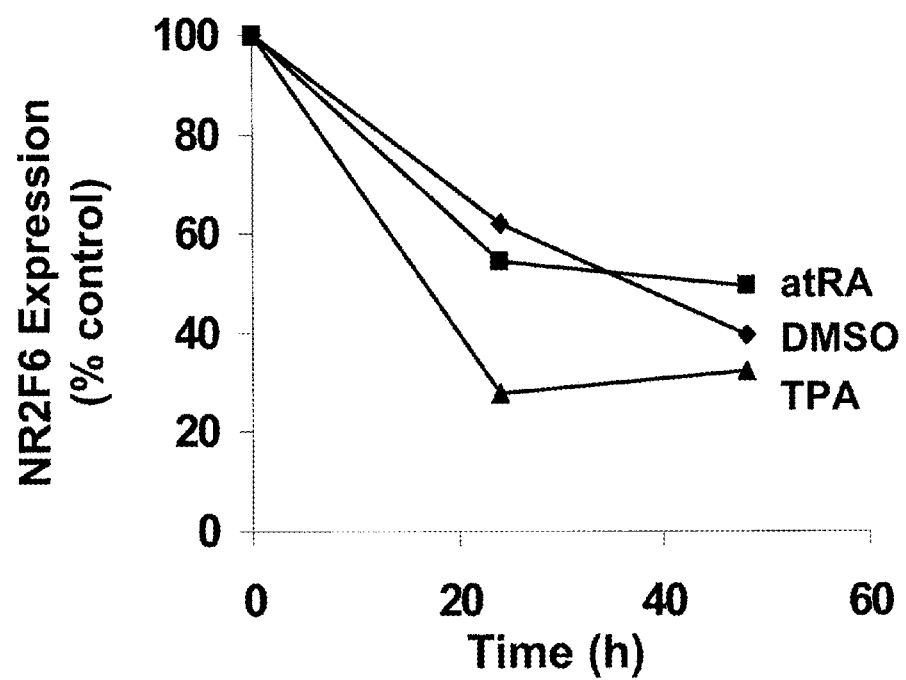
FIG. 2 shows NR2F6 mRNA is expressed highly in immature U937 human leukemia cell line.

NR2F6 mRNA is expressed highly in immature U937 human leukemia cell line (FIG. 2). The high expression of NR2F6 is associated with maintenance of the undifferentiated state of these cells. Induction of U937 leukemia cells to differentiate and to acquire characteristics of mature blood cells was associated with a sharp decrement in the expression of NR2F6 mRNA. The rapid decrease in NR2F6 mRNA expression is a general response to the induction of differentiation and maturation since this decrease occurred irrespective of the agent used to induce differentiation and maturation.

Figure 3A:
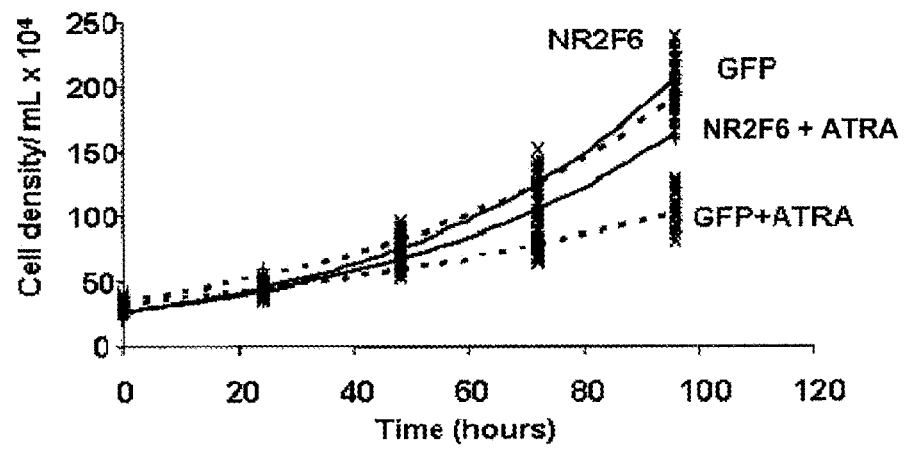
FIGS. 3A and 3B show overexpression of NR2F6 is able to override the growth arrest associated with differentiation and maturation, in particular maturation and differentiation induced by all-trans retinoic acid.
Figure 3B:
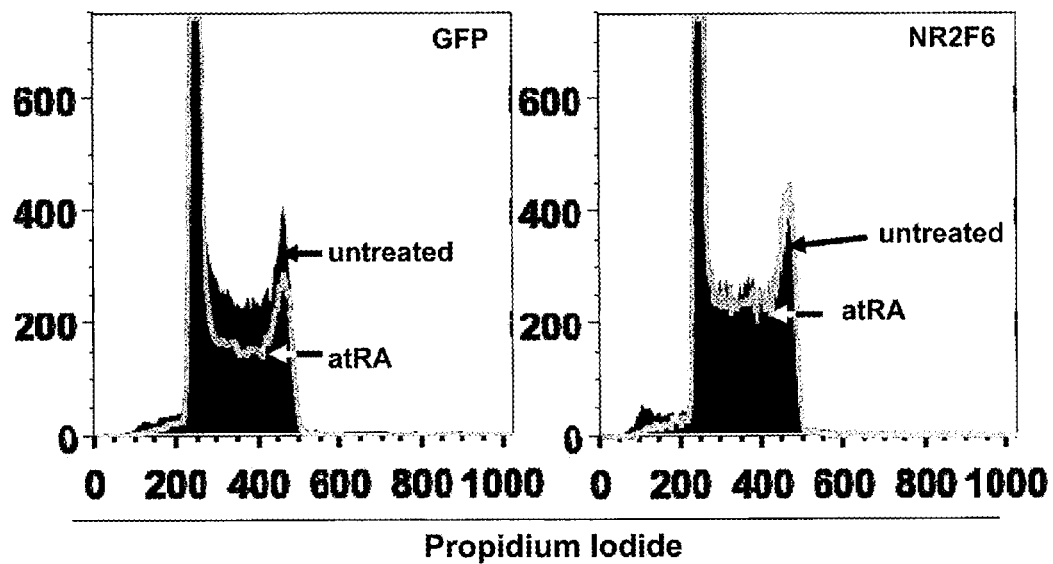

Overexpression of NR2F6 is able to override the growth arrest associated with differentiation and maturation, in particular maturation and differentiation induced by all-trans retinoic acid (FIG. 3). This suggests that NR2F6 can act to antagonize the initiation of the downstream pathways that are activated by all-trans retinoic acid (atRA). Growth of U937 cells expressing either GFP of NR2F6-IRES-GFP was monitored by counting using trypan blue following treatment of cells with atRA (FIG. 3A). U937 cells expressing either GFP of NR2F6-IRES-GFP were treated with atRA. DNA content was assessed using propidium iodide in order to determine which phase of the cell cycle the cells in each respective population resided in (FIG. 3B). Control U937 GFP cells showed a drastic decrease in the number of cells in S/G2/M phases of the cell cycle following treatment with atRA, however U937 cells that over-expressed NR2F6 did not show any decrease in the number of cells in S/G2/M phases of the cell cycle following treatment with atRA. These data suggest the NR2F6 over-expression promotes proliferation by affecting the cell cycle.

Figure 4:
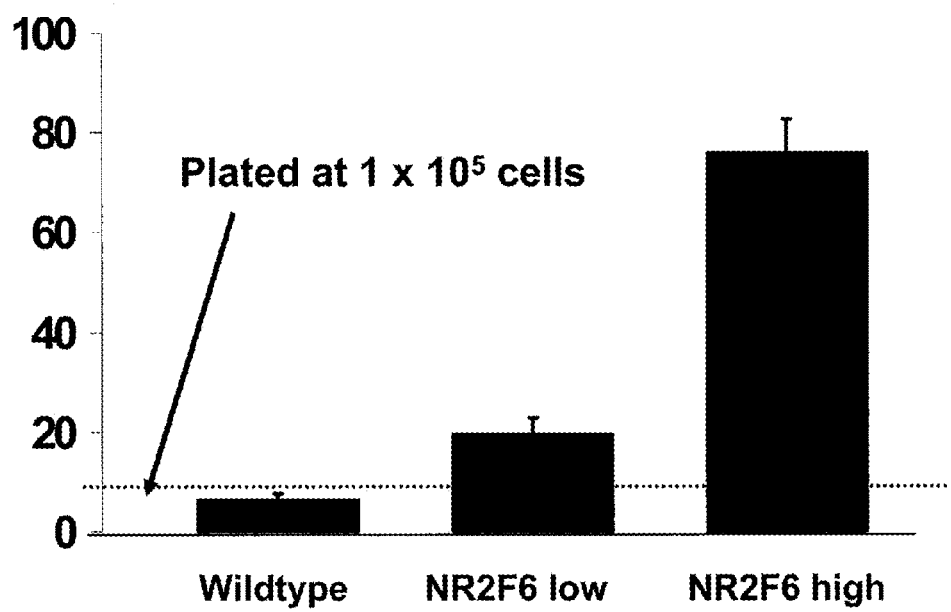
FIG. 4 shows over-expression of NR2F6 enables the survival and proliferation of mouse embryonic fibroblasts (MEFs) in low serum (0.2% serum).

Over-expression of NR2F6 enables the survival and proliferation of mouse embryonic fibroblasts (MEFs) in low serum (0.2% serum) (FIG. 4). MEFs were stably transduced using a retroviral construct containing either GFP of NR2F6-IRES-GFP. MEFs transduced with NR2F6 were sorted into high transgene expressers or low transgene expressers based on GFP intensity. Cells were initially plated at $1 \times 10^5$ cells and enumerated after several days.

Figure 5A:
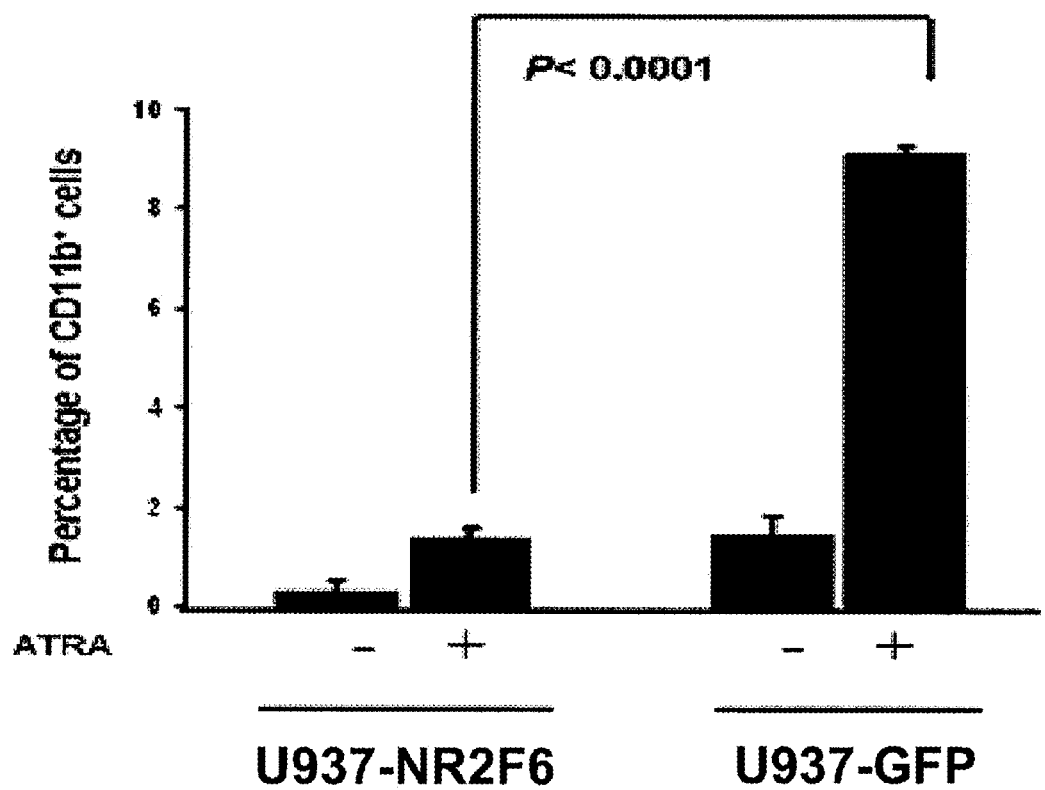
FIGS. 5A and 5B show over-expression of NR2F6 is able to inhibit the differentiation and maturation of U937 human leukemia cells.
Figure 5B:
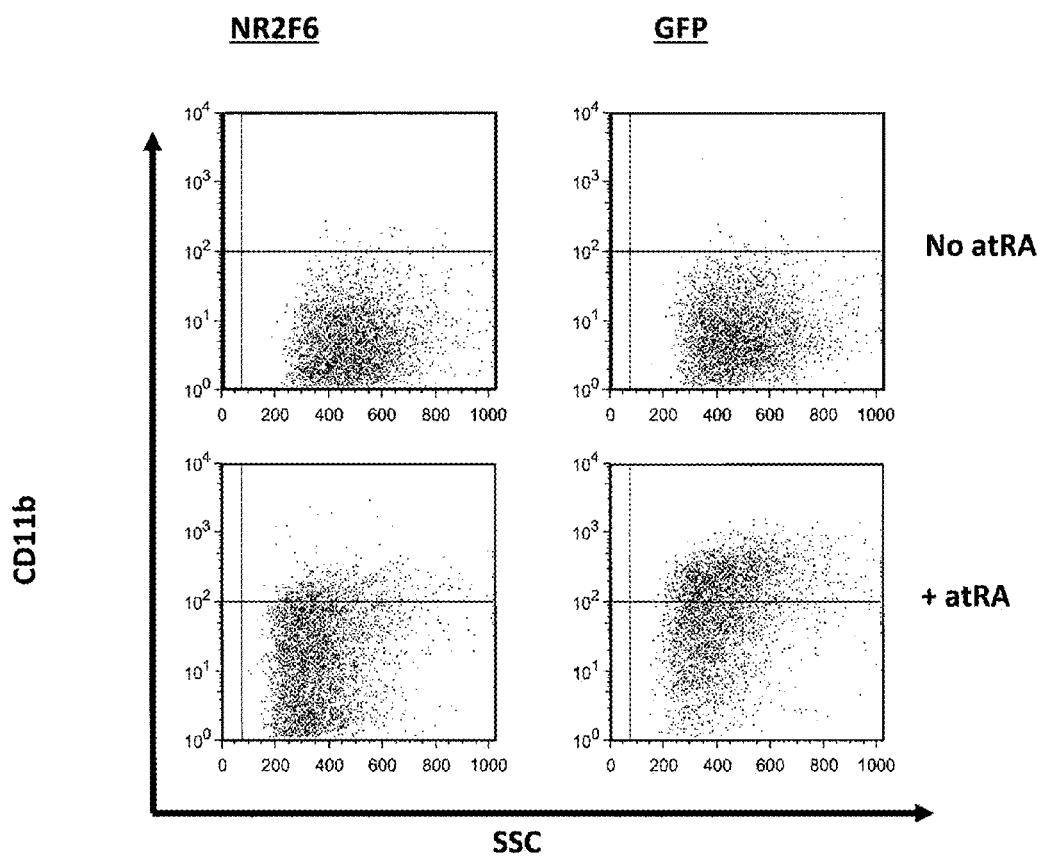

Over-expression of NR2F6 is able to inhibit the differentiation and maturation of U937 human leukemia cells (FIG. 5). U937 cells expressing either GFP of NR2F6-IRES-GFP were treated with atRA and assessed for maturation. Following induction of differentiation with atRA expression of the myeloid maturation marker CD11b was assessed using flow cytometry. These data suggest that aberrant expression of NR2F6 inhibits the maturation of leukemia cells, in particular toward the myeloid cell lineage.

Figure 6A:
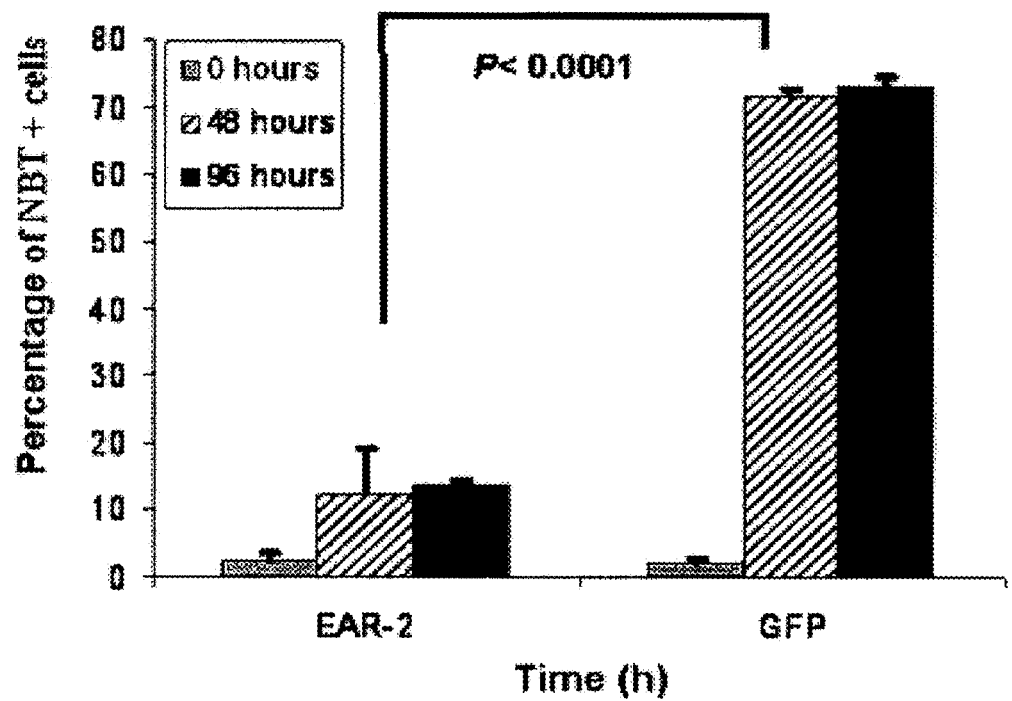
FIGS. 6A and 6B show over-expression of NR2F6 is able to inhibit the differentiation and maturation of U937 human leukemia cells.
Figure 6B:
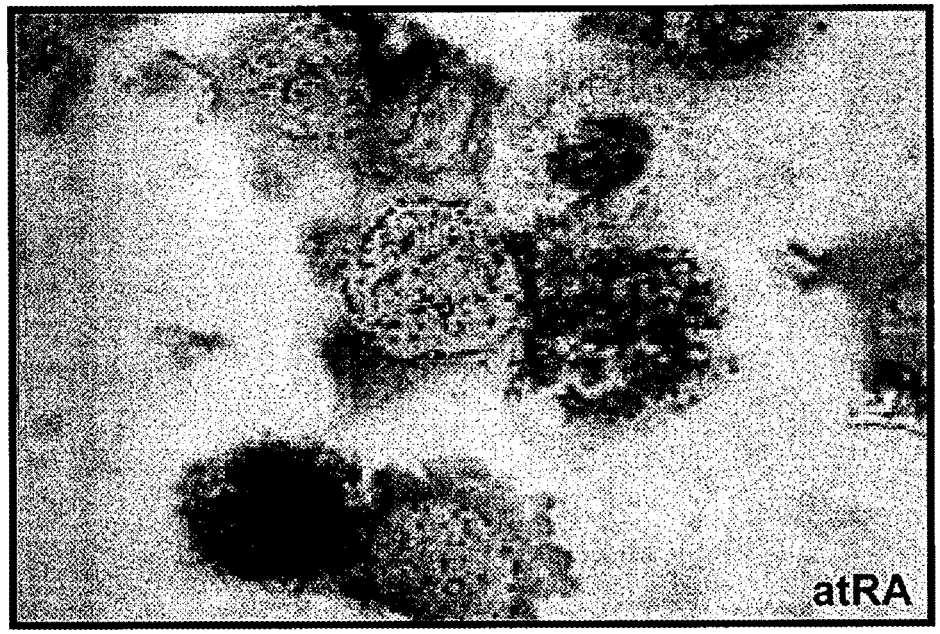
Figure 6B:
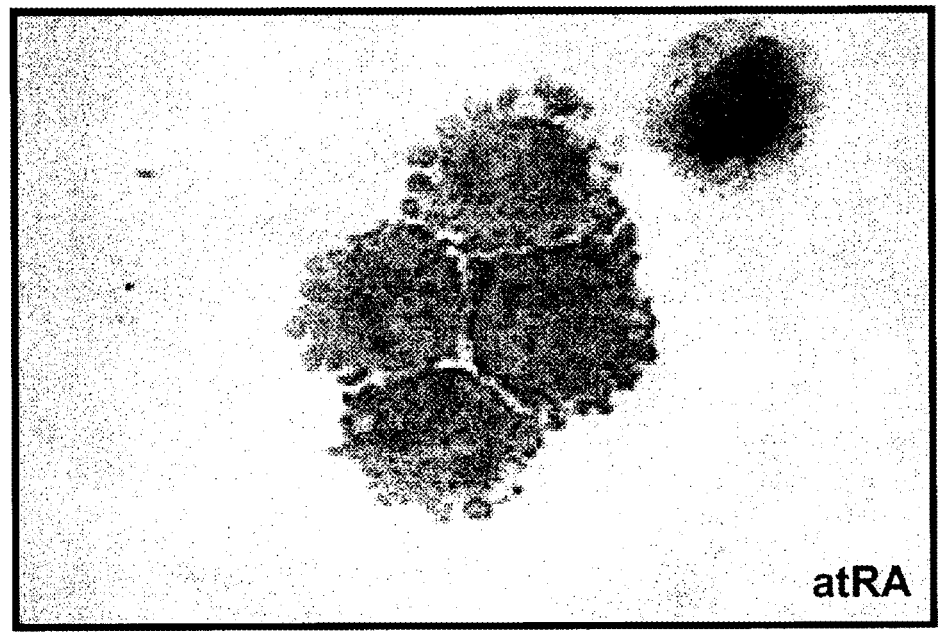

Over-expression of NR2F6 is able to inhibit the differentiation and maturation of U937 human leukemia cells (FIG. 6). U937 cells expressing either GFP of NR2F6-IRES-GFP were treated with atRA and assessed for maturation. Following induction of differentiation with atRA cells were stained for nitroblue tetrazolium (NBT). The percentage of NBT+ cells were enumerated in three separate fields of view in which more than 100 individual cells were evaluated (FIG. 6A). A microphotograph of representative U937-NR2F6 and U937-GFP cells is shown in FIG. 6B. These data suggest that aberrant expression of NR2F6 inhibits the maturation of leukemia cells, in particular toward the myeloid cell lineage.

Figure 7A:
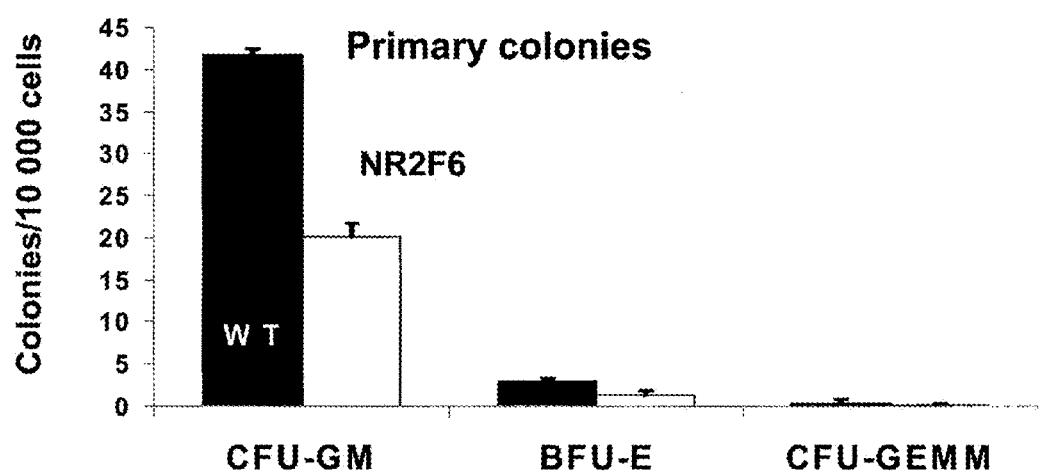
FIGS. 7A, 7B, and 7C show NR2F6 over-expression inhibits the maturation of healthy bone marrow.
Figure 7B:
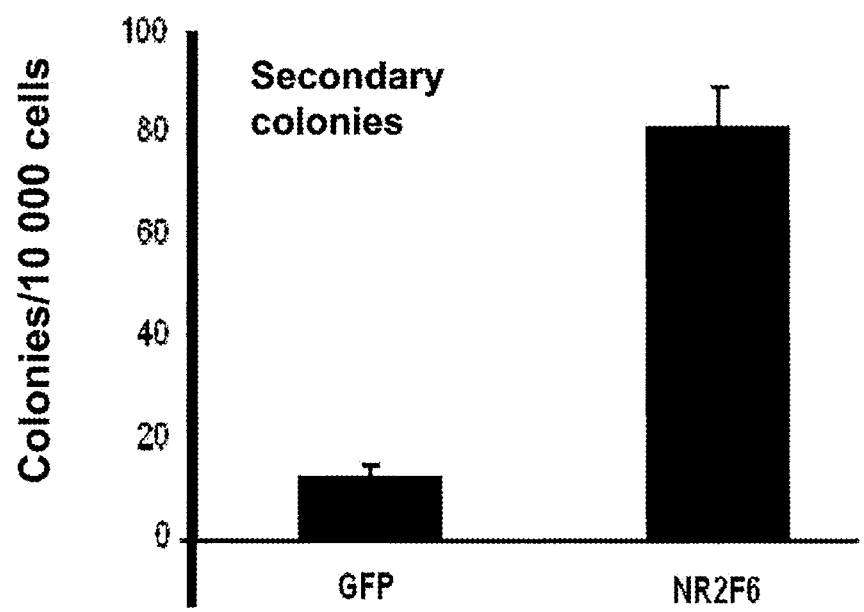
Figure 7C:
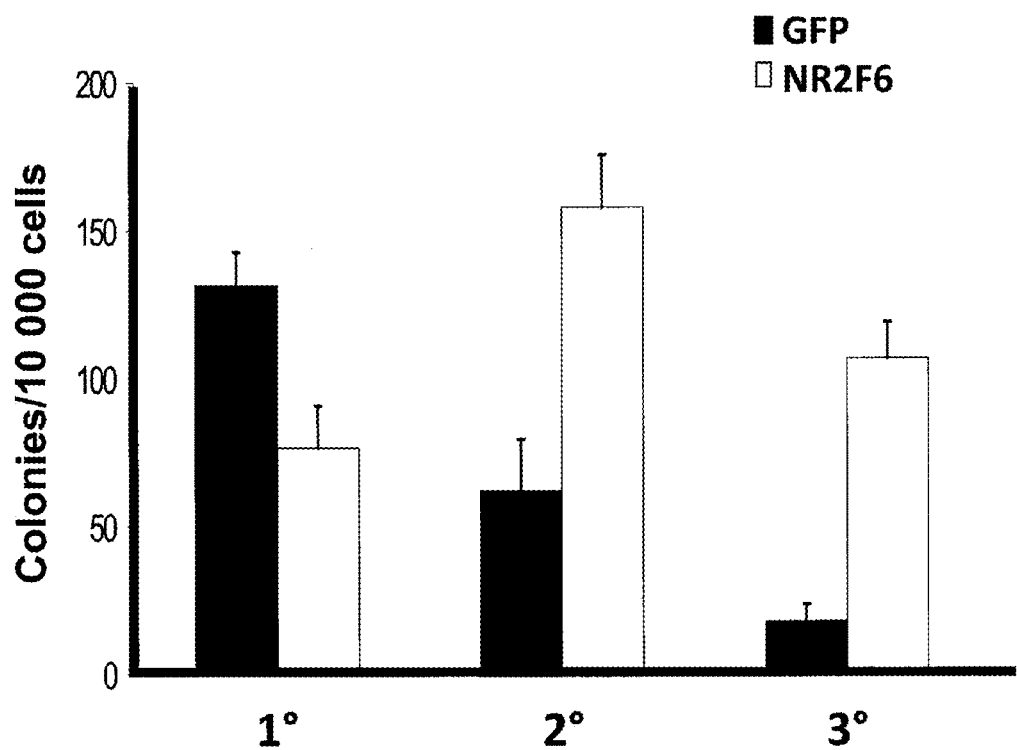

NR2F6 over-expression inhibits the maturation of healthy bone marrow (FIG. 7). Bone marrow from 5-FU treated C57BI/6 mice was transduced using a retrovirus containing either GFP of NR2F6-IRES-GFP. Transduced cells (GFP+) were sorted and plated in methylcellulose culture containing growth factors that would support multi-lineage differentiation. Colonies were enumerated after 12-14 days (FIG. 7A). These data are consistent with the over-expression of NR2F6 inhibiting maturation. After the enumeration of these primary colonies methycellulose cultures were harvested, washed with PBS and 10,000 of said cells were plated in another methycellulose culture to determine the ability of these cells to form colonies a second time, (FIG. 7B), and then repeated yet a third time (FIG. 7C). These secondary and tertiary cultures were enumerated after another 12-14 days of culture. The ability of bone marrow that over-expresses NR2F6 to form a far greater number of secondary and tertiary colonies compared to control bone marrow demonstrates that over-expression of NR2F6 inhibits terminal differentiation of hematopoietic cells.

Figure 8A:
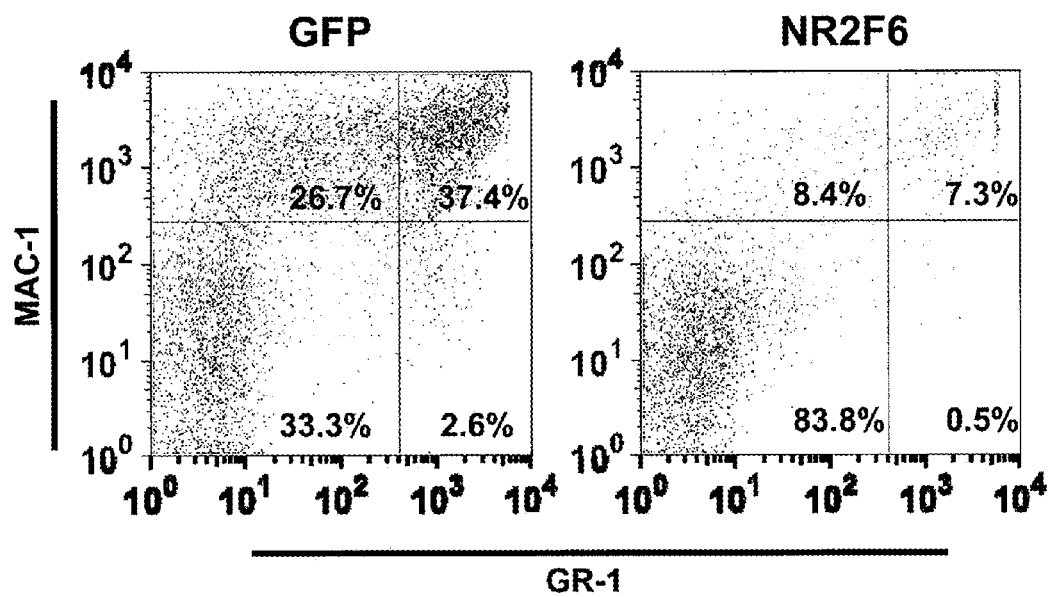
FIGS. 8A and 8B show NR2F6 over-expression inhibits the maturation of healthy bone marrow toward the myeloid lineage.
Figure 8B:
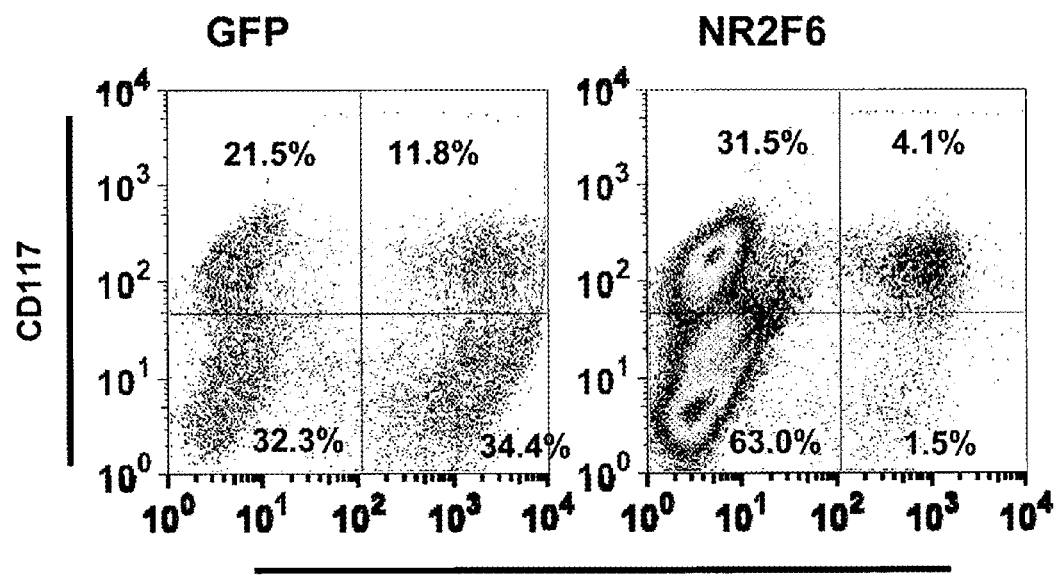

NR2F6 over-expression inhibits the maturation of healthy bone marrow toward the myeloid lineage (FIG. 8). Bone marrow from 5-FU treated C57BI/6 mice was transduced using a retrovirus containing either GFP of NR2F6-IRES-GFP and cells were plated in IMDM liquid medium containing growth factors that support multi-lineage differentiation. The percentage of myeloid cells following ten days of culture was assessed by flow cytometry using the cell surface markers Mac1/CD11b and Gr-1 (FIG. 8A). The graphs in the panel have been gated on the transduced cells (GFP+). The percentage of mast cells was also determined following ten days of culture using flow cytometry for the cell surface marker c-kit (FIG. 8B). The graphs in the panel have not been gated a priori on the transduced cells (GFP+).

Figure 9A:
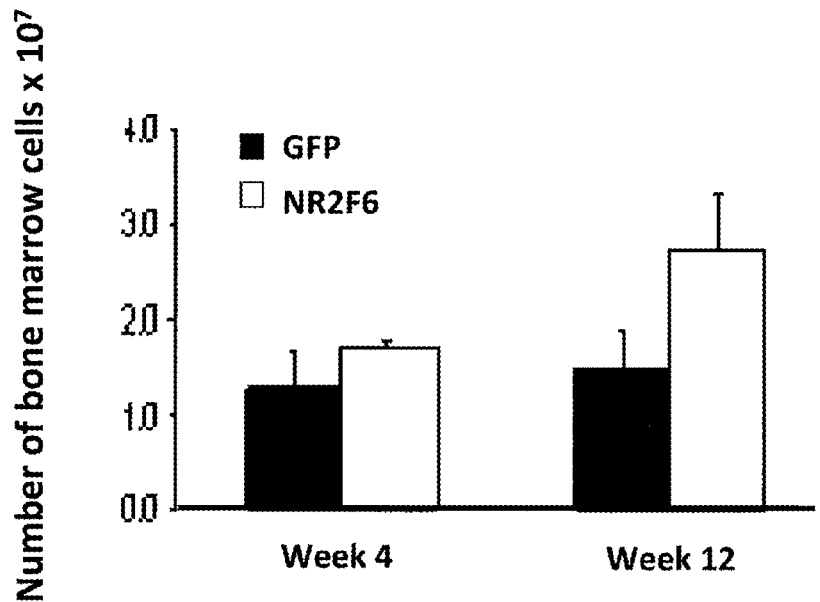
FIGS. 9A, 9B, and 9C show NR2F6 over-expression in vivo increases bone marrow cellularity, even when only a portion of the cells over-express NR2F6.
Figure 9B:
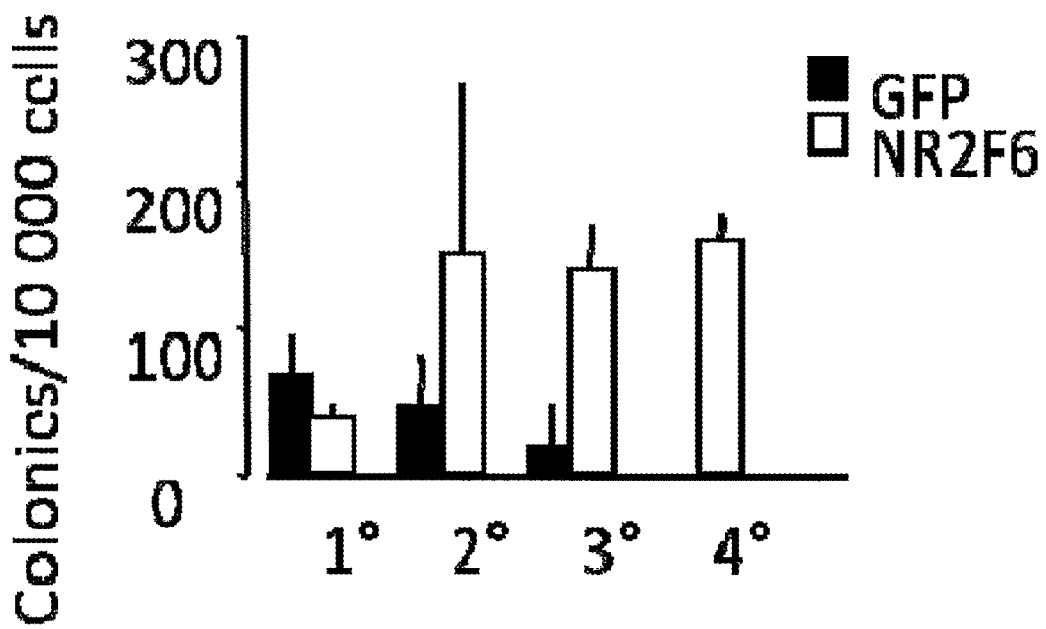
Figure 9C:
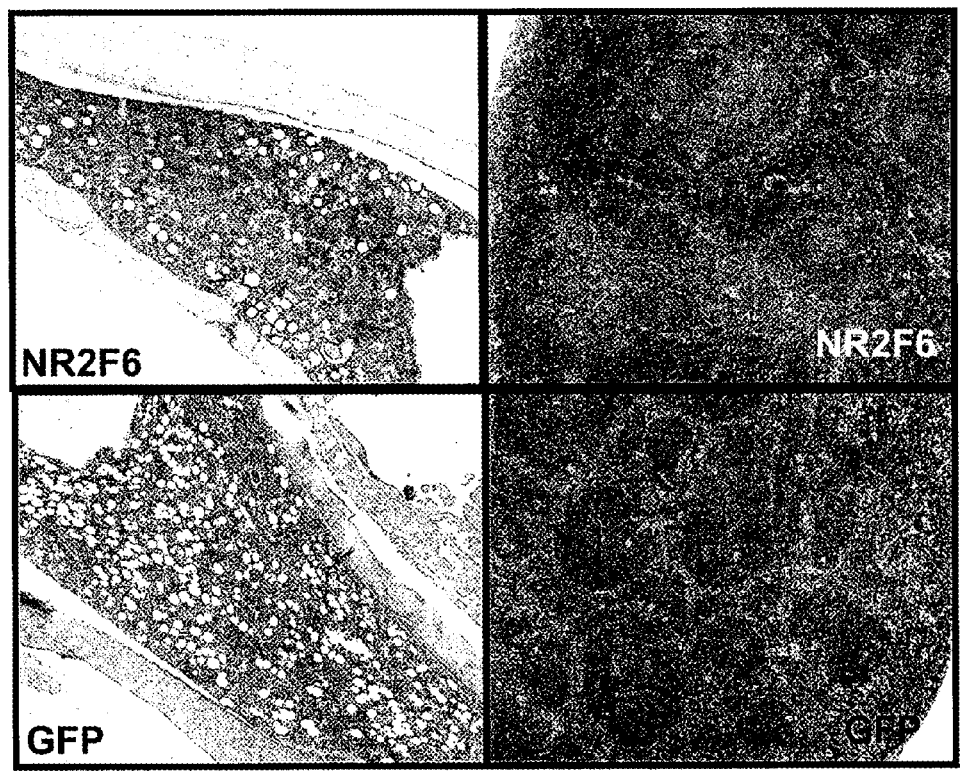

NR2F6 over-expression in vivo increases bone marrow cellularity, even when only a portion of the cells over-express NR2F6 (FIG. 9). Chimerical mice that overexpressed NR2F6 in only a portion of their bone marrow cells were generated by transducing bone marrow from 5-FU treated C57BI/6 using a retrovirus containing either GFP of NR2F6-IRES-GFP. Cells were then sorted and admixed with a fixed ratio of wild-type bone marrow before transplantation into lethally irradiated C57BI/6 hosts. Animals were harvested to monitor short-term (4 week) as well as long-term (12 week) hematopoietic effects. Over-expression of NR2F6 in the bone marrow of animals resulted in hypercellular bone marrow as determined by counting cells with trypan blue after flushing two femurs and one tibia (FIG. 9A). Furthermore, NR2F6-transduced cells from BMT recipients had a striking increase in replating ability relative to GFP-transduced cells (FIG. 9B) Histological sections that were stained with hematoxylin and eosin stain demonstrate that over-expression of NR2F6 causes bone marrow to become hypercellular (FIG. 9C). Mice also had splenomegaly, this is consistent with histological sections that show alterations in the splenic architecture, consistent with an expansion of the proliferative centers of the white pulp.

Figure 10:
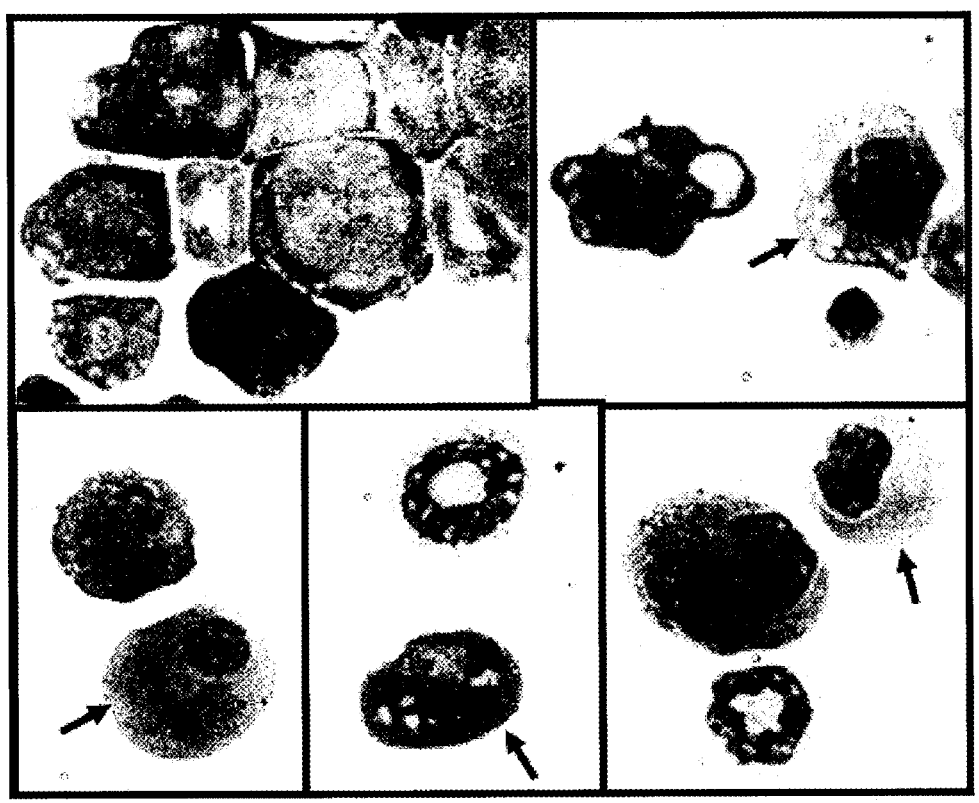
FIG. 10 shows NR2F6 over-expression causes bone marrow dysplasia.

NR2F6 over-expression causes bone marrow dysplasia (FIG. 10). Chimerical mice that overexpressed NR2F6 in only a portion of their bone marrow cells were generated by transducing bone marrow from 5-FU treated C57BI/6 using a retrovirus containing either GFP of NR2F6-IRES-GFP. Cells were then sorted and admixed with a fixed ratio of wild-type bone marrow before transplantation into lethally irradiated C57BI/6 hosts. Examination of bone marrow cytospins from these animals shows dysplastic characteristics, especially in the erythroid lineage. This dysplasia resemble morphologically the dysplasia observed in human patients with myelodysplastic syndrome, suggesting that modulation of NR2F6 could provide a therapeutic benefit to these patients.

Figure 11:
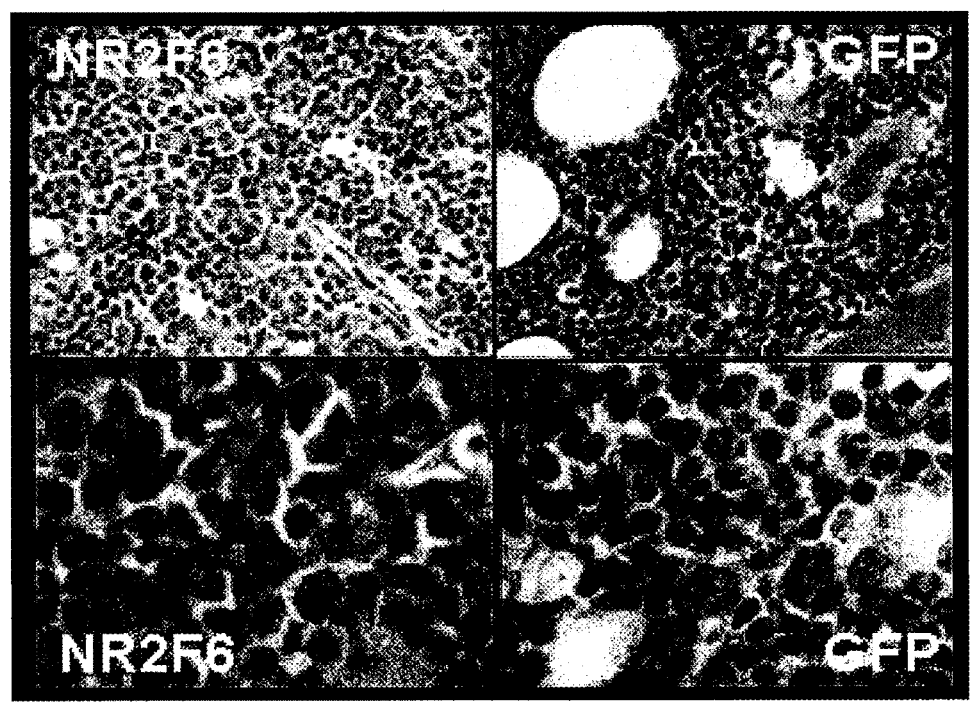
FIG. 11 shows NR2F6 over-expression causes abnormal localization of immature precursors (ALIP).

NR2F6 over-expression causes abnormal localization of immature precursors (ALIP) (FIG. 11). Chimerical mice that overexpressed NR2F6 in only a portion of their bone marrow cells were generated by transducing bone marrow from 5-FU treated C57BI/6 using a retrovirus containing either GFP of NR2F6-IRES-GFP. Cells were then sorted and admixed with a fixed ratio of wild-type bone marrow before transplantation into lethally irradiated C57BI/6 hosts. Examination of bone marrow histological sections from these cohorts of animals shows that over-expression of NR2F6 results in the phenomenon of abnormal localization of immature precursors (ALIP). This resembles the condition ALIP which is observed in human patients with high risk myelodysplastic syndrome, again suggesting that modulation of NR2F6 could provide a therapeutic benefit to these patients.

Figure 12:
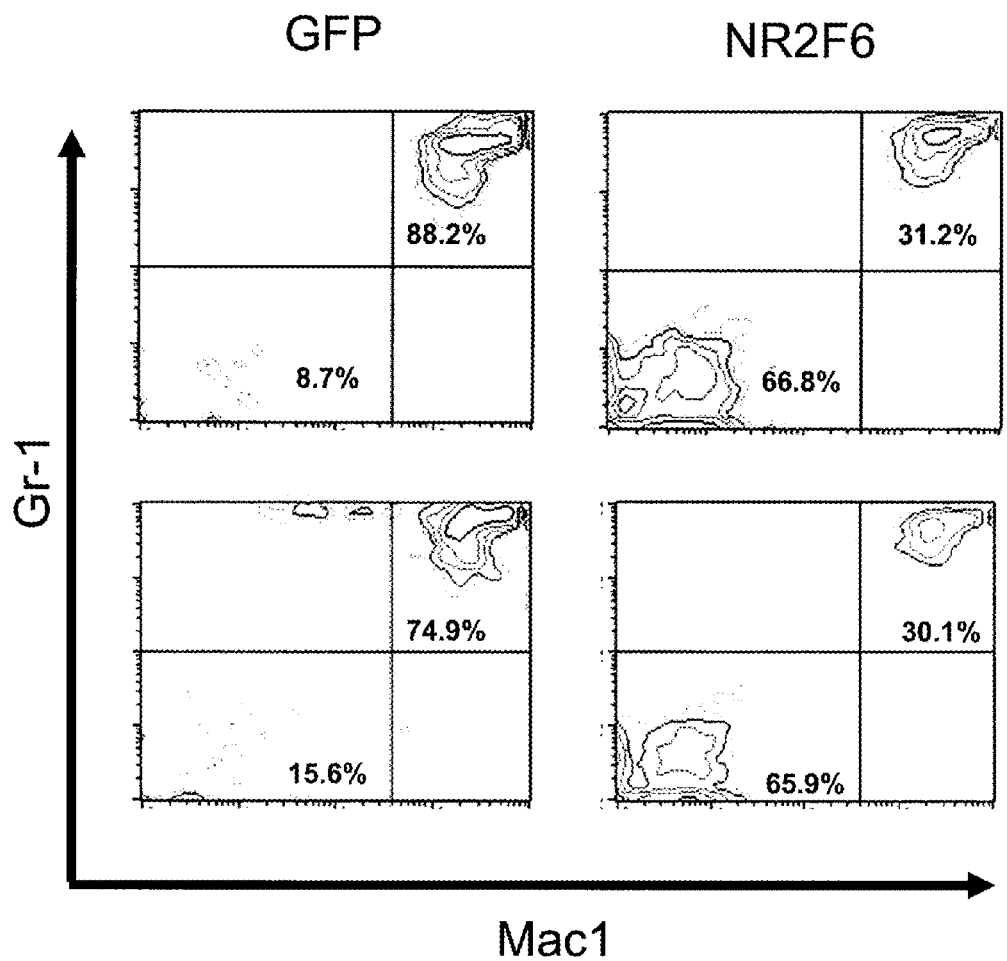
FIG. 12 shows NR2F6 over-expression inhibits myeloid differentiation and maturation in vivo.
Figure 13A:
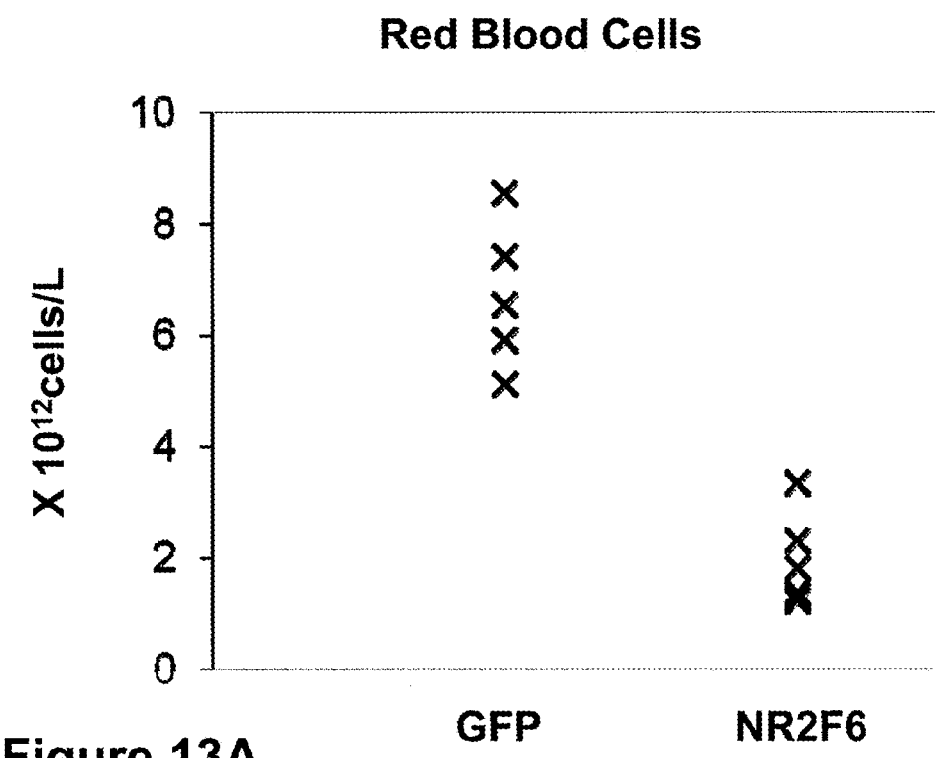
FIGS. 13A, B, C, and D show NR2F6 over-expression inhibits blood cell differentiation and maturation in vivo.
Figure 13B:
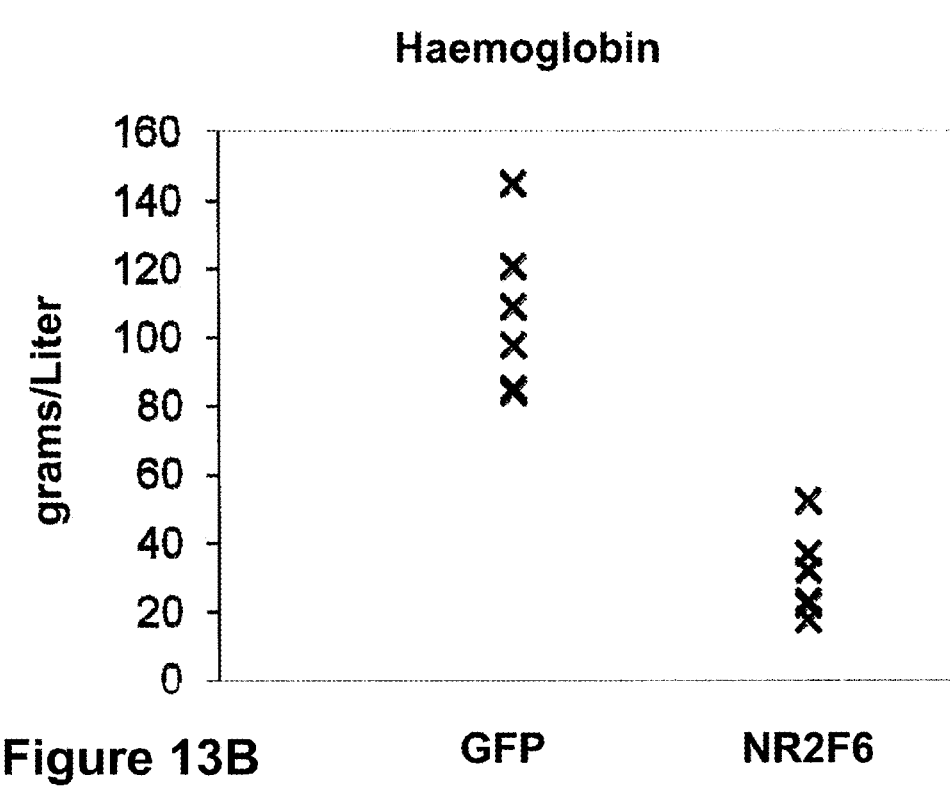
Figure 13C:
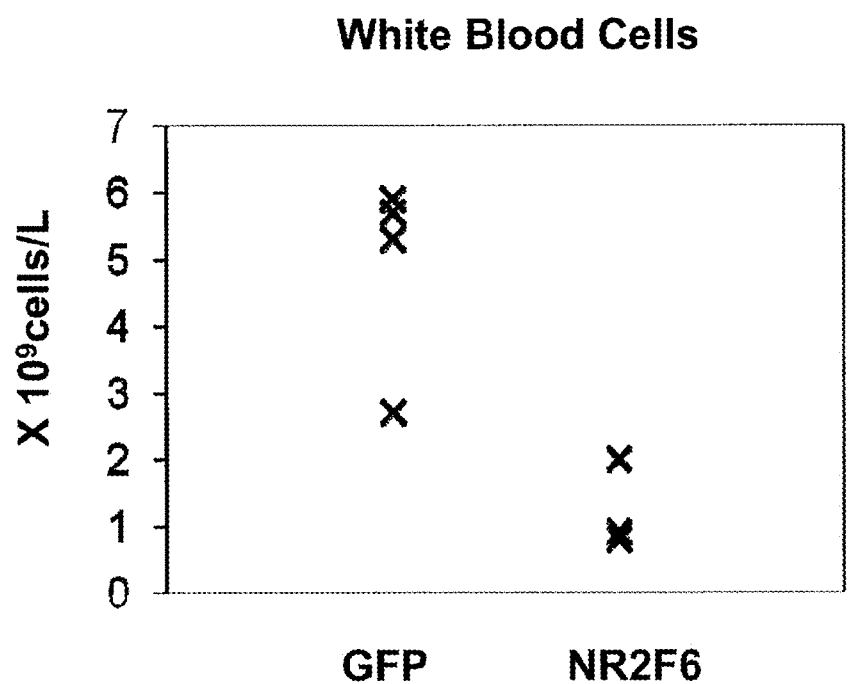
Figure 13D:
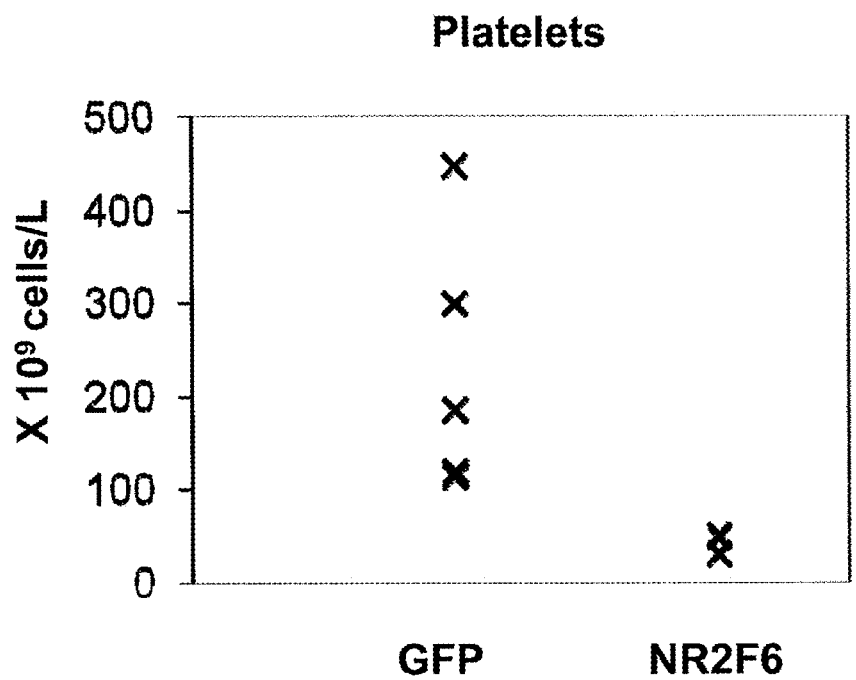

NR2F6 over-expression inhibits myeloid differentiation and maturation in vivo (FIG. 12). Chimerical mice that over-expressed NR2F6 in only a portion of their bone marrow cells were generated by transducing bone marrow from 5-FU treated C57BI/6 using a retrovirus containing either GFP of NR2F6-IRES-GFP. Cells were then sorted and admixed with a fixed ratio of wild-type bone marrow before transplantation into lethally irradiated C57BI/6 hosts. Analysis of the bone marrow of these mice by flow cytometry showed that over-expression of NR2F6 prevents the differentiation and maturation of progenitor cells into neutrophils (Mac1+/Gr-1+). This data suggests that modulation of NR2F6 could provide a therapeutic benefit to patients suffering from disorders associated with abnormal myeloid maturation.

NR2F6 over-expression inhibits blood cell differentiation and maturation in vivo (FIG. 13). Mice that over-expressed NR2F6 in all of their bone marrow cells were generated by transducing bone marrow from 5-FU treated C57BI/6 using a retrovirus containing either GFP of NR2F6-IRES-GFP. Cells were then sorted and transplantation into lethally irradiated C57BI/6 hosts. Analysis of the peripheral blood of these animals shows major defects in their ability to produce mature blood cells. At four weeks of age these animals are suffering from a condition similar to the human bone marrow failure syndromes. The test animals but not the controls are pancytopenic: they suffer from anemia, thrombocytopenia, and neutropenia. This data suggests that modulation of NR2F6 could provide a therapeutic benefit to patients suffering from disorders associated with abnormal blood cell differentiation and maturation.

Figure 14:
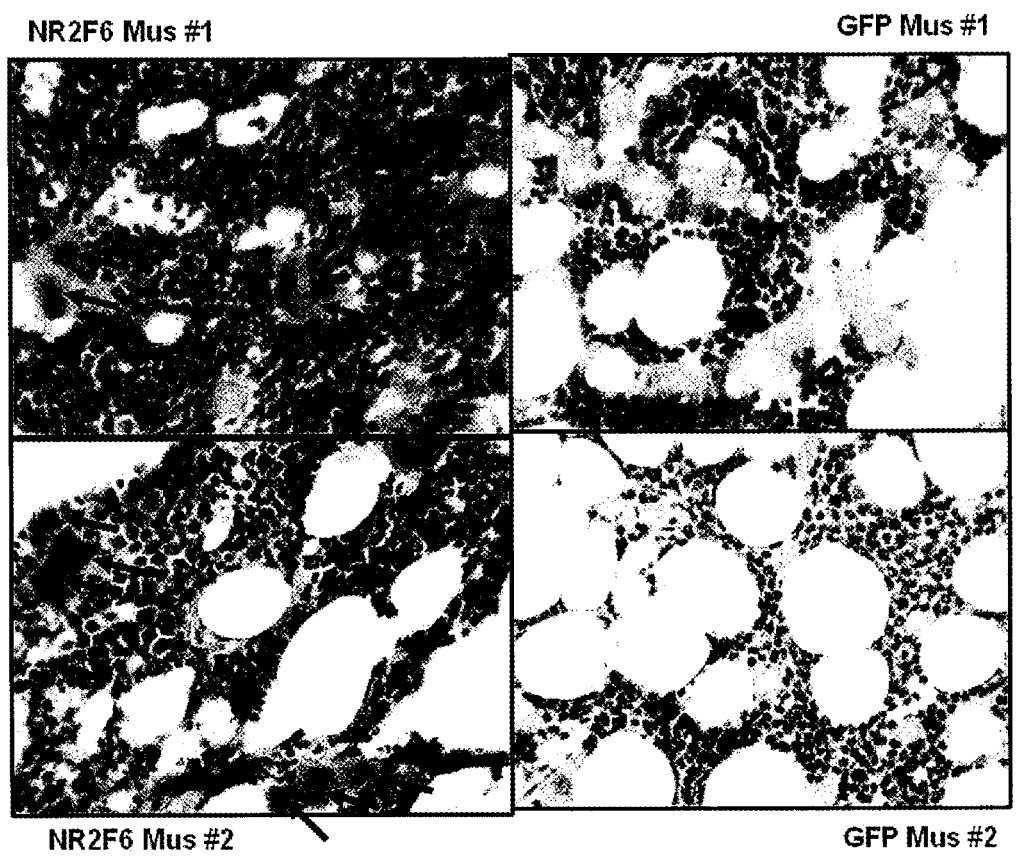
FIG. 14 shows NR2F6 over-expression produces an excess of megakaryoctes.

NR2F6 over-expression produces an excess of megakaryocytes (FIG. 14). Mice that over-expressed NR2F6 in all of their bone marrow cells were generated by transducing bone marrow from 5-FU treated C57BI/6 using a retrovirus containing either GFP of NR2F6-IRES-GFP. Cells were then sorted and transplantation into lethally irradiated C57BI/6 hosts. Despite the lower amounts of platelets observed at short term time points, analysis of the bone marrow of these animals revealed an excess of megakaryoctes. This suggests that modulation of NR2F6 at specific stages of blood cell development could provide a therapeutic benefit to patients suffering from thrombotic disorders, or disorders of megakaryocytic differentiation and maturation.

Figure 15:
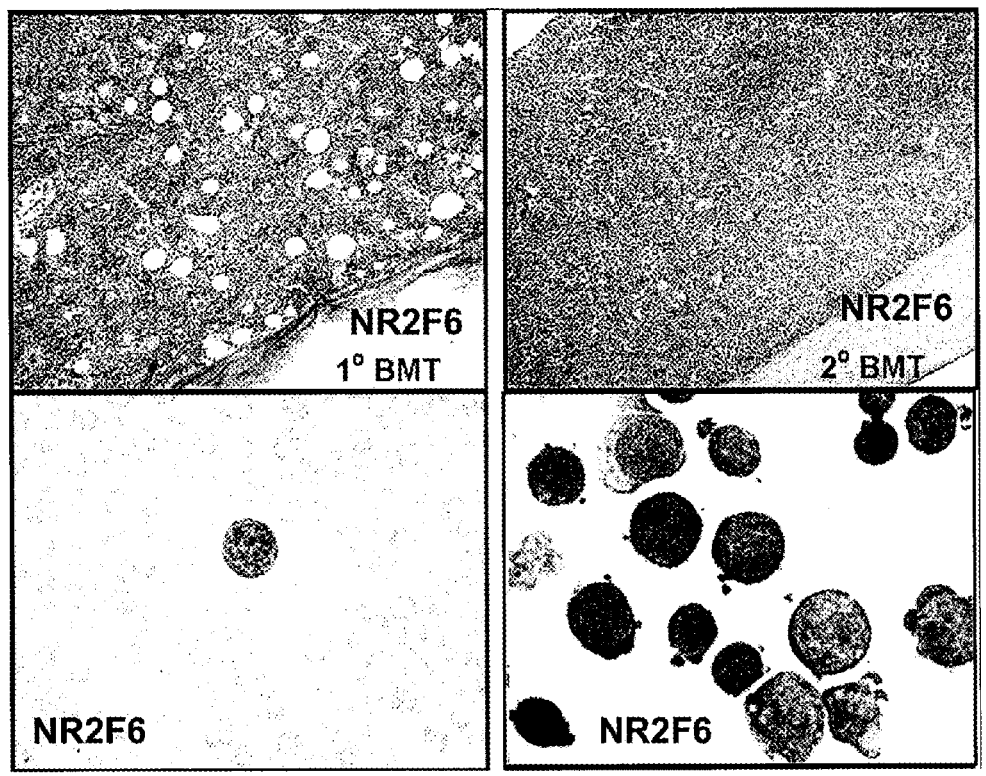
FIG. 15 shows NR2F6 over-expression, even in a small subset of bone marrow cells, eventually results in the generation of leukemia.

NR2F6 over-expression, even in a small subset of bone marrow cells, eventually results in the generation of leukemia (FIG. 15). Herein, a mouse model was used in which the phenotype was accelerated by conducting secondary transplants. Bone marrow from animals with NR2F6+ leukemia has a packed bone marrow cellularity. Animals with NR2F6+ leukemia also had immature blast cells in their peripheral blood. These are characteristics of high risk human leukemias and suggests that modulation of NR2F6 could provide a therapeutic benefit to patients suffering from leukemia or for preventing the development of leukemia in MDS patients.

Figure 16:
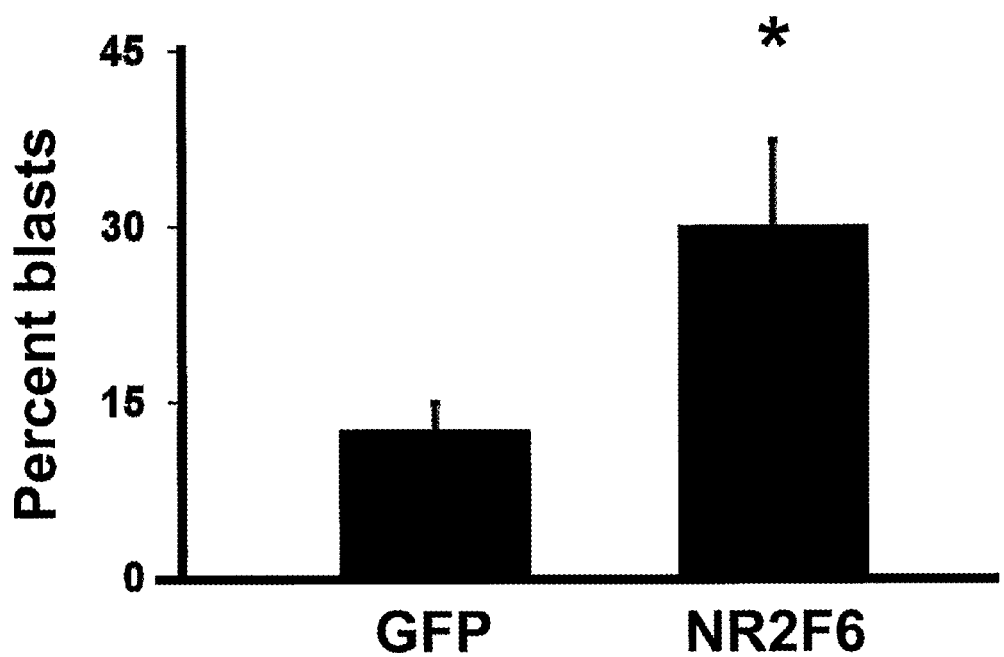
FIG. 16 shows NR2F6 over-expression, even in a small subset of bone marrow cells, results in the production of excessive immature blast cells.

NR2F6 over-expression, even in a small subset of bone marrow cells, results in the production of excessive immature blast cells (FIG. 16). Manual cell counts conducted on the cytospins of bone marrow from NR2F6 transplant chimera revealed an excess of blast cells and promyelocytic cells. Chimerical mice that over-expressed NR2F6 in only a portion of their bone marrow cells were generated by transducing bone marrow from 5-FU treated C57BI/6 using a retrovirus containing either GFP of NR2F6-IRES-GFP. Cells were then sorted and admixed with a fixed ratio of wild-type bone marrow before transplantation into lethally irradiated C57BI/6 hosts. An excess of immature blast cells is a characteristic of human leukemia. These data suggest that modulation of NR2F6 could provide a therapeutic benefit to patients suffering from leukemia or for preventing the development of leukemia in MDS patients.

Figure 17:
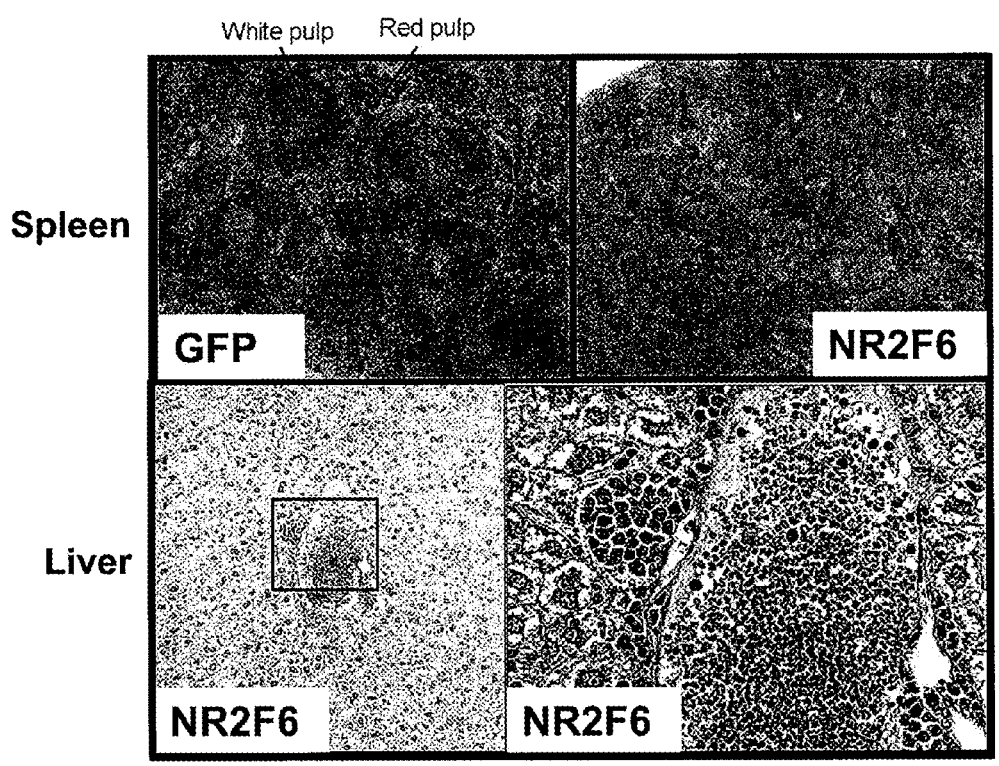
FIG. 17 shows NR2F6 over-expression, even in a small subset of bone marrow cells, eventually results in the generation of leukemia with infiltration of leukemia cells in the spleen and liver.

NR2F6 over-expression, even in a small subset of bone marrow cells, eventually results in the generation of leukemia (FIG. 17). Bone marrow from animals with NR2F6+ leukemia has a packed bone marrow cellularity. Histology from animals with NR2F6+ leukemia showed an utter obliteration of their splenic architecture. Leukemia cells also infiltrated the liver. Infiltration of organs is a characteristic of high risk human leukemia. These data suggest that modulation of NR2F6 could provide a therapeutic benefit to patients suffering from leukemia or for preventing the development of leukemia in MDS patients.

Figure 18A:
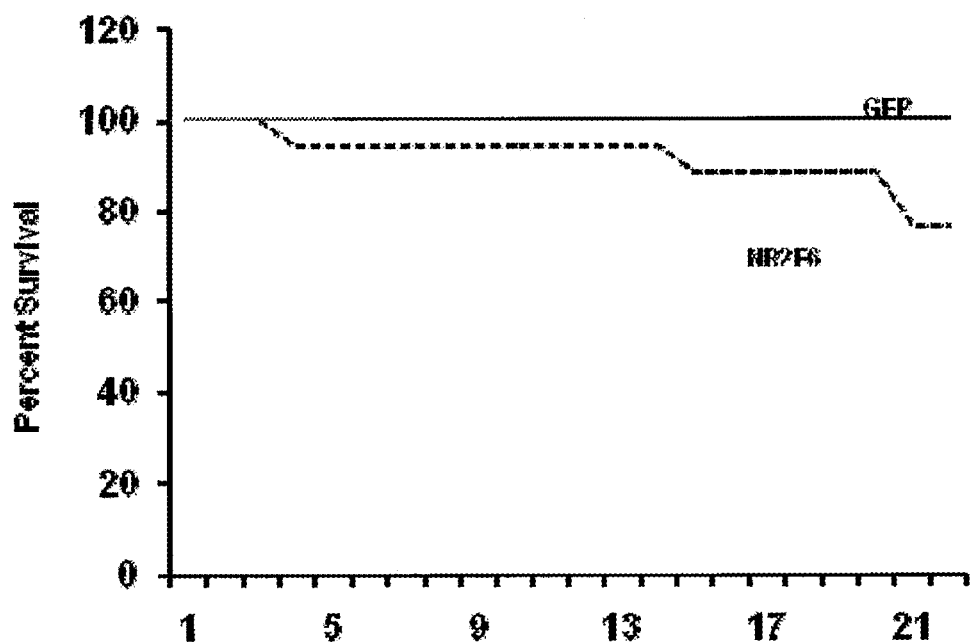
FIGS. 18A and 18B shows over-expression of NR2F6 in the bone marrow of healthy animals resulted in a fatal hematological condition that resembles human myelodysplastic syndrome and acute leukemia.
Figure 18B:
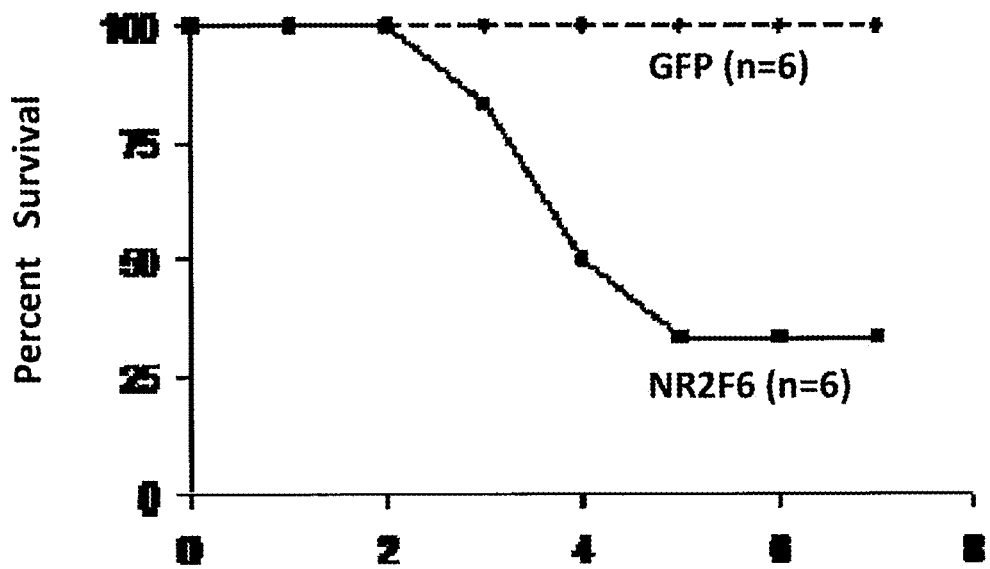

Over-expression of NR2F6 in the bone marrow of healthy animals resulted in a fatal hematological condition that resembles human myelodysplastic syndrome and acute leukemia (FIG. 18). NR2F6 over-expression in a small subset of bone marrow cells results in a prolonged hematological condition that eventually leads to death in a subset of its patients (FIG. 18A), while NR2F6 over-expression in all of one's bone marrow cells resulted in a rapidly fatal hematological condition (FIG. 18B). These data suggest that modulation of NR2F6 could provide a survival benefit to patients suffering from leukemia, MDS, or other hematological condition characterized by effacement of haematopoiesis.

Figure 19:
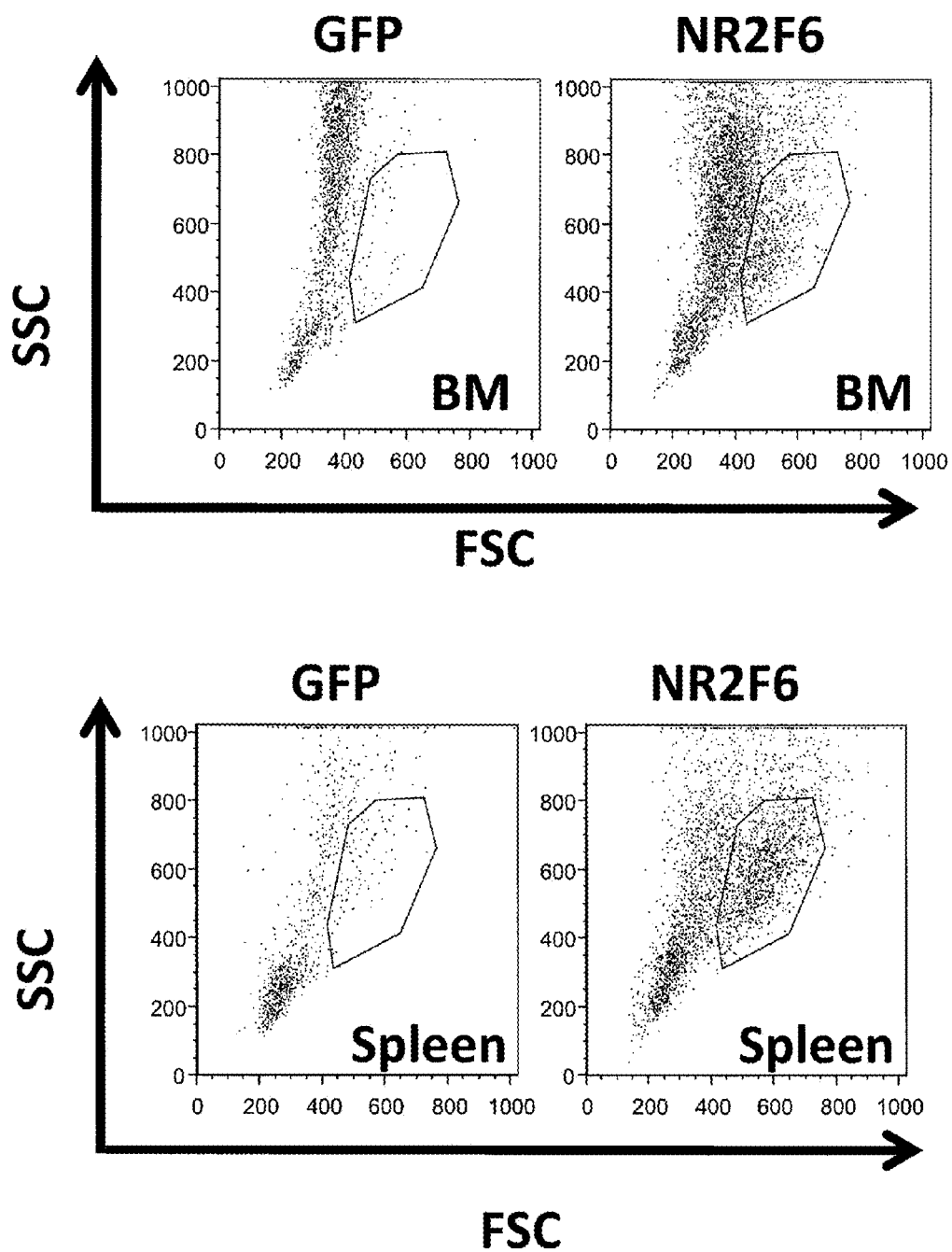
FIG. 19 shows that over-expression of NR2F6 in vivo causes expansion of immature bone marrow blast cells
Figure 20:
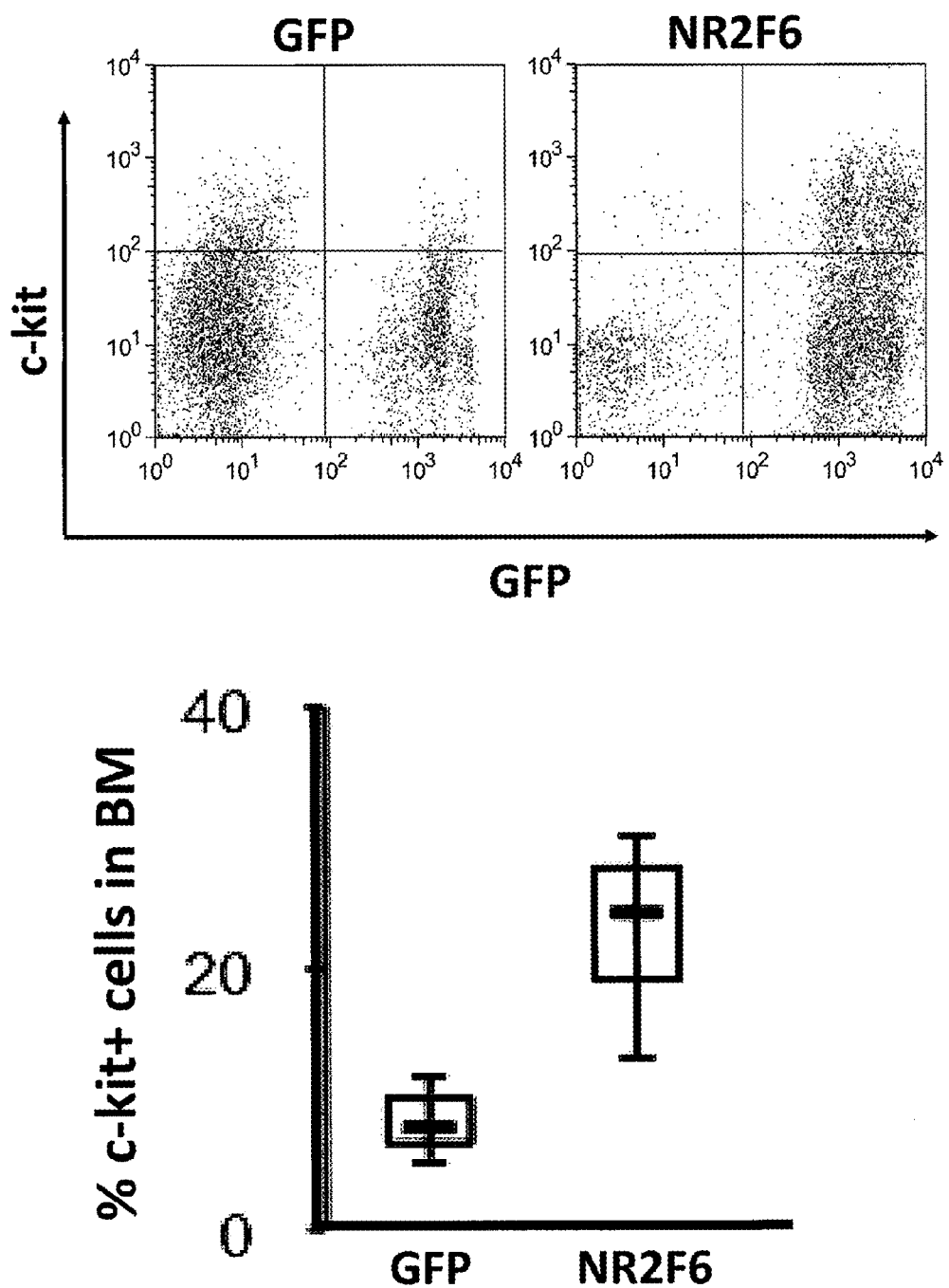
FIG. 20 shows that over-expression of NR2F6 in vivo causes expansion of bone marrow cells that express c-kit
Figure 21:
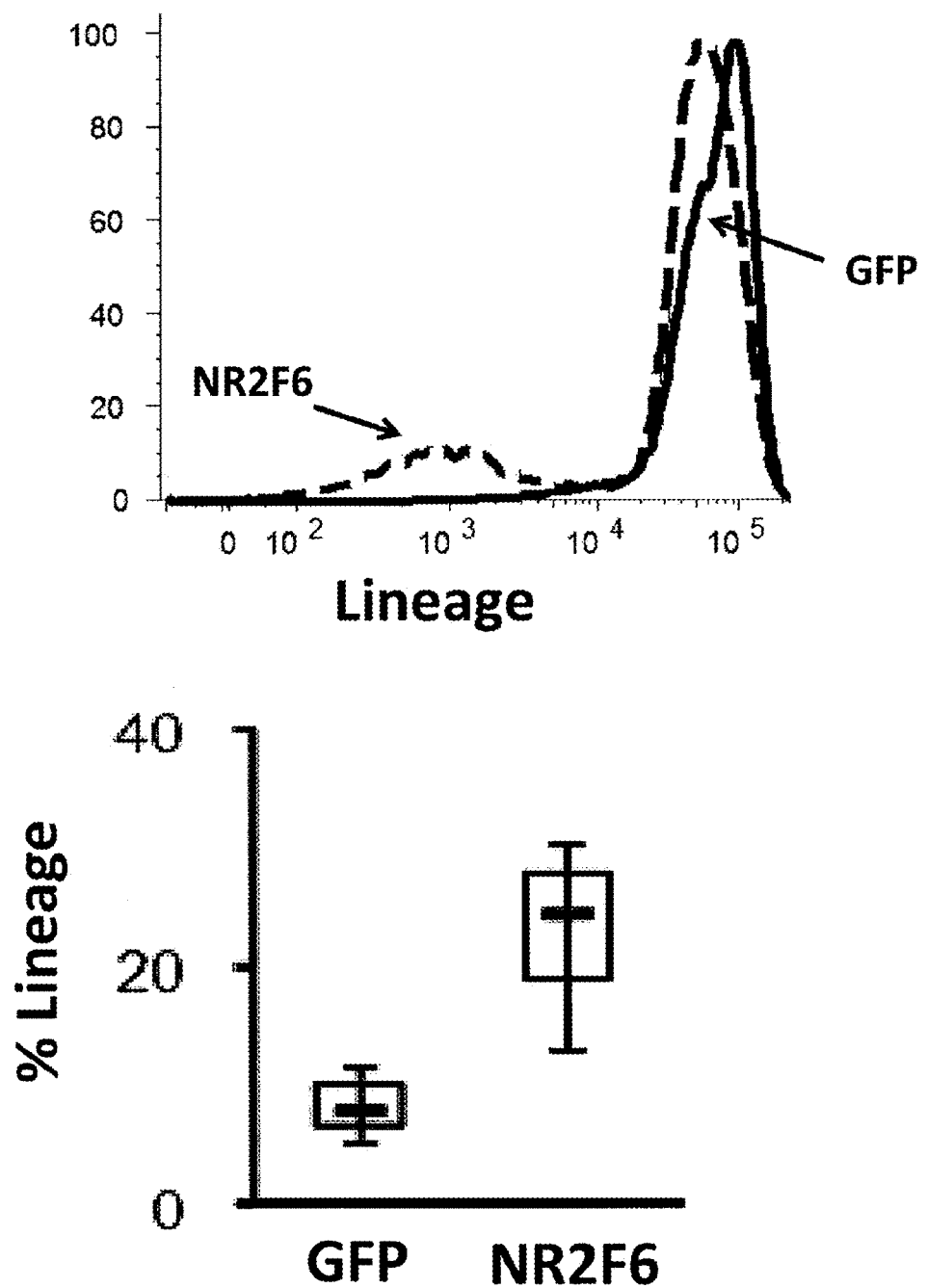
FIG. 21 shows that over-expression of NR2F6 in vivo causes expansion of bone marrow cells that lack expression of antigens associated with lineage commitment.
Figure 22:
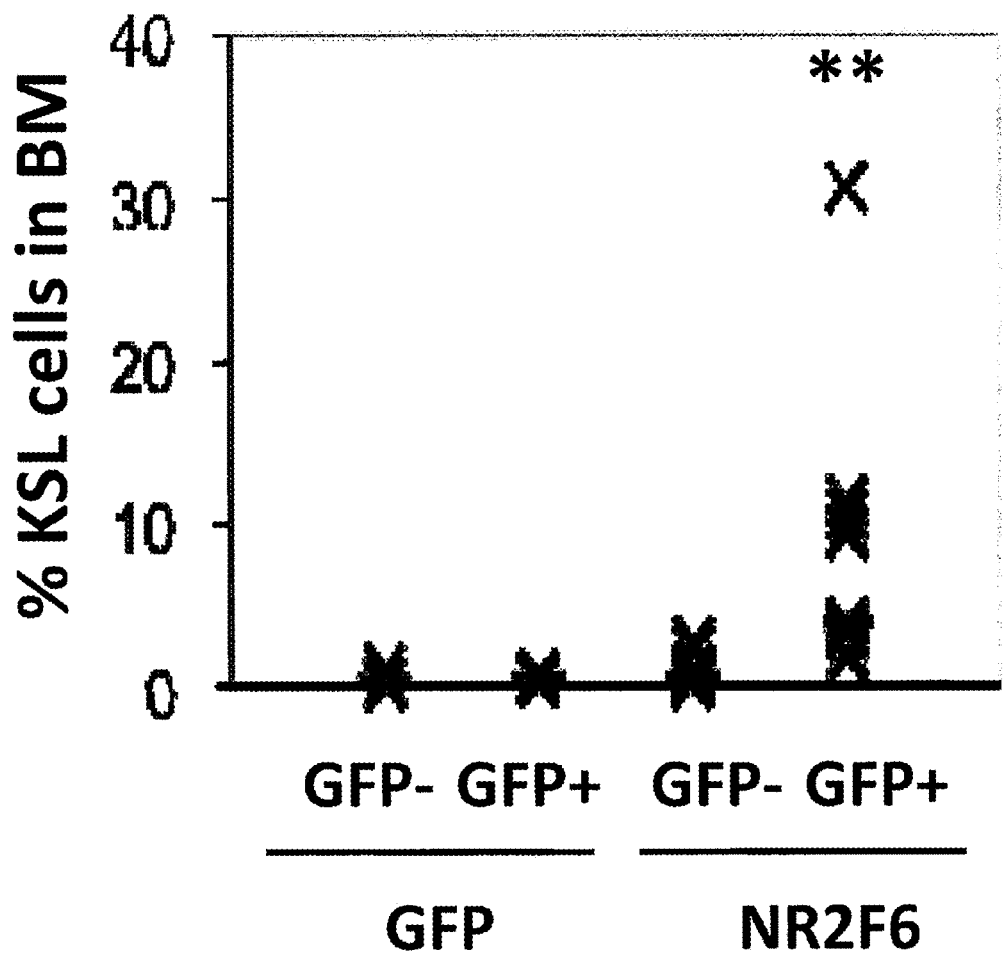
FIG. 22 shows that over-expression of NR2F6 in vivo causes expansion of bone marrow cells with the stem cell phenotype c-kit+, sca-1+, lineage−.

Flow cytometry on BM and spleen cells confirmed that the NR2F6-transduced graft contributed to trilineage haematopoiesis but also revealed the presence of an abnormal lineage-negative (lineage−) population that expressed moderate cKit antigen (FIGS. 19, 20 and 21). Fascinatingly, the size of the ckit+Sca-1+lineage−(KSL) population was markedly increased in NR2F6 recipients (FIG. 22). Thus, NR2F6-transduced HSCs show impaired differentiation, a propensity to accumulate, and a high rate of malignant transformation.

Figure 23A:
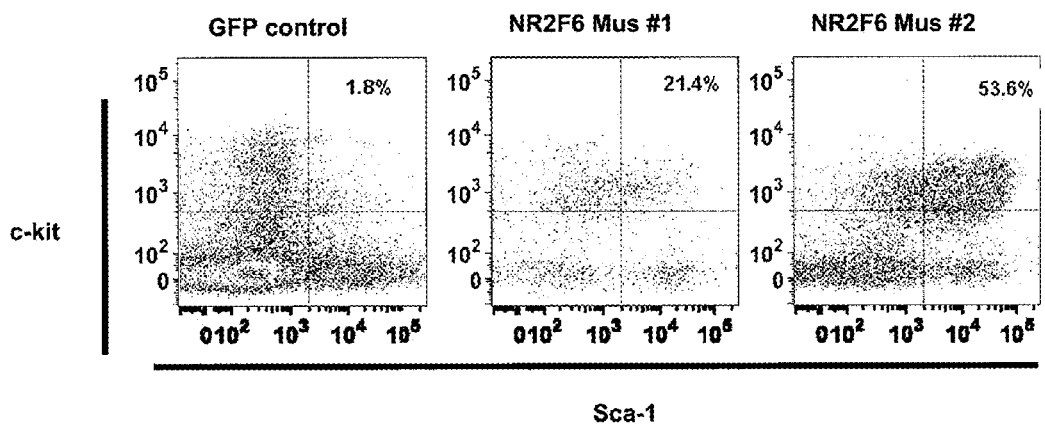
FIGS. 23A, 23B, and 23C show over-expression of NR2F6 in the bone marrow of healthy animals results in expansion of their hematopoietic stem cell.
Figure 23B:
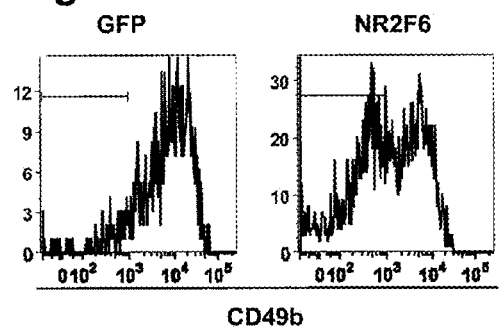
Figure 23C:
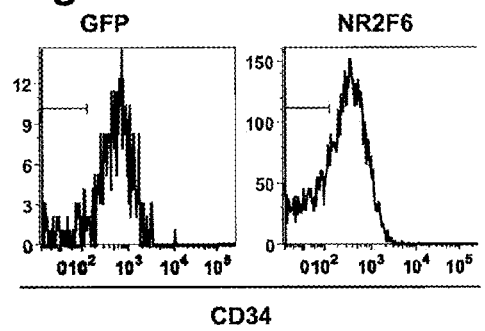

Over-expression of NR2F6 in the bone marrow of healthy animals results in expansion of their hematopoietic stem cell (FIG. 23). Mice that over-expressed NR2F6 in all of their bone marrow cells were generated by transducing bone marrow from 5-FU treated C57BI/6 using a retrovirus containing either GFP of NR2F6-IRES-GFP. Cells were then sorted and transplantation into lethally irradiated C57BI/6 hosts. Four weeks post transplant the bone marrow of these animals was analyzed by multicolour flow cytometry (FIG. 23A). There was a striking accumulation of stem cells in the bone marrow of animals that over-expressed NR2F6 (cells with the lineage−, c-kit+, sca-1+ immunopheonotype). Interestingly, there was an increase in the number of long-term stem cells found in the bone marrow of animals that over-expressed NR2F6 (cells with the lineage−, c-kit+, sca-1+, CD49b− immunophenotype and cells with the lineage−, c-kit+, sca-1+, CD34− immunophenotype) (FIG. 23B). The accumulation of hematopoietic stem cells in the bone marrow of NR2F6+ animals suggests that NR2F6 increases hematopoietic stem cell self-renewal. Furthermore, these data support the fact that NR2F6 is able to act upon the most primitive hematopoietic stem cell compartments and regulate their proliferation as well as the self-renewal of long-term hematopoietic stem cells. These data support the modulation of NR2F6 as a method of expanding stem cells ex vivo. These data also support the modulation of NR2F6 for the treatment of diseases associated with aberrant self-renewal, for example targeting of the cancer stem cell.

Figure 24:
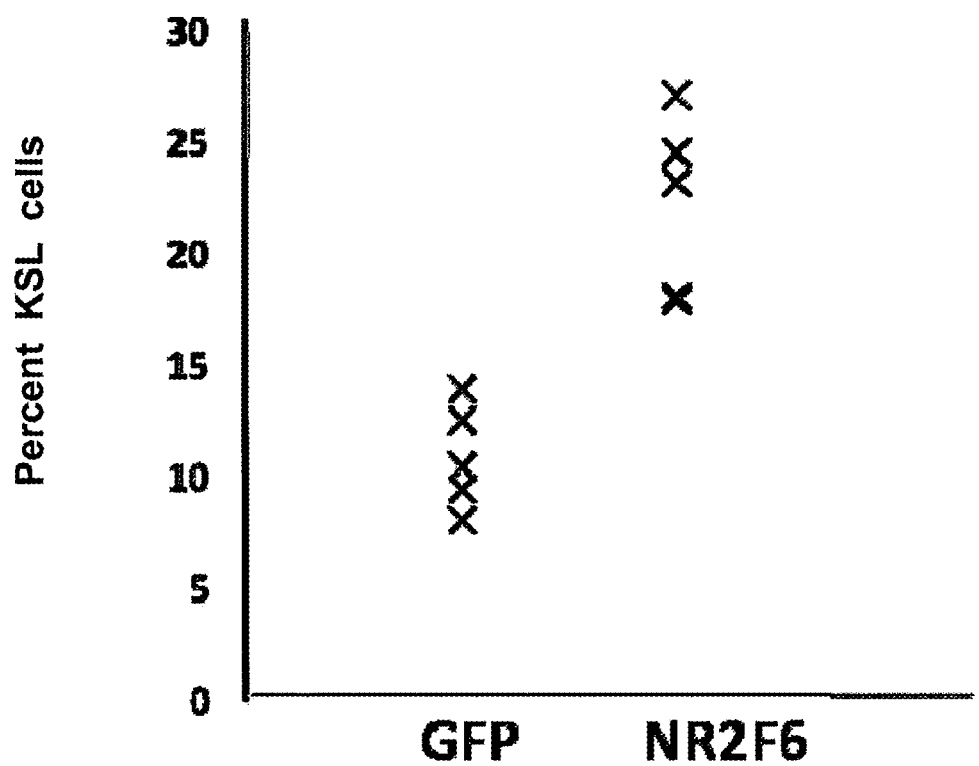
FIG. 24 shows that over-expression of NR2F6 enhances the in vitro maintenance of bone marrow cells with the stem cell phenotype c-kit+, sca-1+, lineage−.

NR2F6 overexpressing bone marrow was cultured in conditions that preserve stem cell maintenance (c-kit ligand; thrombopoietin; and Flt3 ligand in OP9 conditioned medium). Following three days in culture the proportion of stem cells with the immunophenotype ckit+Sca-1+lineage−(KSL) was determined by flow cytometry. I was observed that bone marrow that over-expressed NR2F6 contained more KSL cells than GFP control cultures (FIG. 24) suggesting that modulation of NR2F6 can be used to maintain and/or expand hematopoietic stem cells in culture.

Figure 25A:
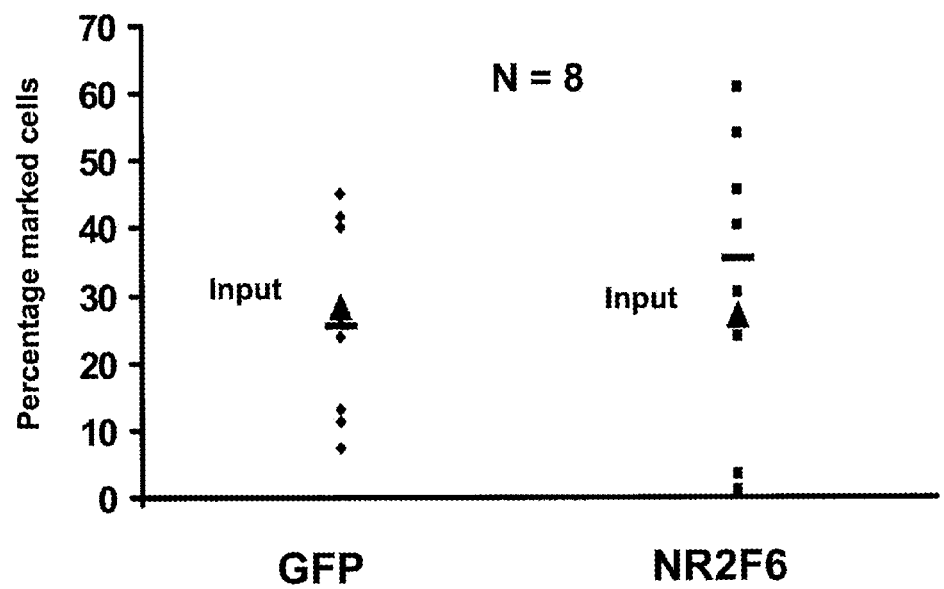
FIGS. 25A and 25B show over-expression of NR2F6 in the bone marrow of healthy animals enhances self-renewal in vivo.
Figure 25B:
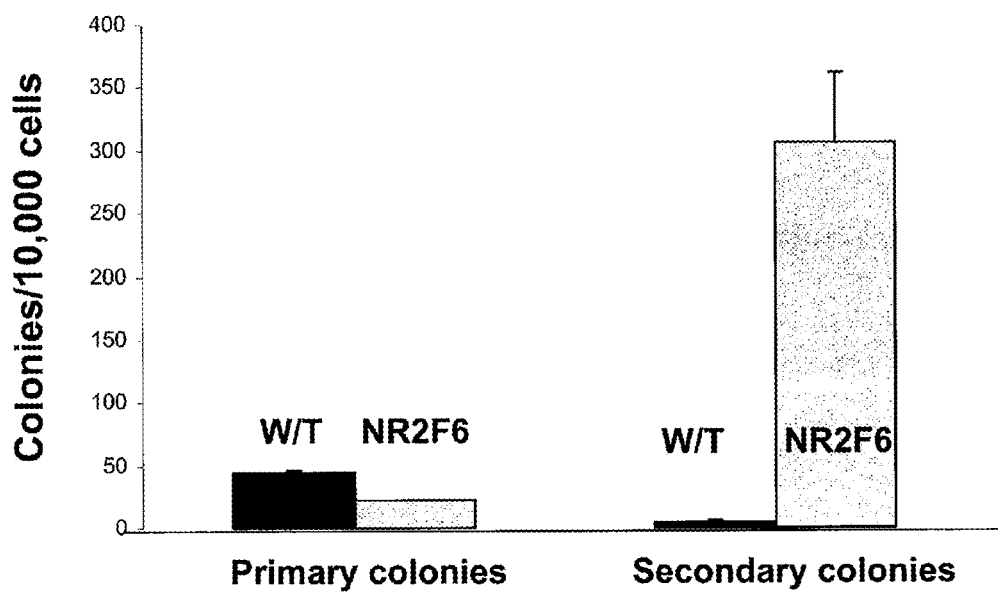

Over-expression of NR2F6 in the bone marrow of healthy animals enhances self-renewal in vivo (FIG. 25). Competitive bone marrow transplant experiments shows that over-expression of NR2F6 results in increased engraftment which evidences that over-expression of NR2F6 increases self-renewal (FIG. 25A). The self-renewal ability of bone marrow attained from animal that over-express either NR2F6-IRES-GFP or GFP was compared by assessing the bone marrow's secondary colony forming ability After the enumeration of primary methycellulose colonies cultures were harvested, washed with PBS and 10,000 of said cells were plated in another methycellulose culture to determine the ability of these cells to form colonies a second time (FIG. 25B). These secondary cultures were enumerated after another 12-14 days of culture. The ability of bone marrow that over-expresses NR2F6 to form a far greater number of secondary colonies compared to control bone marrow demonstrates that over-expression of NR2F6 increases hematopoietic cell self-renewal and inhibits the terminal differentiation of hematopoietic cells.

Figure 26A:
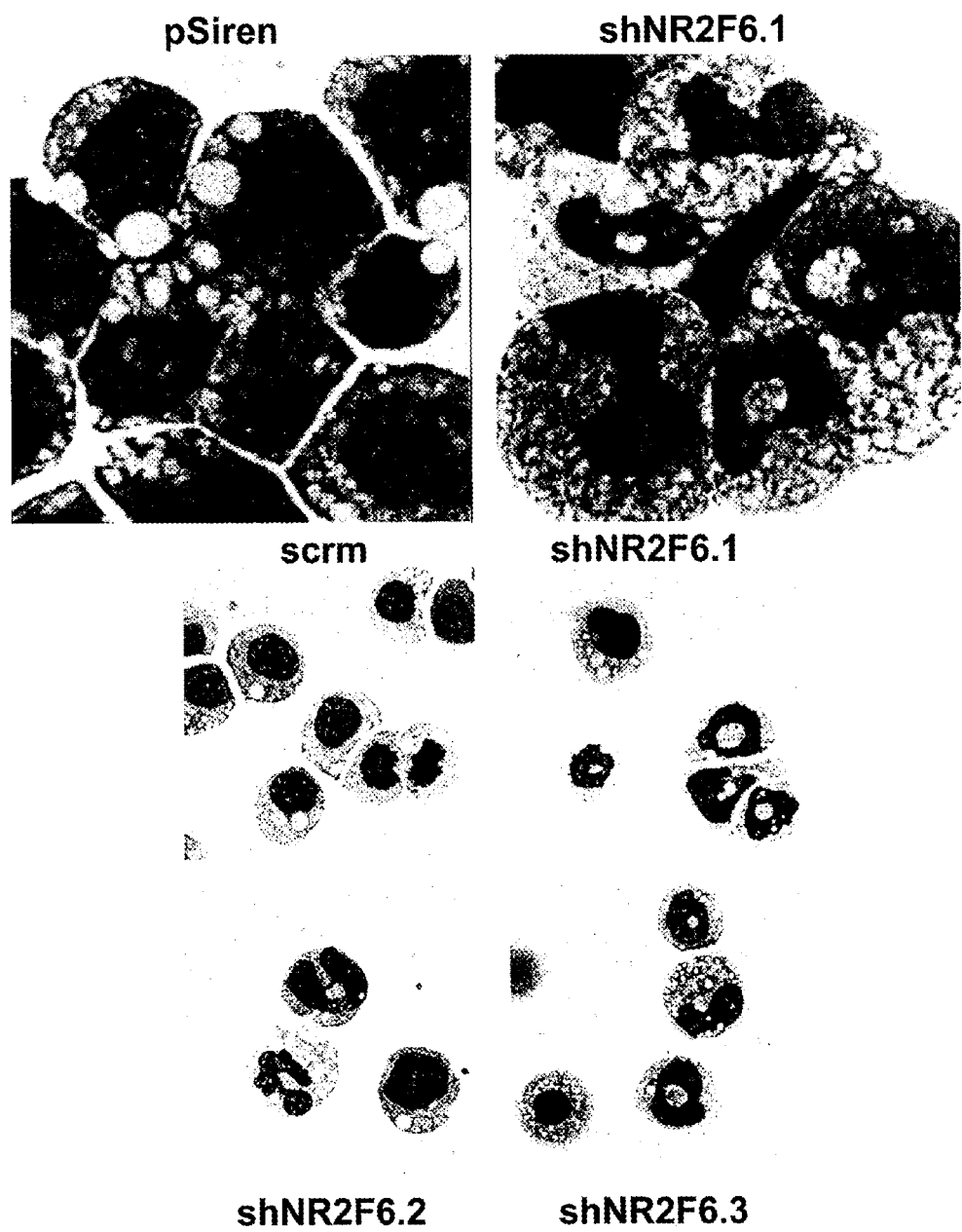
FIGS. 26A and 26B show knock down of NR2F6 using short-hairpin RNAs induces differentiation and maturation of 32Dcl3 mouse hematopoietic cells.
Figure 26B:
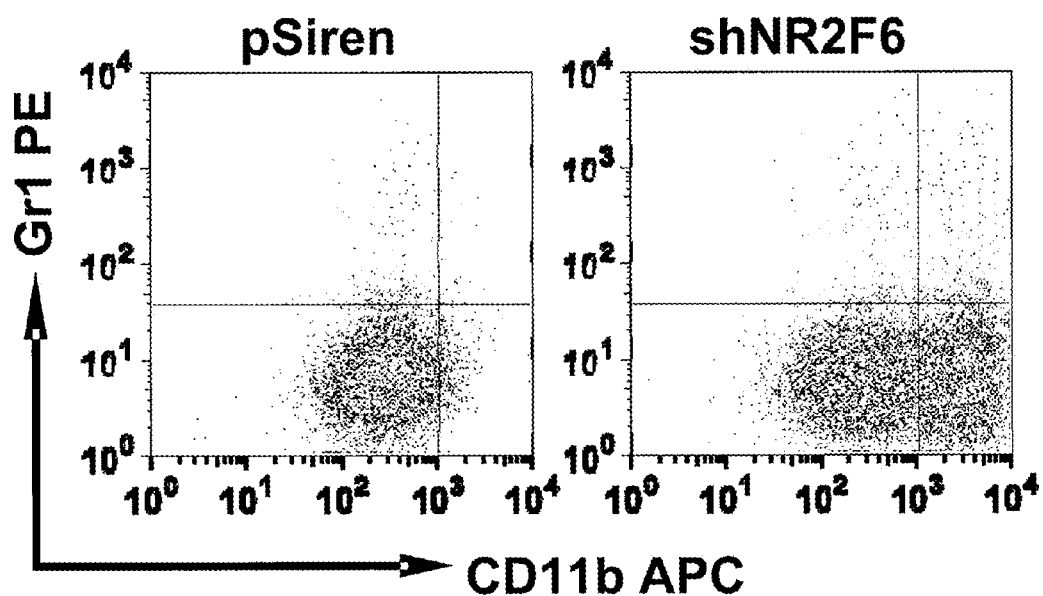

Knock down of NR2F6 using short-hairpin RNAs induces differentiation and maturation of 32Dcl3 mouse hematopoietic cells (FIG. 26). Cytospins of cells transduced with either the pSiren universal negative control retroviral plasmid, or an shRNA retroviral plasmid that targets mouse NR2F6 induces the differentiation and maturation of 32Dcl3 cells demonstrate the knock down of NR2F6 induces spontaneous myeloid cell differentiation (FIG. 26A). Flow cytometry on 32Dcl3 mouse hematopoietic cells transduced with either the pSiren universal negative control retroviral plasmid or an shRNA retroviral plasmid that targets the mouse NR2F6, confirms that knockdown of NR2F6 induces spontaneous myeloid cell differentiation (FIG. 26B).

Figure 27A:
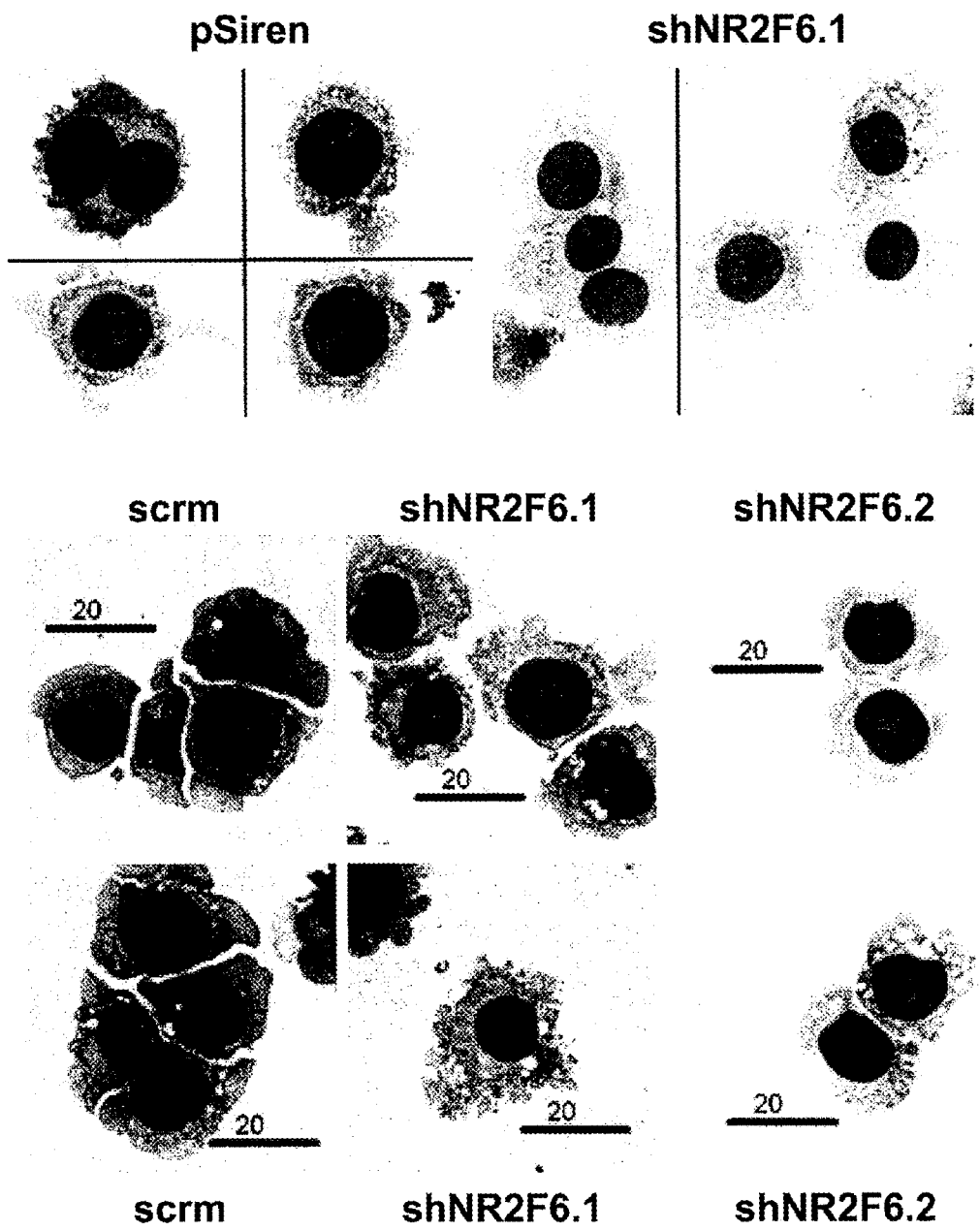
FIGS. 27A, 27B, and 27C show knock down of NR2F6 using short-hairpin RNAs induces terminal differentiation, blood cell maturation death of U937 human leukemia cells.
Figure 27B:
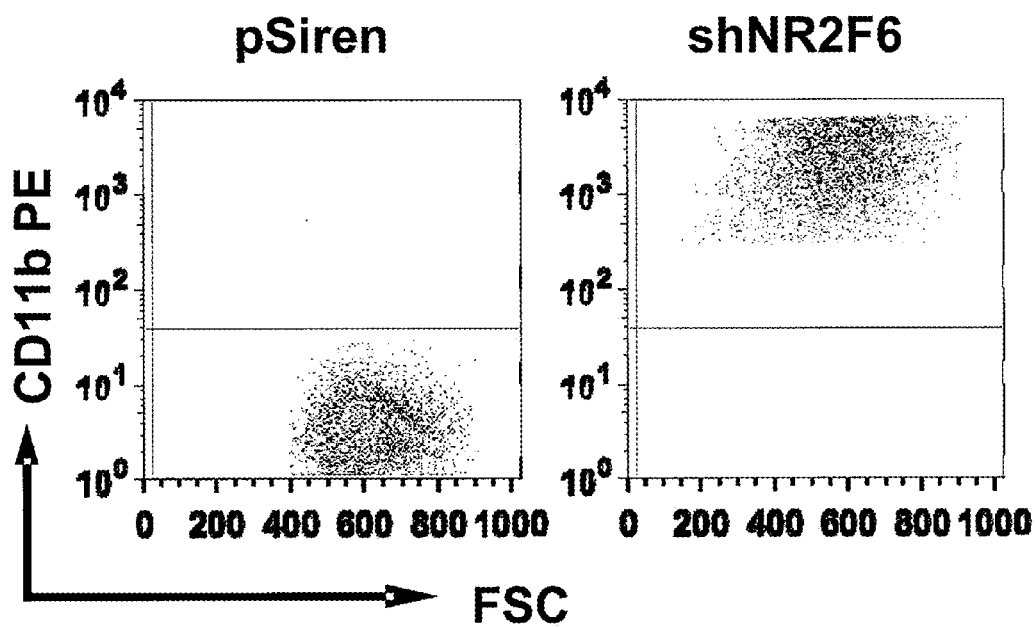
Figure 27C:
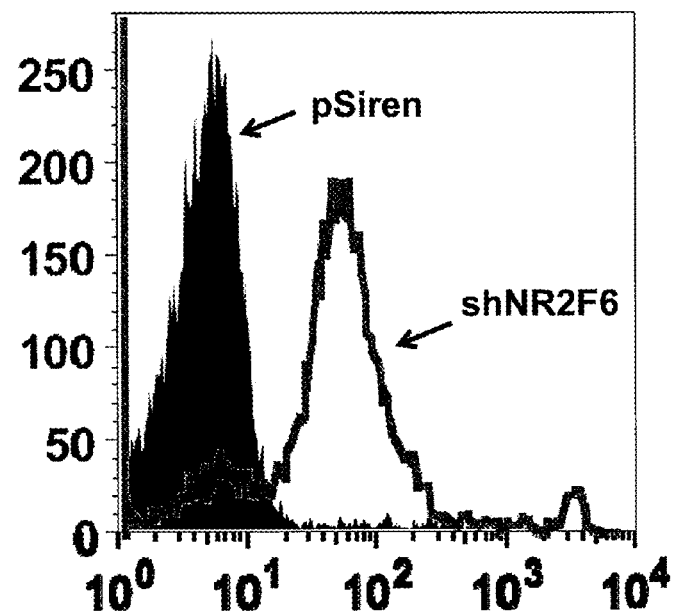

Knock down of NR2F6 using short-hairpin RNAs induces terminal differentiation, blood cell maturation death of U937 human leukemia cells (FIG. 27). Cytospins of cells transduced with either the pSiren universal negative control retroviral plasmid, or an shRNA retroviral plasmid that targets human NR2F6 induces the differentiation and maturation of U937 cells demonstrate the knock down of NR2F6 induces spontaneous myeloid cell differentiation (FIG. 27A). Flow cytometry on U937 human myelomonocytic leukemia cells transduced with either the pSiren universal negative control retroviral plasmid or an shRNA retroviral plasmid that targets the human NR2F6, confirms that knockdown of NR2F6 induces spontaneous myeloid cell differentiation (FIG. 27B).

Figure 28:
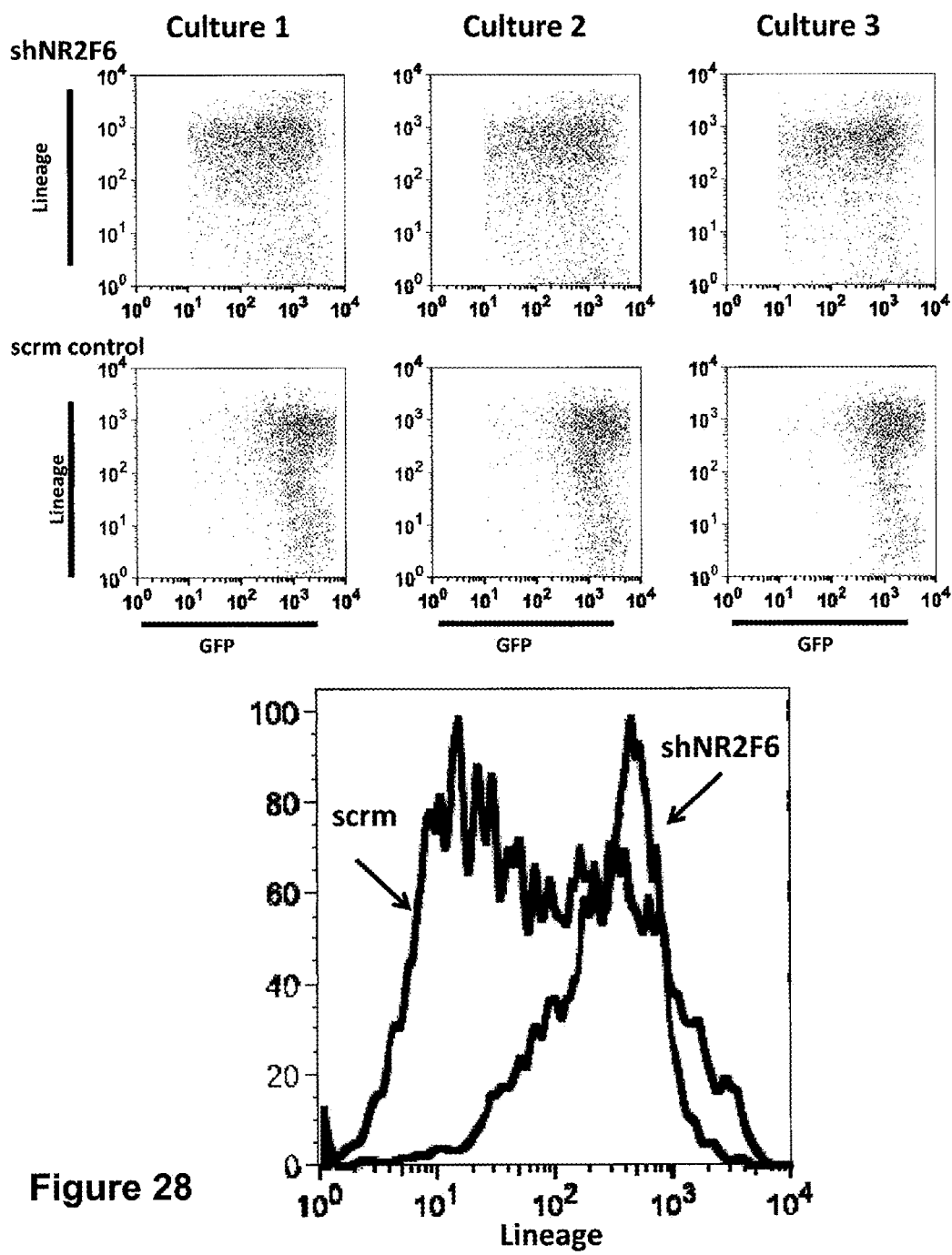
FIG. 28 shows that knock down of NR2F6 using short-hairpin RNAs induces rapid depletion of immature bone marrow cells in ex vivo culture.
Figure 29:
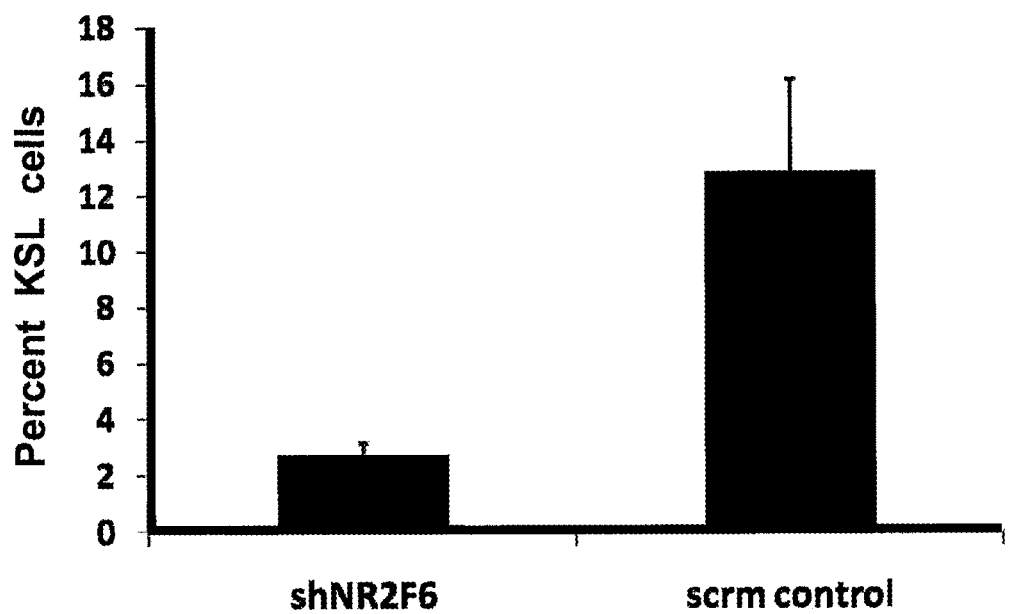
FIG. 29 shows that knock down of NR2F6 using short-hairpin RNAs induces rapid depletion of bone marrow cells with the stem cell phenotype c-kit+, sca-1+, lineage− in ex vivo culture.
Figure 30:
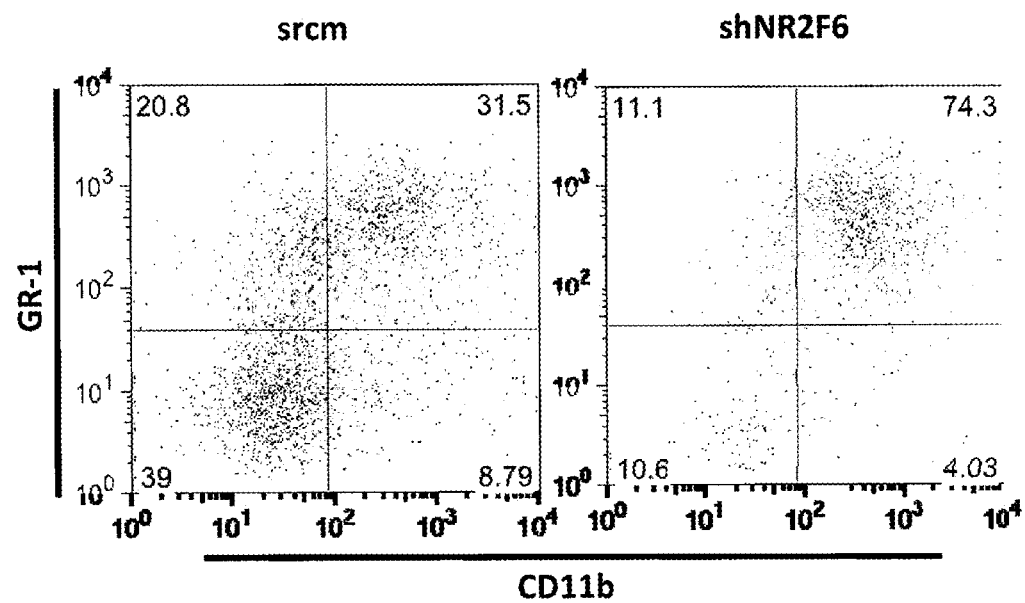
FIG. 30 shows that knock down of NR2F6 using short-hairpin RNAs induces rapid differentiation of immature bone marrow cells
Figure 31:
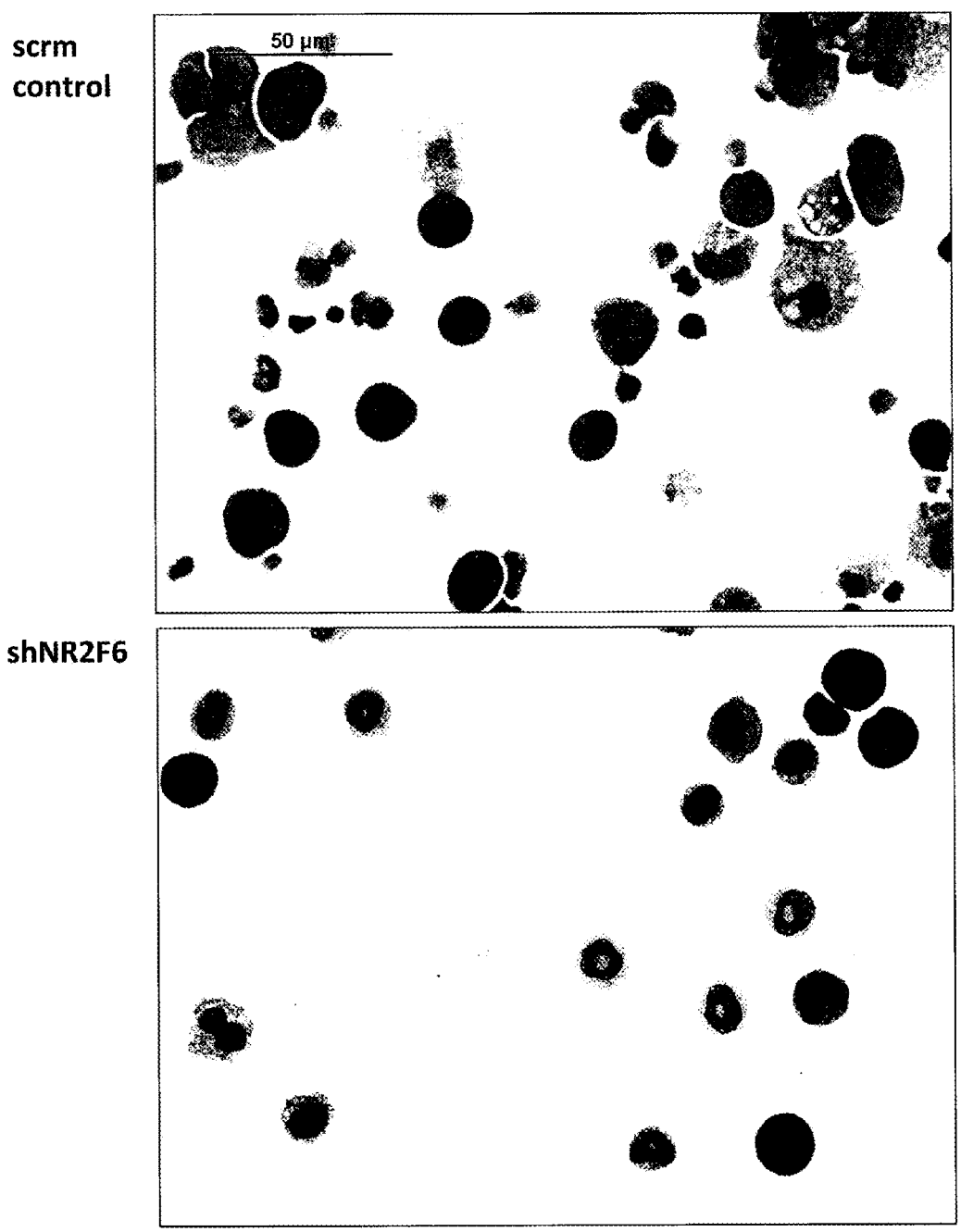
FIG. 31 shows morphologically that knock down of NR2F6 expression using short hairpin RNA (shNR2F6) reduces the number of immature bone marrow cells (blast cells) and promotes differentiation into mature cells in ex vivo suspension culture

We then showed that knock down of NR2F6 expression using short hairpin RNA (shNR2F6) promotes the differentiation of immature bone marrow cells in suspension culture when compared to the scrambled shRNA control (scrm) (FIGS. 28 and 29). Murine bone marrow cells were cultured in conditions that preserved stem cell maintenance (c-kit ligand; thrombopoietin; and Flt3 ligand in OP9 conditioned medium) and transduced with either an shRNA targeting NR2F6 or a scrambled control shRNA. Following seven days in culture cells were analysed by flow cytometry. Knocking down the expression of NR2F6 dramatically reduced the number of immature cells, i.e. cells devoid of markers of lineage commitment (FIG. 28), and of stem cells (ckit+Sca-1+lineage−, KSL cells) (FIG. 29). Rather, knock down of NR2F6 promoted the differentiation and maturation of bone marrow cells into neutrophils, as shown by flow cytometry (FIG. 30) and morphology (FIG. 31).

Figure 32:
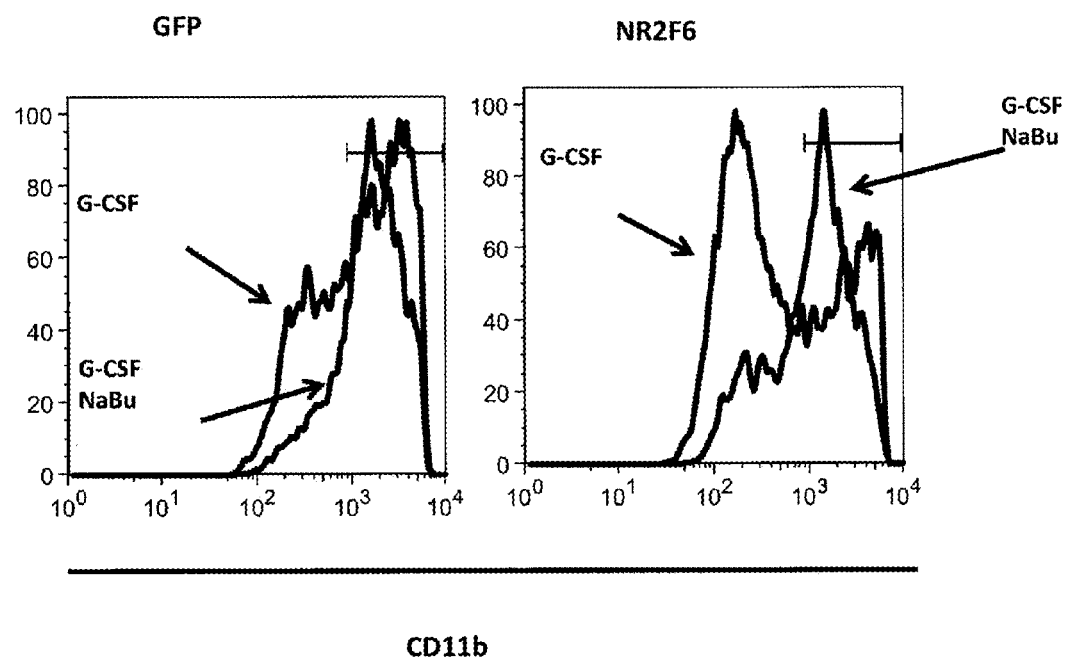
FIG. 32 shows that NR2F6 can be modulated using histone deacetylase inhibitors

It has been reported that NR2F6 exerts its regulatory effects primarily as a transcriptional repressor (Liu, X., Huang, X., and Sigmund, C. D. (2003). Identification of a nuclear orphan receptor (Ear2) as a negative regulator of renin gene transcription. Circ Res 92, 1033-1040.). The repressor activity of nuclear receptors is mediated by recruitment of corepressors with histone deacetylase (HDAC) activity; we therefore evaluated the importance of this mechanism in the effects of NR2F6 on haematopoiesis and evaluated weather the activity of NR2F6 can be modulated with an HDAC inhibitor. 32Dcl3-NR2F6 cells were incubated with the non-specific histone deacetylase inhibitor sodium butyrate prior to treatment with G-CSF. Whereas non-treated 32Dcl3-NR2F6 cells failed to differentiate in response to GCSF, sodium butyrate pretreated cells showed recovery of G-CSF induced differentiation as indicated by cell surface CD11b expression (FIG. 32). Thus, HDAC-mediated transcriptional repression likely accounts for at least part of the mechanism by which NR2F6 impairs hematopoietic differentiation; and hence the activity of NR2F6 can be modulated using HDAC inhibitors.

Overview of T cell Experiment

NR2F6 (NR2F6) is an orphan nuclear receptor belonging to the COUP-TF family of transcriptional regulators; one of three mammalian homologues of the *Drosophila* seven-up gene, which plays a role in neuroblast and retinal cell fate decisions. NR2F6 is highly expressed in hematopoietic stem cells (HSCs), with expression being necessary and sufficient to block the differentiation of leukemia cells. However, the role of NR2F6 in T cell development has not been fully established. Since both COUP-TF family members and the T cell regulator RORγt (Rorc) antagonize retinoid and thyroid hormone receptor signaling, we investigated whether NR2F6 expression may have a role in T cell development. Here, we describe a novel role for the orphan nuclear receptor NR2F6 in regulating T cell development. Specifically, in comparison to the WT cells, over-expression of NR2F6 (NR2F6++) in a competitive bone marrow (BM) transplantation assay resulted in limited T cell development in vivo. Furthermore, mice that received grafts consisting of 100% NR2F6++ BM cells demonstrated a more than 10 fold decrease in their thymic size and cellularity relative to controls. Thymic cortexes from NR2F6++ mice had decreased lymphocyte cellularity; while medullas had a starry-sky appearance, indicative of apoptosis. In vitro, differentiation of EAR2-transduced murine BM-HSCs in OP9-DL1 cultures showed a reduction in the number of cells generated from NR2F6++ BM-HSCs and a block at the differentiation from DN4 to DP and SP cells, as a consequence of increased apoptosis. Based on these findings we conclude that NR2F6++ cells were able to migrate to, but not fully repopulate, the thymus due to cell intrinsic defects in the proliferation of DN cells followed by their inadequate differentiation from the DP to SP stage of T cell development. Thus, downregulation of NR2F6 is indispensable for the survival and proliferation of developing T cells.

The orphan nuclear receptor v-erb-A related-2 (EAR-2, NR2F6) is a mammalian homologue of the *Drosophila* gene seven-up (svp). We have previously established that NR2F6 functions as a gatekeeper of the undifferentiated state, preventing the differentiation of acute myeloid leukemia cells into mature blood cells thereby maintaining their clonogenicity [1]. The expression of NR2F6 is highest in hematopoietic stem cells (HSCs) and declines drastically upon normal hematopoietic differentiation, while over-expression of NR2F6 blocks differentiation of leukemia cell lines. This role for NR2F6 in the regulation of differentiation is consistent with the function of the *Drosophila* homologue svp, which plays a role in cell fate decisions in neurological development [2]. The mammalian homologues of NR2F6 also play important roles in differentiation and cell fate decisions. Specifically, COUP-TFI is important in neuronal development [3-5], while COUP-TFII is involved in determination of cell identity for venous-arterial cells [6], coronary vessels [7], lymphatic endothelial cells [8-10], Leydig cells [11], trophoblast giant cells [12], adipocytes [13-15], and neuronal cells [16-18]. NR2F6 null mice exhibit agenesis of the locus coeruleus [19], a midbrain nucleus that regulates circadian behavior and nociception.

A role of NR2F6 in lymphopoiesis has not been established. Although targeted deletion of NR2F6 does not result in aberration of lymphocyte development, NR2F6-null mice have hyper-reactive Th17 CD4+ T lymphocytes and are hyper-susceptible to Th17-dependent experimental autoimmune encephalomyelitis [20].

In addition, NR2F6 functions as a transcriptional repressor in vitro by directly inhibiting the transactivating ability of numerous genes including the thyroid hormone receptor [21]. Like many nuclear receptors, NR2F6 heterodimerizes with the retinoid X receptor-α (RXR-α) [22], and can inhibit retinoid signaling in vitro as demonstrated by blocking differentiation induced by all trans-retinoic acids [1]. No interaction has been shown between NR2F6 and the known Th17 master-regulator RORγt (Rorc) [23]. Interestingly, like NR2F6, RORγt is also an orphan nuclear receptor that represses both retinoid and thyroid hormone receptor signaling [24]. Over-expression studies have demonstrated that a decrease in expression of RORγt is necessary for T cell development to proceed [25]. Furthermore, retinoid signaling has been associated with protection of immature T cells from activation-induced cell death, a type of apoptosis, during T cell development [26-30]; hence it is conceivable that inhibition of retinoid signaling may adversely affect T cell development. Given that NR2F6 regulates both retinoid signaling and thyroid hormone receptor signaling, it is possible that over-expression of NR2F6 may have a role similar to RORγt, expression of which needs to be decreased for T cell development to ensue.

Here we describe for the first time a role for NR2F6 in the specification of lymphoid cells. Similar to RORγt, over-expression of NR2F6 abrogates the developmental program necessary for T cell lymphopoiesis. We show that NR2F6 expression is lower in thymocytes than in HSCs; and that in adoptive transfer experiments, early progenitor cells engineered to express NR2F6 at a high level (NR2F6++) fail to repopulate the thymus. Moreover, in vitro differentiation of NR2F6++ HSCs in an OP9-DL1 cell system results in greatly reduced numbers of cells relative to controls, indicating that this phenotype is cell intrinsic. Overall, our data demonstrate that NR2F6 is a novel regulator of T cell development necessary for the proliferation and survival of developing T cells.

Materials and Methods

Animals

C57BL/6 mice were obtained from the Jackson Laboratory (Bar Harbor, Me.) and stored in a pathogen-free facility at Sunnybrook Research Institute. All work was done in accordance with the Sunnybrook Research Institute Animal Care and Use Guidelines.

Bone Marrow Transduction

Twelve-week-old C57BL/6 donor mice were treated with 5 fluorouracil [150 µg/g body mass] by intraperitoneal injection. Ninety-six hours later, mice were sacrificed and bone marrow collected. Cells were then stimulated for twenty-four hours prior to infection with MMP-GFP or MMP-NR2F6-IRES-GFP retroviral supernatants generated as described [31, 32]. Forty-eight hours later, GFP-positive cells were collected by fluorescence activated cell sorting (FACS).

Bone Marrow Transplantation

Chimeric mice were generated by injection of lethally irradiated animals with grafts containing a mixture of transduced (GFP or NR2F6; $2.5 \times 10^4$ cells) and mock-transduced ($7.5 \times 10^4$ cells) donor cells. Thymi, bone marrow and spleens from recipients of chimeric bone marrow cells were harvested at either early (4-6 weeks) or late (12-16 weeks) time points. Animals transplanted with 100% transduced cells were generated by transplanting lethally irradiated animals with bone marrow grafts containing between $4 \times 10^4$ and $1 \times 10^5$ transduced bone marrow cells. The same graft size was administered to all recipients in each transplantation experiment.

Histological Sections

Thymi were fixed for 24 hours in buffered formalin (Sigma-Aldrich, St Louis, Mo.) followed by paraffin embedding, slicing, and staining with hematoxylin and eosin by the Sunnybrook Research Institute histology core facility.

Cell Lines

OP9-DL1 cells were generated from the OP9 bone marrow stromal cell line and maintained as previously described [33].

FLow Cytometry

Biotin-, FITC-, PE-, PE-Cy5-, PE-Cy7-, APC-, APC-Cy7- mAbs were purchased from BD Biosciences or eBioscience. The following conjugated antibodies were used: anti-B220 (RA3-6B2), anti-CD3e (145-2C11), anti-CD4 (GK1.5, L3T4), anti-CD8a (LY-2, Lyt-2, 53-6.7), anti-CD11 b (M1/70), anti-CD16/CD32 (2.4G2), anti-CD19 (1D3), anti-CD25 (7D4), anti-CD44 (IM7), anti-CD45 (30-F11), anti-CD117 (2B8), anti-TCRβ (H57-597), Sca-1 (E13-161.7) and TER119 (TER-119). Cells were stained by standard staining techniques and analyzed on a FACS-Calibur or LSRII flow cytometer (BD Biosciences). Data files were analyzed with Flow-Jo (Tree Star). Dead cells were excluded from all data by forward- and side-scatter, and 4',6-diamidino-2-phenylindole dihydrochloride (DAPI) staining (Molecular Probes). Cell sorting was performed with a FACSDiVa or a FACSAria cell sorters (BD Biosciences). Annexin V-FITC staining was performed according to the manufacturers' recommended procedure (BD Pharmingen), and the percentage of cell death was calculated by adding percentages of Annexin $V^+$, Annexin $V^+$ $PI^+$ and $PI^+$ cells. Purity was typically greater than 98% for all populations as determined by post-sort analysis.

OP9-DL-1 Cultures and Analysis of T Cell Subsets

Bone marrow infected with either NR2F6 or GFP was sorted for transduced cells (GFP+) with the c-kit+, sca-1+, lineage− (KSL) immunophenotype. Transduced BM-HSCs cells were plated on OP9-DL1 cells in a 6-well plate in triplicate and maintained in conditions previously described [34, 35].

Quantitative PCR

T cell subsets were sorted directly into Trizol (Invitrogen, Carlsbad, Calif.). Total mRNA was isolated as per the manufacturer's instructions. mRNA was reverse transcribed using Superscript II reverse transcriptase (Invitrogen, Carlsbad, Calif.). Quantitative PCR was performed on an ABI light cycler using SYBR® Green Master Mixes (Invitrogen, Carlsbad, Calif.). Calculations were completed using relative quantification method, where the samples were normalized to β-actin expression.

Primer Sequences for NR2F6 are as Follows

```
Fwd:
5'-CCTGGCAGACCTTCA ACAG -3'
and

Rev:
5'-GATCCTCCTGGCCCATAGT -3'.
```

Results

Figure 33:
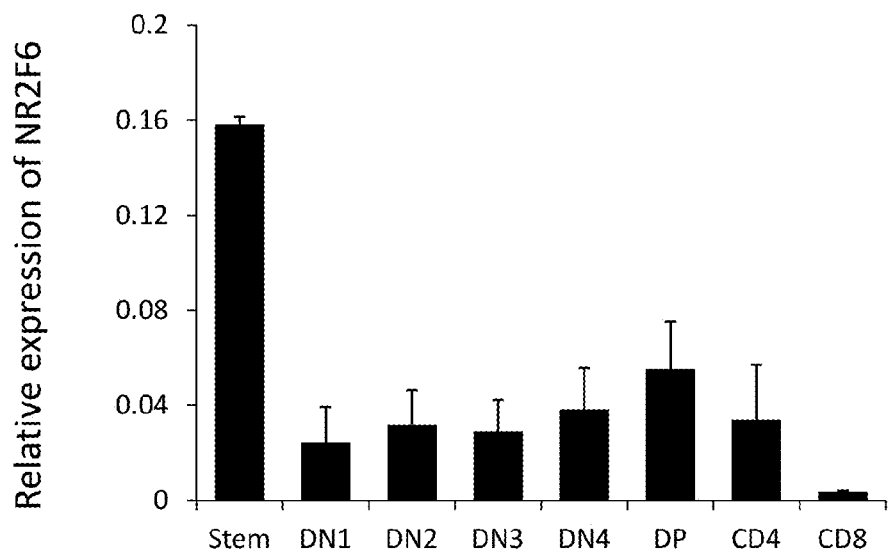
FIG. 33 shows expression of NR2F6 relative to the L32 housekeeping gene in stem cells versus T cell subsets in the thymus.

NR2F6 Expression Decreases Upon Hematopoietic Stem Cell Differentiation into Immature T Cells NR2F6 expression is heterogeneous throughout the hematopoietic hierarchy, with its expression being highest in long-term repopulating HSCs and generally declining with the differentiation of progenitor cells [31]. Likewise, expression of NR2F6 mRNA declined sharply from the KSL (c-kit$^+$, sca-1$^+$, lineage$^-$) hematopoietic stem cell stage, to the immature double negative (DN) 1 T cell stage (FIG. 1). Expression of NR2F6 amongst immature T cell subsets (DN1-DN4) did not differ significantly; however, expression of NR2F6 decreased sharply from the double positive (DP) cells to CD8+ single positive (SP) cells (FIG. 33).

NR2F6 Expression Places Developing Thymocytes at a Competitive Disadvantage

Figure 34:
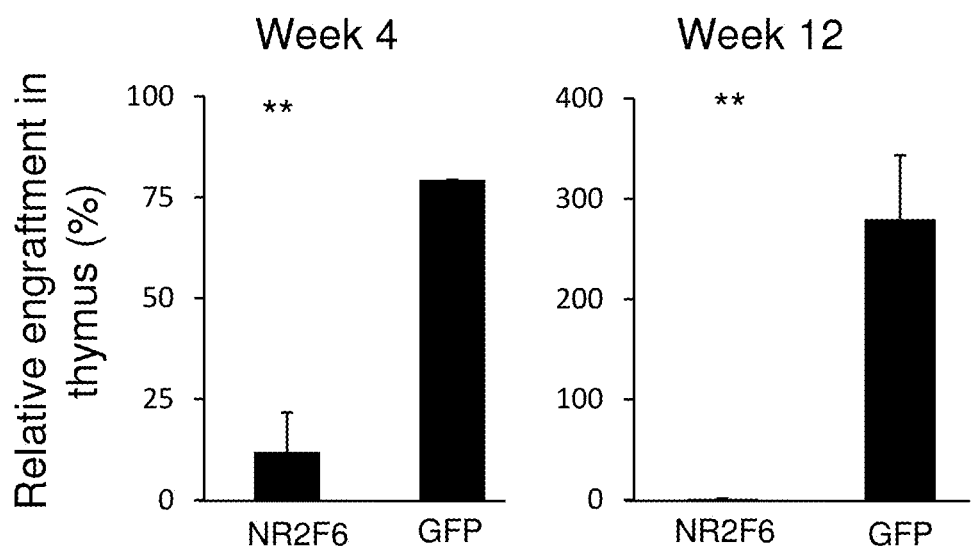
FIG. 34 shows that bone marrow that over-expresses NR2F6 does not engraft the thymus.
Figure 35:
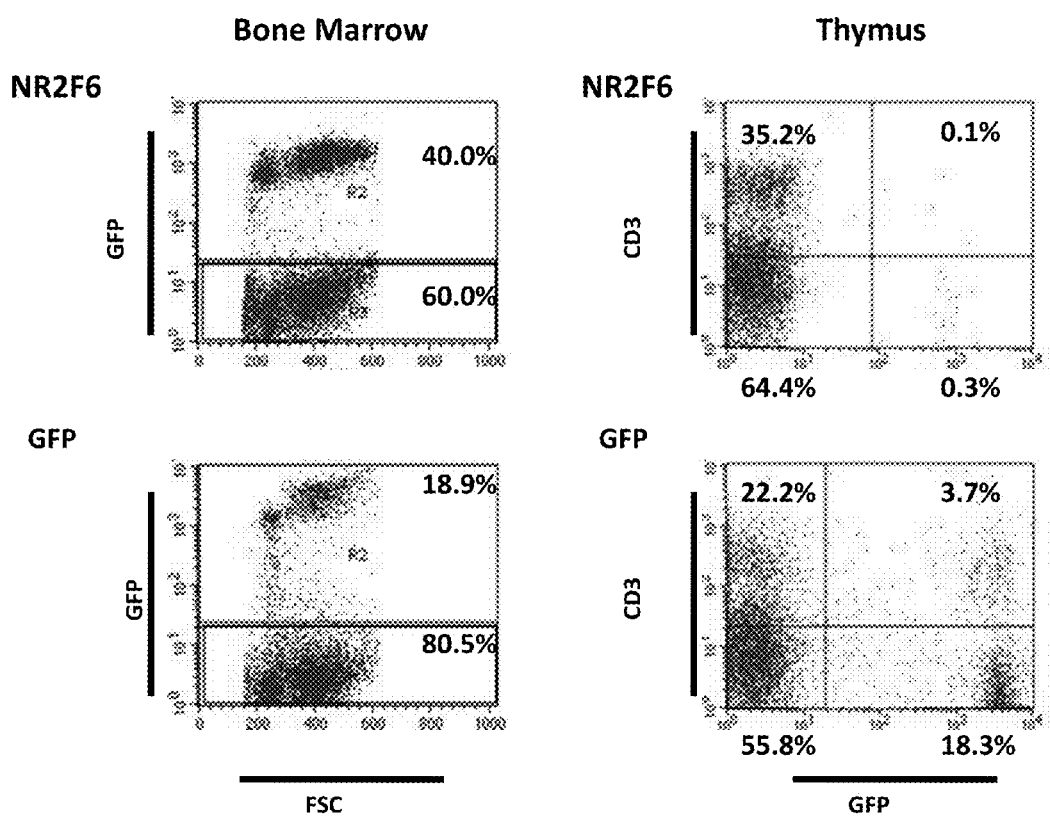
FIG. 35 shows that bone marrow that over-expresses NR2F6 does not engraft the thymus.
Figure 36:
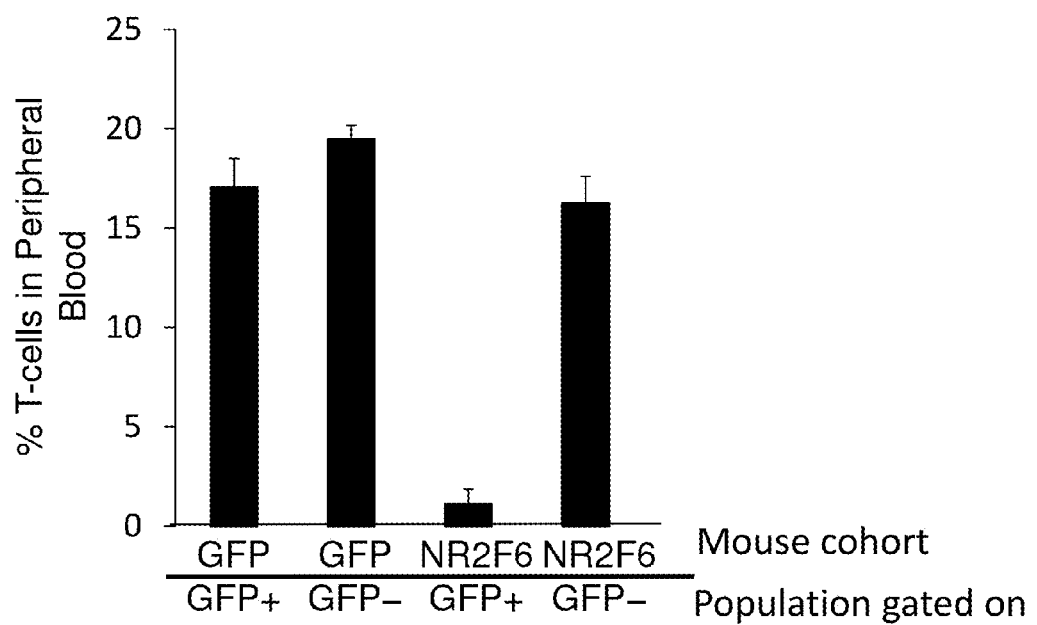
FIG. 36 shows that NR2F6 over-expressing cells do not contribute to peripheral T cells in the peripheral blood.
Figure 37:
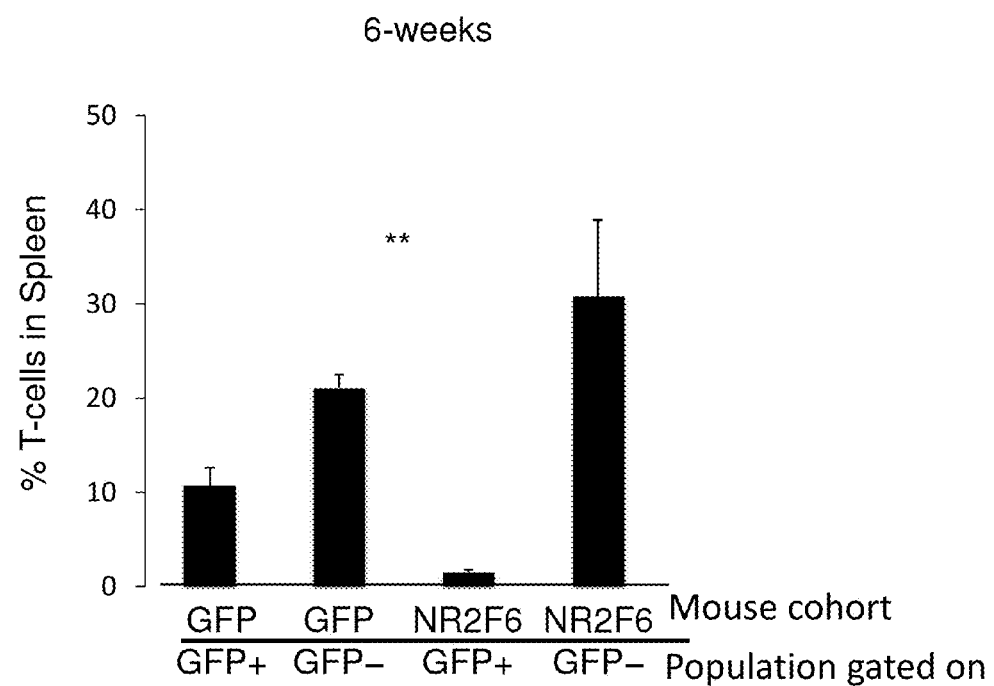
FIG. 37 shows that NR2F6 over-expressing cells do not contribute to peripheral T cells in the spleen at 6-weeks.
Figure 38:
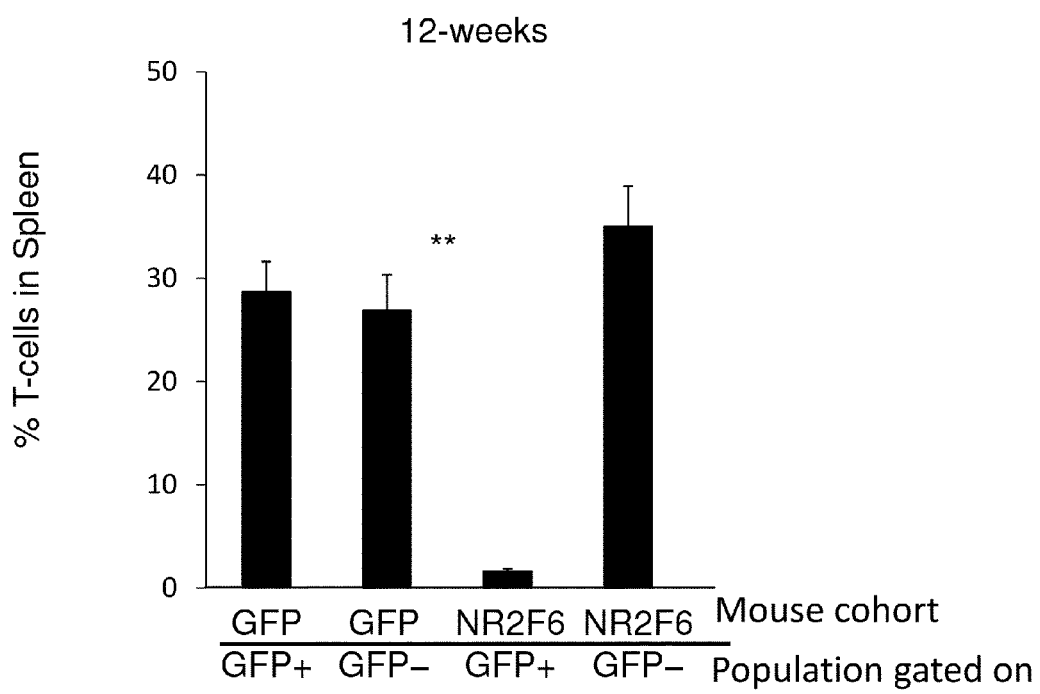
FIG. 38 shows that NR2F6 over-expressing cells do not contribute to peripheral T cells in the spleen at 12-weeks.

The effects of NR2F6 on lymphopoiesis were assessed in vivo by competitive transplantation of NR2F6 or GFP transduced bone marrow cells (n=43). Competitive repopulation of lethally irradiated murine hosts with GFP transduced bone marrow cells resulted in successful engraftment and T cell development, with GFP+ T cells present in the thymus and periphery at rates comparable to those of transduced cells in the original graft (FIGS. 34 and 35). In contrast, six weeks post-transplant, the proportion of CD3+ cells derived from NR2F6 transduced bone marrow cells was greatly diminished relative to the controls. Complete abrogation of CD3+ cells derived from NR2F6 transduced T cells was observed in both the thymus (FIGS. 34 and 35) and periphery (FIGS. 36, 37 and 38) at 6 and 12 weeks post-transplant. A lack of mature T cells was observed in all recipients of NR2F6 transduced bone marrow. We determined this using both expression of the mature cell surface markers CD3, as well as the markers CD4 and CD8 in some recipients (data not shown), to confirm that these mice lack mature T cells and that the observed phenomenon is not attributed to a direct effect of NR2F6 on expression of the CD3 gene.

Effacement of Thymic Cortex and Apoptosis in Medulla of NR2F6++Animals

Figure 39:
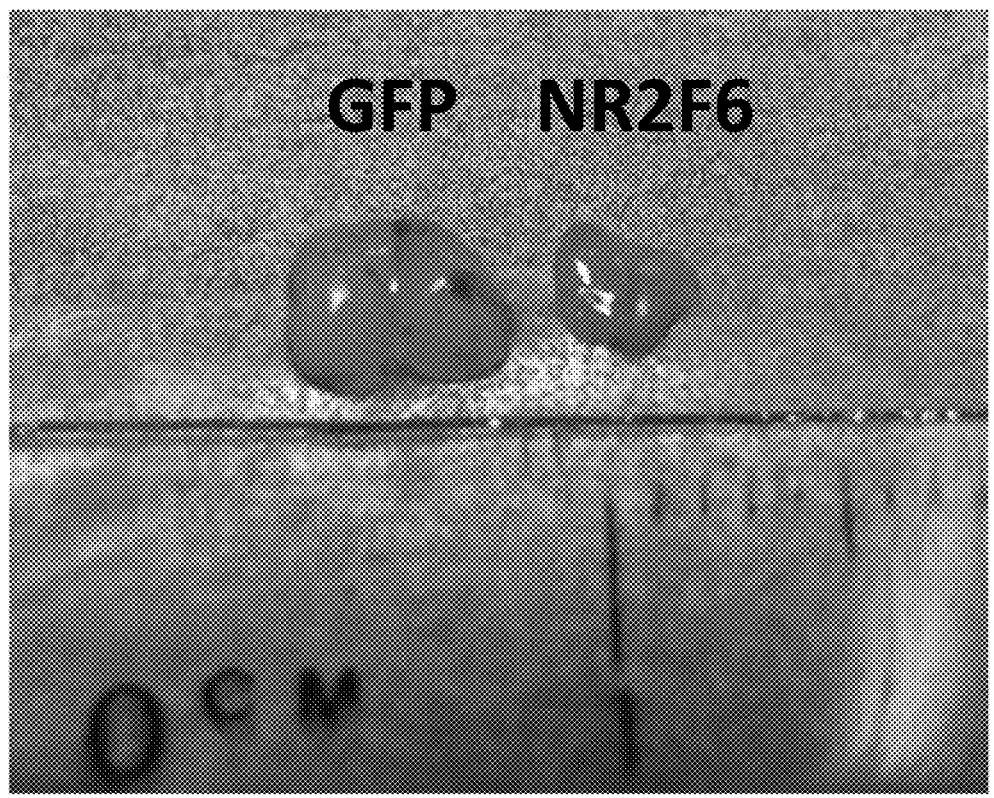
FIG. 39 shows that animals that overexpressed NR2F6 had a dramatic reduction in thymic size.
Figure 40:
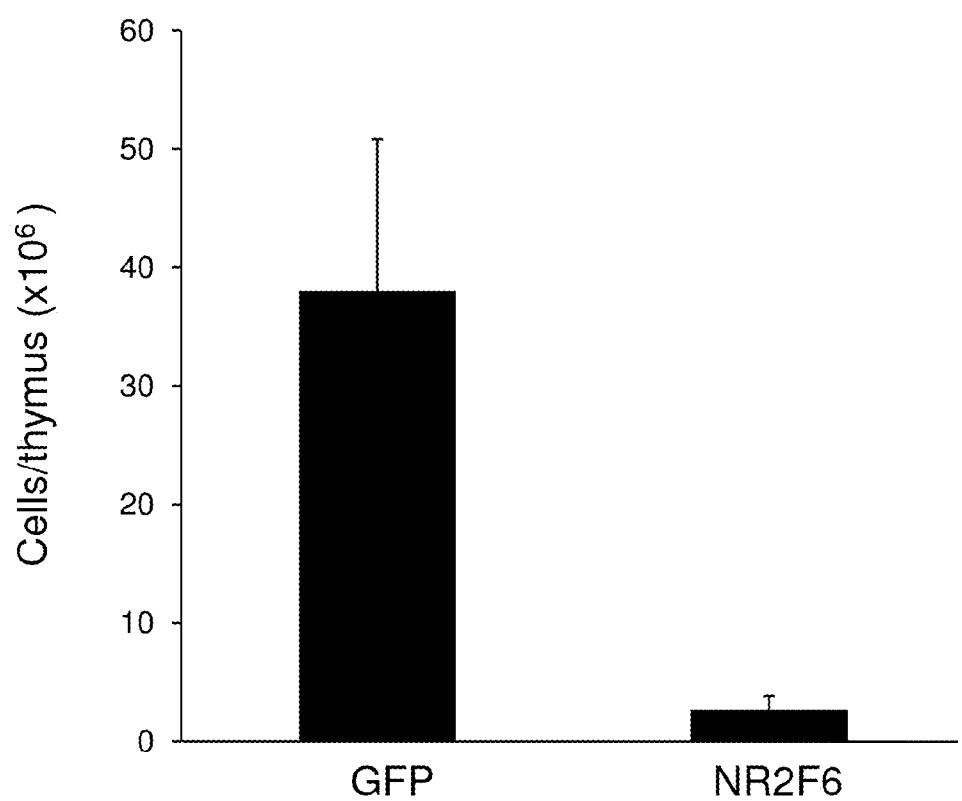
FIG. 40 shows that animals that overexpressed NR2F6 had a dramatic reduction in thymic cellularity.
Figure 41:
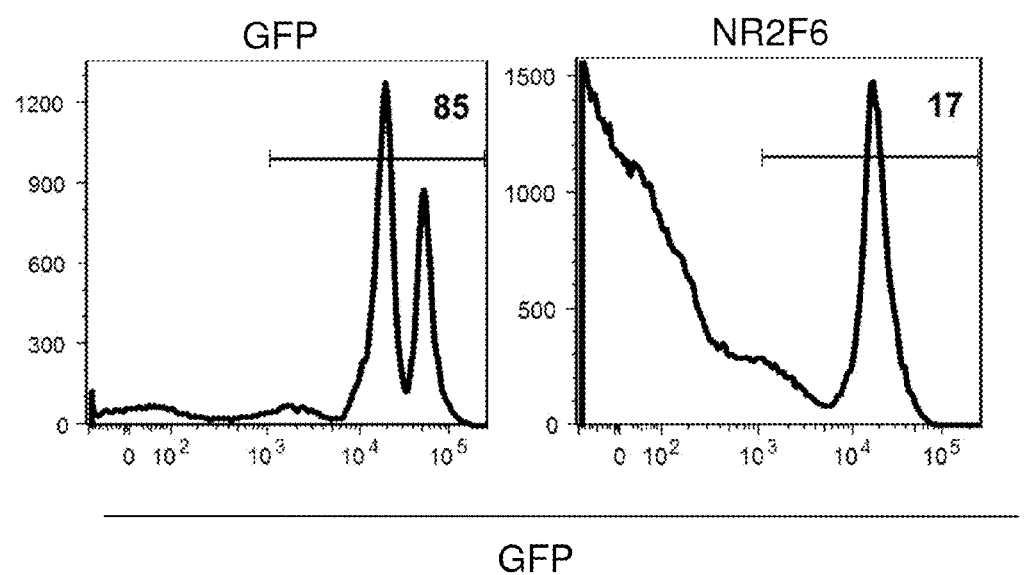
FIG. 41 shows that animals that overexpressed NR2F6 had a dramatic reduction in the expression of the NR2F6-GFP transgene.
Figure 42:
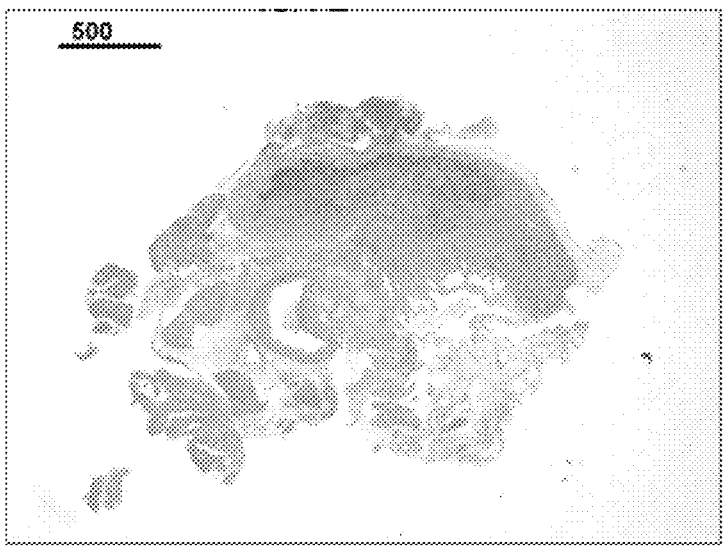
FIG. 42 shows that histological sections from animals the over-express NR2F6 have abnormal thymus, with decreased cellularity in the thymic cortex and apoptosis in the thymic medulla.
Figure 42:
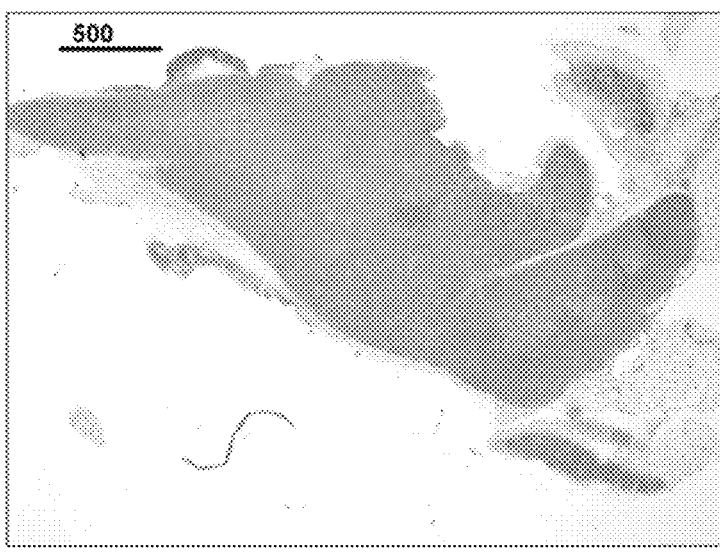
Figure 43:
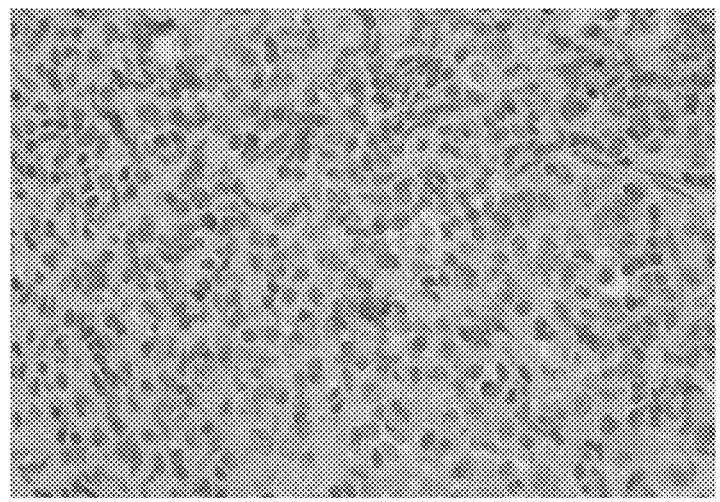
FIG. 43 shows that histological sections from animals the over-express NR2F6 have decreased cellularity in the thymic cortex.
Figure 43:
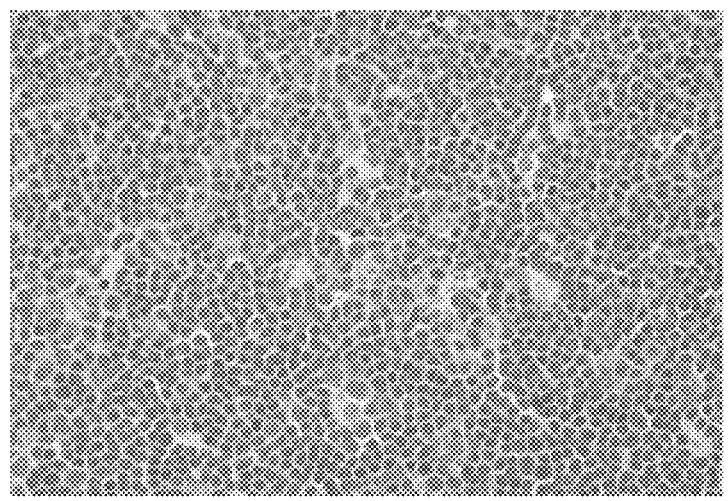
Figure 44:
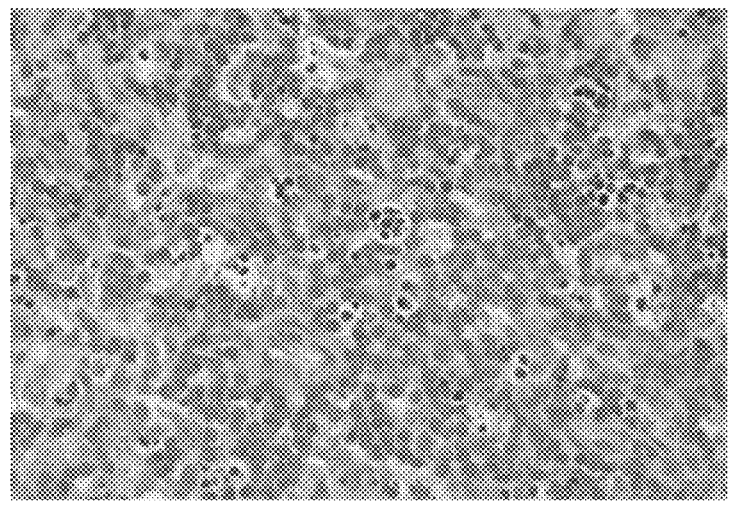
FIG. 44 shows that histological sections from animals the over-express NR2F6 have an abnormal thymic medulla with increased apoptosis.
Figure 44:
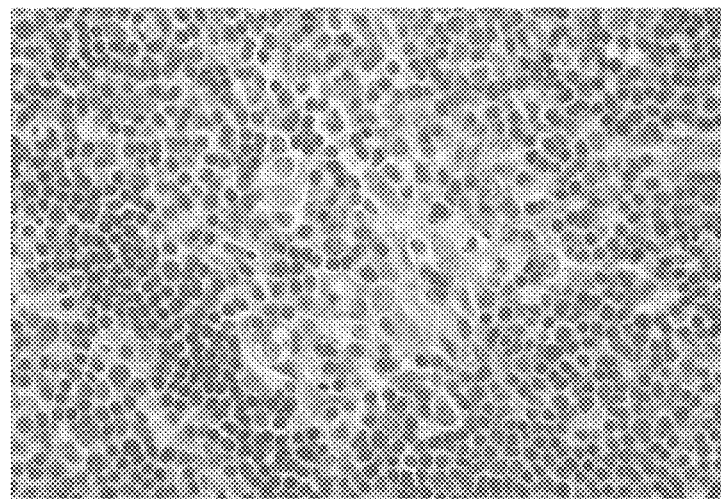
Figure 45:
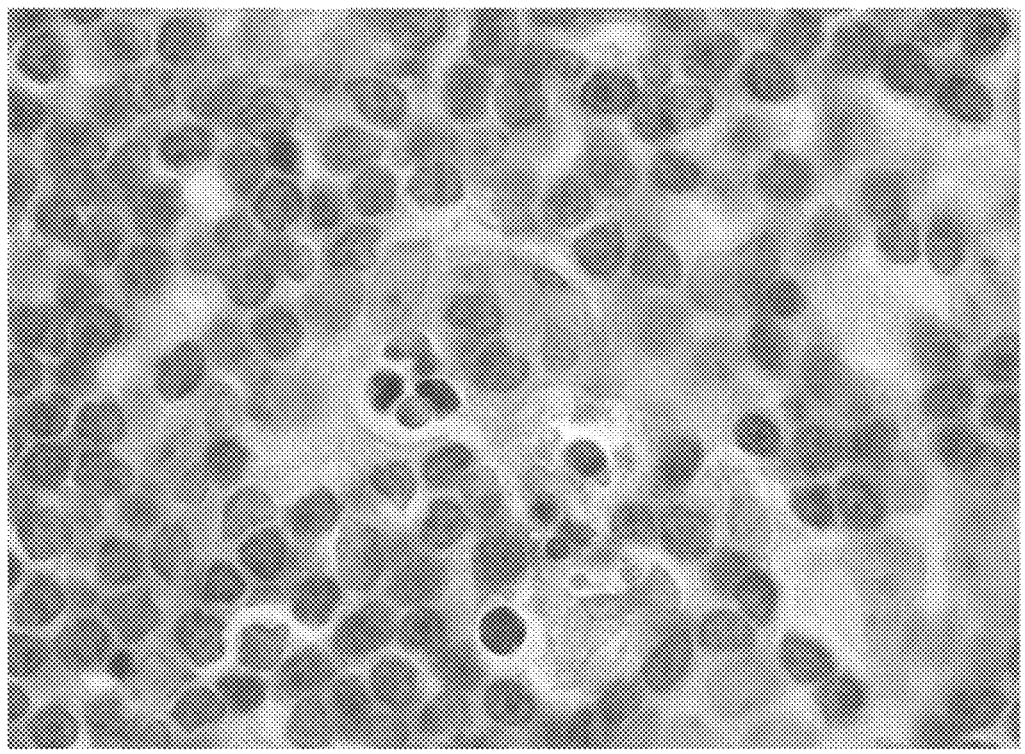
FIG. 45 shows that histological sections from animals the over-express NR2F6 have an abnormal thymic medulla with increased apoptosis.

In a second series of bone marrow transplants, cells transduced with NR2F6 or GFP were purified by fluorescence-activated cell sorting and transferred by tail vein injection into lethally irradiated recipients. Animals transplanted with NR2F6 transduced bone marrow demonstrated a striking decrease in thymus size (FIG. 39) and lower cellularity (FIG. 40). As observed in competitive transplants, these recipients demonstrated a dramatic reduction in the proportion of CD3+ cells in the thymus (FIG. 41), and CD3+ cells in the spleen, lymph nodes and peripheral blood (data not shown). Histological examination revealed effacement of the thymic cortex with a dramatic decrease in cortical lymphocytes (FIGS. 42 and 43). The medulla of NR2F6 transplant recipients showed a starry sky appearance at low power (FIG. 44), and tangible body macrophages with intra-cytoplasmic apoptotic bodies at high power (FIG. 45), indicating apoptosis. These data demonstrate that unregulated expression of NR2F6 blocks repopulation of the thymus after lethal irradiation in vivo.

In Vitro Experiments Identify a Cell Intrinsic Defect in T Cell Development

Figure 46:
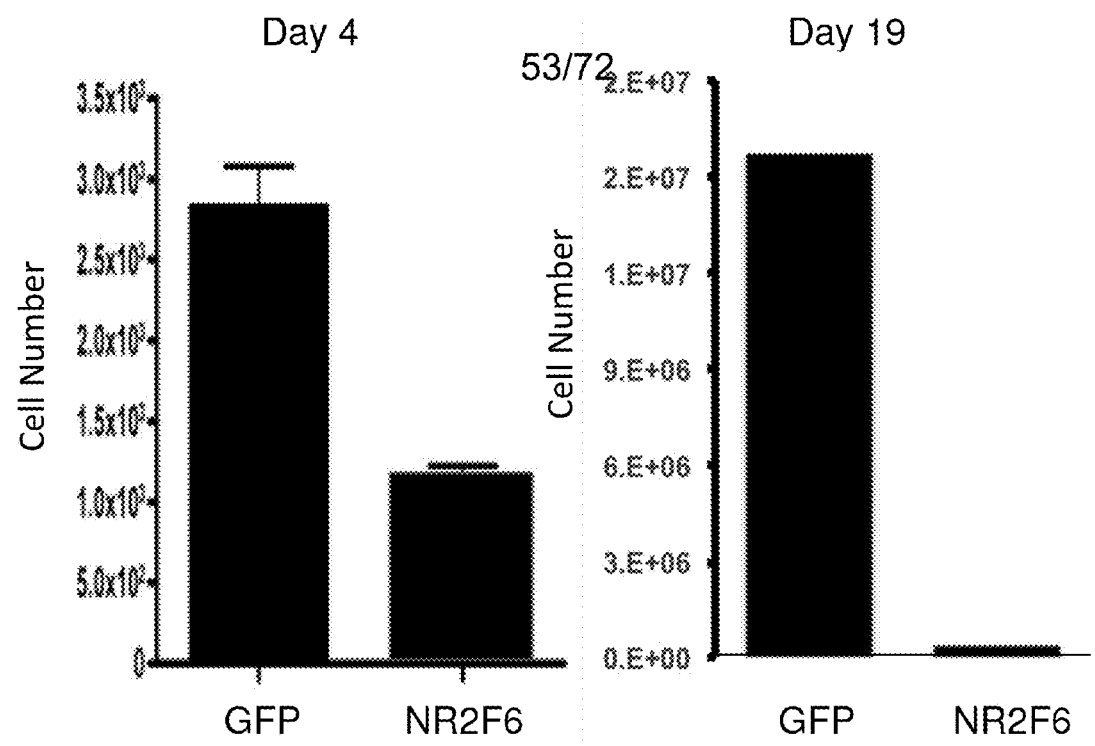
FIG. 46 shows decreased cellularity in OP9-DL1 bone marrow cultures that over-express NR2F6.
Figure 47:
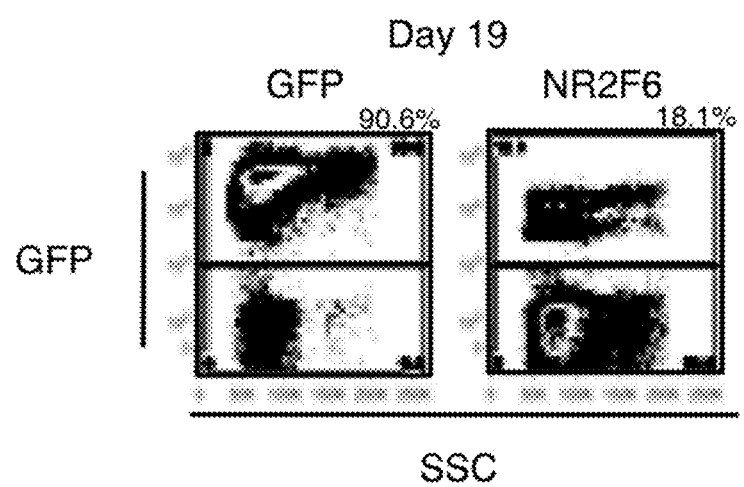
FIG. 47 shows decreased expression of the NR2F6-GFP transgene in OP9-DL1 bone marrow cultures that over-express NR2F6.

To examine further the development of T cells from NR2F6++ hematopoietic progenitors, FACS-sorted NR2F6 or GFP transduced KSL cells were differentiated into T cells in OP9-DL1 cultures. A reduction in the number of cells generated from NR2F6 BM-HSCs was observed as early as day 4 and was more distinct at day 19 (FIG. 46). The reduction in cell number was also accompanied by a reduction in the proportion of cells that expressed the NR2F6 transgene (FIG. 47) confirming that expression of NR2F6 greatly impairs T cell development in this in vitro system.

Figure 48:
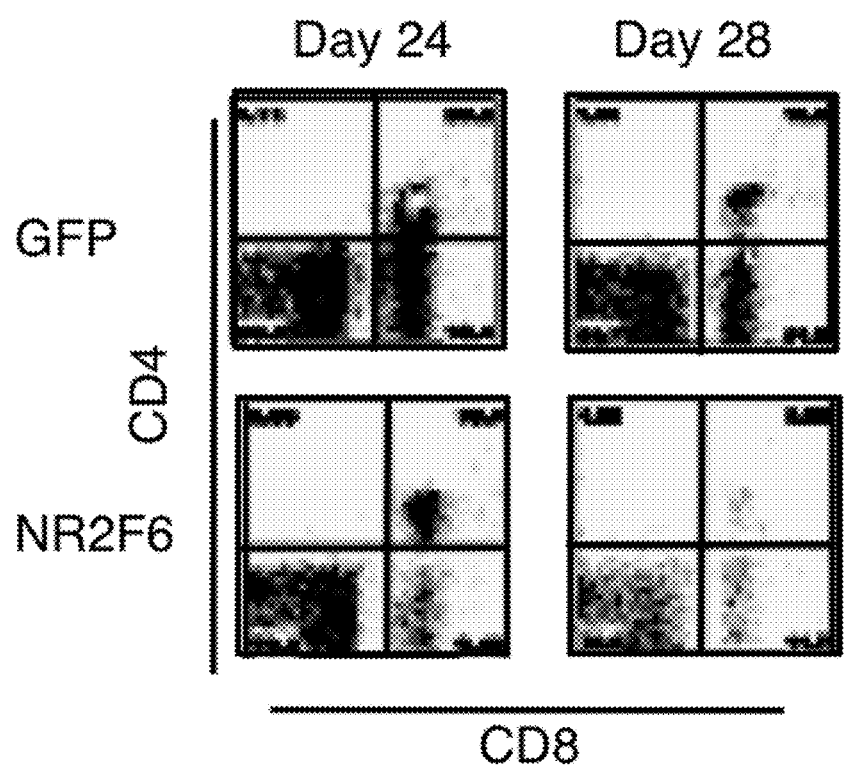
FIG. 48 shows that OP9DL-1 cultures that over-express NR2F6 have fewer double-positive, and fewer single positive immature T cells.
Figure 49:
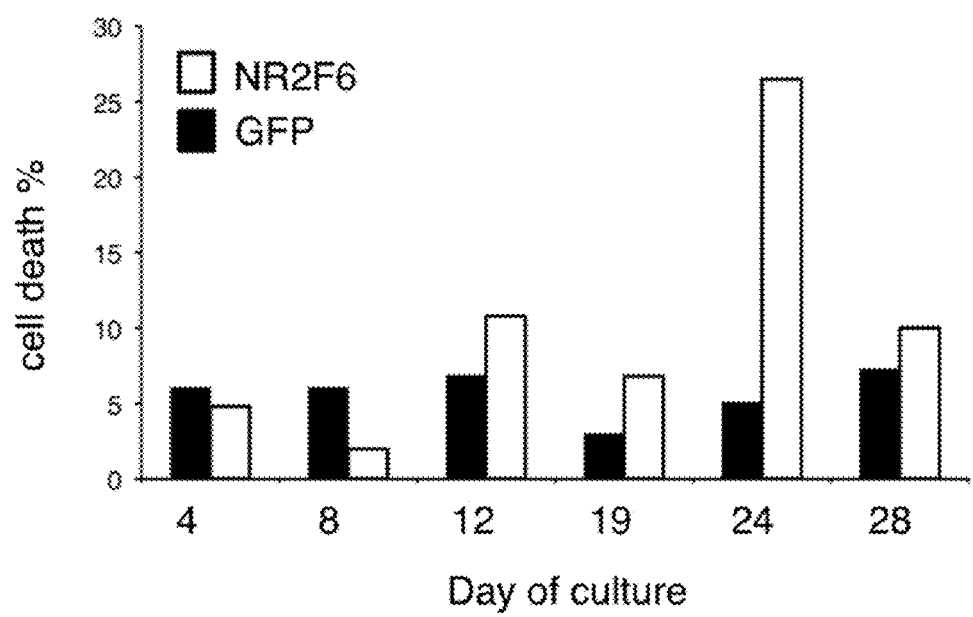
FIG. 49 shows OP9DL-1 cultures that over-express NR2F6 undergo apoptosis instead of differentiating into double-positive and single positive immature T cells.

The decrease in cell number at early time points, as early as day 4 of culture, could not be attributed to apoptosis or a block in differentiation (supplemental data) suggesting that expression of NR2F6 inhibits the proliferation of cells committed to a T cell fate. However, a block in the transition from the DN4 to double positive (DP) and single positive (SP) stage at days 24 and 28 of culture (FIG. 48), accompanied by an increase in apoptosis (FIG. 49) was observed.

These data suggest that the reduced proliferation of T cell progenitors and decreased differentiation of DPs to SPs observed upon sustained NR2F6 expression is cell intrinsic. Consequently, T cell progenitors fail to repopulate the thymus effectively and thus are unable to maintain normal cell numbers.

Discussion

NR2F6 is an orphan nuclear receptor that we have previously shown to be involved in the regulation of differentiation in myeloid leukemias. It is expressed highly in HSCs and its expression decreases as cells mature into progenitor and mature blood cells[1]. Similar to our previous observations in myeloid cells, we observed in this study that expression of NR2F6 decreases upon HSC differentiation into T cells. This decrease in the expression of NR2F6 is necessary for early thymic progenitor cells to progress towards a T cell lineage. Accordingly, in adoptive transfer experiments, enforced expression of NR2F6 prevented T cell progenitors from repopulating the thymus. In vitro experiments confirmed that NR2F6 expressing cells have severe cell-intrinsic defects in T cell development. It is known that thymic seeding progenitors enter the thymus at the corticomedullary junction. They then undergo a highly regulated process of differentiation and proliferation in the thymic cortex, including the differentiation from DN to DP cells. Subsequently, DP cells undergo the process of positive and negative selection in the cortex and the medulla respectively. Following positive selection, DP cells downregulate either CD4 or CD8 to become SP cells. Newly selected SPs migrate into medulla where they undergo the process of negative selection. Positive and negative selection ensures that auto-reactive clones are deleted from the T cell repertoire and only functional, self-restricted cells are selected and exported to the periphery. Further examination of the thymus histology in this study revealed a reduction in the cellularity of the thymic cortex, while in the medulla the decrease in cell number was associated with an increase in apoptosis. Our observation of the acellular thymic cortex is consistent with the dramatic decrease in cellularity in our OP9-DL1 cultures, suggesting that NR2F6 is necessary for proliferation and survival of early developing T cells. Furthermore, the observation of apoptotic bodies in the medulla suggests that NR2F6 downregulation is necessary for the survival of cells undergoing negative selection and that a decrease in NR2F6 expression is necessary for protection against apoptosis. It is worth noting that the increased apoptosis in the medulla may be attributed not only to deletion of auto-reactive clones, but also self-tolerant clones from the repertoire.

Furthermore, a decrease in NR2F6 expression is critical to T cell development, both in vitro and in vivo. This is demonstrated by the ability of BM-HSCs when cultured with OP9-DL1 cells to develop into all DN subsets, as well as DP and SP cells, albeit at dramatically reduced numbers, suggesting that NR2F6 does not affect differentiation per se, but other parameters such as survival and proliferation. Although we have demonstrated that this defect is observed both in vitro and in vivo, suggesting that it is a cell intrinsic phenomenon, we have not excluded the possibility that NR2F6 affects the migration of early progenitor cells to the thymus, though we do not believe that this is the case as the decrease in cell number observed in vitro is able to explain the observed decrease in cellularity in vivo.

Mechanistically, our data suggests that NR2F6 regulates the transcription program of thymocyte development. NR2F6 functions predominantly as a transcriptional repressor, inhibiting the transcriptional function of the thymic hormone receptor [36], retinoid signaling [37], and the transactivating ability of genes such as Runx1[38]. We previously reported that NR2F6 inhibits retinoic acid induced differentiation [1], suggesting that like other COUP-TFs, NR2F6 is able to inhibit retinoic acid signaling. Another distantly related orphan nuclear receptor that inhibits retinoic acid signaling is RORγt, a molecule whose precise regulation is necessary for T cell development [25, 39, 40]. It is instructive to compare the effects of NR2F6 on T cell development to those of RORγt. Akin to over-expression of NR2F6, over-expression of RORγt results in severely reduced thymic cellularity attributed to inhibition of thymocyte proliferation, and a reduction in the number of mature T cells in the periphery [25]. In addition, blocked thymocyte development was observed at the transition from DN to DP stage, similar to the stage at which we show an increase in apoptosis. Furthermore, RORγt transgenic animals show decreased CD8 SP cells, while we show a decrease in NR2F6 expression in CD8 SP cells. Given the similarities between the phenotype of NR2F6 over-expression and over-expression of the T cell master regulator RORγt, it is conceivable that the phenotype in both cases can be attributed to regulation of similar transcriptional targets.

Both NR2F6 and RORγt appear to have a role in the regulation of retinoid signaling. Nuclear receptors have long been known to influence the regulation of cell death in T cell development, the best known example being glucocorticoid-induced thymic atrophy, although glucocorticoids may also inhibit cell death in developing thymocytes [30, 41-43]. Retinoic acids are metabolites of vitamin A, that bind to receptors from the same family of molecules as the receptor that bind glucocorticoids; also, retinoic acids have a significant role in shaping decisions of cell death in T cells, serving both pro-apoptotic[41, 44, 45] and anti-apoptotic roles [27, 28, 30]. The importance of retinoid signaling in immunity is highlighted by the well-established observations of immune deficiencies in both humans and animal models of vitamin A deficiency [26, 46], with oral administration of vitamin A increasing thymic weight and cellularity in animals [47]. More specifically, retinoic acids inhibit activation induced cell death in thymocytes by inhibiting FasL production [27-30], and have been used to inhibit activation induced cell death ex vivo in T cells infected with HIV [48]. Knockout of RXRα impairs the DN to DP transition, which is seen also with RORγt overexpression as well as in our NR2F6 model. Since both NR2F6 overexpression and RORγt transgenic models show a decrease in thymocyte proliferation that could not be accounted for entirely by increased apoptosis, it is possible that these molecules may share other downstream transcriptional targets. Nevertheless, while these molecules are similar, the fact that they do not share identical roles in T cell development and activation is demonstrated by their contrasting knockout phenotypes. The RORγt knockout mouse exhibits a delay in the transition from the immature single positive (ISP; CD4$^-$/CD8$^{lo}$) to DP stage of thymocyte development accompanied by apoptosis at the DP stage caused by failure of expression of Bcl-$X_L$ [39, 40]. This results in a small thymus [49, 50] with marked reduction in numbers of DP and SP thymocytes, but an increased proportion of ISP cells. Furthermore, differentiation into Th17 cells was impaired [51]. In contrast, no appreciable differences were reported in lymphopoiesis in the NR2F6 knockout mouse. NR2F6 antagonizes activation of Th17 CD4+ T cells and NR2F6-null mice have hyper-reactive lymphocytes and are hyper-susceptible to Th17-dependent experimental autoimmune encephalomyelitis [20]. This effect of NR2F6 is mediated directly by interference with DNA binding by the NF-AT:AP-1 transcription factor complex, and is dependent on NR2F6 phosphorylation at residue Ser-83.

While the dramatic effects that we observed upon over-expression of NR2F6 may at first glance appear at odds with the lack of phenotype reported in the knockout animal, we conjecture that in lymphoid progenitors NR2F6 functions as a transcriptional repressor preventing the activation of pathways necessary for T cell survival, proliferation and possibly differentiation. Hence, in the absence of NR2F6, repression of those pathways responsible for differentiation would not occur, therefore resulting in the observed phenotype. It will be interesting to elucidate these NR2F6 governed molecular pathways.

Of course, there are implicit limitations to the over-expression model system, and hence one must evaluate the notion of whether the effects of over-expression of NR2F6 on thymocyte development can be attributed to the phenomenon of squelching, wherein the observations described can be attributed to non-specific effects due to binding of NR2F6 to cofactors of other transcription factors, rather than via regulation of transcription of specific target genes by NR2F6. We feel that this is an unlikely scenario because of the specificity of the observed effects to the T cell lineage: over-expression of NR2F6 in the animals described herein does not impede the proliferation or development of B cells nor does it decrease the numbers of KSL cells (data not shown). Not only are the observations we described specific to the T cell lineage but they are also specific to precise phenomena in T cell development. Taken together, these data identify the orphan nuclear receptor NR2F6 as a novel negative regulator of T cell lymphopoiesis that acts at multiple steps in the developmental cascade, and demonstrates that down-regulation of NR2F6 is necessary for the survival and proliferation of T cell progenitors.

REFERENCES

[1] Ichim C V, Atkins H L, Iscove N N, Wells R A. Identification of a role for the nuclear receptor NR2F6 in the maintenance of clonogenic status within the leukemia cell hierarchy. Leukemia. 2011; 25:1687-1696.

[2] Mettler U, Vogler G, Urban J. Timing of identity: spatiotemporal regulation of hunchback in neuroblast lineages of *Drosophila* by Seven-up and Prospero. Development. 2006; 133:429-437.

[3] Qiu Y, Pereira F A, DeMayo F J, Lydon J P, Tsai S Y, Tsai M J. Null mutation of mCOUP-TFI results in defects in morphogenesis of the glossopharyngeal ganglion, axonal projection, and arborization. Genes Dev. 1997; 11:1925-1937.

[4] Zhou C, Qiu Y, Pereira F A, Crair M C, Tsai S Y, Tsai M J. The nuclear orphan receptor COUP-TFI is required for differentiation of subplate neurons and guidance of thalamocortical axons. Neuron. 1999; 24:847-859.

[5] Zhou C, Tsai S Y, Tsai M J. COUP-TFI: an intrinsic factor for early regionalization of the neocortex. Genes Dev. 2001; 15:2054-2059.

[6] You L R, Lin F J, Lee C T, DeMayo F J, Tsai M J, Tsai S Y. Suppression of Notch signaling by the COUP-TFII transcription factor regulates vein identity. Nature. 2005; 435: 98-104.

[7] Ciszek B, Skubiszewska D, Ratajska A. The anatomy of the cardiac veins in mice. J. Anat. 2007; 211:53-63.

[8] Lee S, Kang J, Yoo J, et al. Prox1 physically and functionally interacts with COUP-TFII to specify lymphatic endothelial cell fate. Blood. 2009; 113:1856-1859.

[9] Lin F J, Chen X, Qin J, Hong Y K, Tsai M J, Tsai S Y. Direct transcriptional regulation of neuropilin-2 by COUP-TFII modulates multiple steps in murine lymphatic vessel development. J Clin Invest. 2010; 120:1694-1707.

[10] Yamazaki T, Yoshimatsu Y, Morishita Y, Miyazono K, Watabe T. COUP-TFII regulates the functions of Prox1 in lymphatic endothelial cells through direct interaction. Genes Cells. 2009; 14:425-434.

[11] Qin J, Tsai M J, Tsai S Y. Essential roles of COUP-TFII in Leydig cell differentiation and male fertility. PLoS One. 2008; 3:e3285.

[12] Petit F G, Jamin S P, Kurihara I, et al. Deletion of the orphan nuclear receptor COUP-TFII in uterus leads to placental deficiency. Proc Natl Acad Sci USA. 2007; 104: 6293-6298.

[13] Li L, Xie X, Qin J, et al. The nuclear orphan receptor COUP-TFII plays an essential role in adipogenesis, glucose homeostasis, and energy metabolism. Cell Metab. 2009; 9:77-87.

[14] Okamura M, Kudo H, Wakabayashi K, et al. COUP-TFII acts downstream of Wnt/beta-catenin signal to silence PPARgamma gene expression and repress adipogenesis. Proc Natl Acad Sci USA. 2009; 106:5819-5824.

[15] Xu Z, Yu S, Hsu C H, Eguchi J, Rosen E D. The orphan nuclear receptor chicken ovalbumin upstream promoter-transcription factor II is a critical regulator of adipogenesis. Proc Natl Acad Sci USA. 2008; 105:2421-2426.

[16] Kim B J, Takamoto N, Yan J, Tsai S Y, Tsai M J. Chicken Ovalbumin Upstream Promoter-Transcription Factor II (COUP-TFII) regulates growth and patterning of the postnatal mouse cerebellum. Dev Biol. 2009; 326:378-391.

[17] Satoh S, Tang K, Iida A, et al. The spatial patterning of mouse cone opsin expression is regulated by bone morphogenetic protein signaling through downstream effector COUP-TF nuclear receptors. J. Neurosci. 2009; 29:12401-12411.

[18] Tang K, Xie X, Park J I, Jamrich M, Tsai S, Tsai M J. COUP-TFs regulate eye development by controlling factors essential for optic vesicle morphogenesis. Development. 2010; 137:725-734.

[19] Warnecke M, Oster H, Revelli J P, Alvarez-Bolado G, Eichele G. Abnormal development of the locus coeruleus in Ear2(Nr2f6)-deficient mice impairs the functionality of the forebrain clock and affects nociception. Genes Dev. 2005; 19:614-625.

[20] Hermann-Kleiter N, Gruber T, Lutz-Nicoladoni C, et al. The nuclear orphan receptor NR2F6 suppresses lymphocyte activation and T helper 17-dependent autoimmunity. Immunity. 2008; 29:205-216.

[21] Zhu X G, Park K S, Kaneshige M, et al. The orphan nuclear receptor NR2F6 is a negative coregulator for thyroid hormone nuclear receptor function. Mol Cell Biol. 2000; 20:2604-2618.

[22] Ladias J A. Convergence of multiple nuclear receptor signaling pathways onto the long terminal repeat of human immunodeficiency virus-1. J Biol. Chem. 1994; 269:5944-5951.

[23] Ivanov I I, Zhou L, Littman D R. Transcriptional regulation of Th17 cell differentiation. Semin Immunol. 2007; 19:409-417.

[24] Ortiz M A, Piedrafita F J, Pfahl M, Maki R. TOR: a new orphan receptor expressed in the thymus that can modulate retinoid and thyroid hormone signals. Mol. Endocrinol. 1995; 9:1679-1691.

[25] He Y W, Beers C, Deftos M L, Ojala E W, Forbush K A, Bevan M J. Down-regulation of the orphan nuclear receptor ROR gamma t is essential for T lymphocyte maturation. J. Immunol. 2000; 164:5668-5674.

[26] Szondy Z, Reichert U, Fésüs L. Retinoic acids regulate apoptosis of T lymphocytes through an interplay between RAR and RXR receptors. Cell Death Differ. 1998; 5:4-10.

[27] Bissonnette R P, Brunner T, Lazarchik S B, et al. 9-cis retinoic acid inhibition of activation-induced apoptosis is mediated via regulation of fas ligand and requires retinoic acid receptor and retinoid X receptor activation. Mol Cell Biol. 1995; 15:5576-5585.

[28] Yang Y, Vacchio M S, Ashwell J D. 9-cis-retinoic acid inhibits activation-driven T cell apoptosis: implications for retinoid X receptor involvement in thymocyte development. Proc Natl Acad Sci USA. 1993; 90:6170-6174.

[29] Yang Y, Minucci S, Ozato K, Heyman R A, Ashwell J D. Efficient inhibition of activation-induced Fas ligand up-regulation and T cell apoptosis by retinoids requires occupancy of both retinoid X receptors and retinoic acid receptors. J Biol. Chem. 1995; 270:18672-18677.

[30] Yang Y, Merćep M, Ware C F, Ashwell J D. Fas and activation-induced Fas ligand mediate apoptosis of T cell hybridomas: inhibition of Fas ligand expression by retinoic acid and glucocorticoids. J Exp Med. 1995; 181:1673-1682.

[31] Ichim C V, Atkins H L, Iscove N N, Wells R A. Identification of a role for the nuclear receptor NR2F6 in the maintenance of clonogenic status within the leukemia cell hierarchy. Leukemia.

[32] Ichim C V, Wells R A. Generation of high-titer viral preparations by concentration using successive rounds of ultracentrifugation. J Transl Med. 2011; 9:137.

[33] Schmitt T M, Zúñiga-Pflücker J C. Induction of T cell development from hematopoietic progenitor cells by delta-like-1 in vitro. Immunity. 2002; 17:749-756.

[34] Schmitt T M, Zuniga-Pflucker J C. Induction of T cell development from hematopoietic progenitor cells by delta-like-1 in vitro. Immunity. 2002; 17:749-756.

[35] Holmes R, Zuniga-Pflucker J C. The OP9-DL1 system: generation of T lymphocytes from embryonic or hematopoietic stem cells in vitro. Cold Spring Harb Protoc. 2009; 2009:pdb prot5156.

[36] Zhu X G, Park K S, Kaneshige M, et al. The orphan nuclear receptor NR2F6 is a negative coregulator for thyroid hormone nuclear receptor function. Mol Cell Biol. 2000; 20:2604-2618.

[37] Ladias J A. Convergence of multiple nuclear receptor signaling pathways onto the long terminal repeat of human immunodeficiency virus-1. J Biol. Chem. 1994; 269:5944-5951.

[38] Ahn M Y, Huang G, Bae S C, Wee H J, Kim W Y, Ito Y. Negative regulation of granulocytic differentiation in the myeloid precursor cell line 32Dcl3 by NR2F6, a mammalian homolog of *Drosophila* seven-up, and a chimeric leukemogenic gene, AML1/ETO. Proc Natl Acad Sci USA. 1998; 95:1812-1817.

[39] Kurebayashi S, Ueda E, Sakaue M, et al. Retinoid-related orphan receptor gamma (RORgamma) is essential for lymphoid organogenesis and controls apoptosis during thymopoiesis. Proc Natl Acad Sci USA. 2000; 97:10132-10137.

[40] Sun Z, Unutmaz D, Zou Y R, et al. Requirement for RORgamma in thymocyte survival and lymphoid organ development. Science. 2000; 288:2369-2373.

[41] Iwata M, Mukai M, Nakai Y, Iseki R. Retinoic acids inhibit activation-induced apoptosis in T cell hybridomas and thymocytes. J. Immunol. 1992; 149:3302-3308.

[42] Zacharchuk C M, Merćep M, Chakraborti P K, Simons S S, Ashwell J D. Programmed T lymphocyte death. Cell activation- and steroid-induced pathways are mutually antagonistic. J. Immunol. 1990; 145:4037-4045.

[43] Zacharchuk C M, Merćep M, Ashwell J D. Thymocyte activation and death: a mechanism for molding the T cell repertoire. Ann N Y Acad. Sci. 1991; 636:52-70.

[44] Fésüs L, Szondy Z, Uray I. Probing the molecular program of apoptosis by cancer chemopreventive agents. J Cell Biochem Suppl. 1995; 22:151-161.

[45] Szondy Z. Methylprednisolone and 2-chloroadenosine induce DNA fragmentation at different stages of human T lymphocyte development. Immunol Lett. 1997; 58:59-65.

[46] West K P, Howard G R, Sommer A. Vitamin A and infection: public health implications. Annu Rev Nutr. 1989; 9:63-86.

[47] Selfter E, Rettura G, Levenson S M. Decreased resistance of C3H/HeHa mice to C3HBA tumor transplants; increased resistance due to supplemental vitamin A. J Natl Cancer Inst. 1981; 67:467-472.

[48] Yang Y, Bailey J, Vacchio M S, Yarchoan R, Ashwell J D. Retinoic acid inhibition of ex vivo human immunodeficiency virus-associated apoptosis of peripheral blood cells. Proc Natl Acad Sci USA. 1995; 92:3051-3055.

[49] Dzhagalov I, Giguere V, He Y W. Lymphocyte development and function in the absence of retinoic acid-related orphan receptor alpha. J. Immunol. 2004; 173:2952-2959.

[50] Trenkner E, Hoffmann M K. Defective development of the thymus and immunological abnormalities in the neurological mouse mutation "staggerer". J. Neurosci. 1986; 6:1733-1737.

[51] Ivanov I I, McKenzie B S, Zhou L, et al. The orphan nuclear receptor RORgammatg directs the differentiation program of proinflammatory IL-17+ T helper cells. Cell. 2006; 126:1121-1133.

Results

Figure 50:
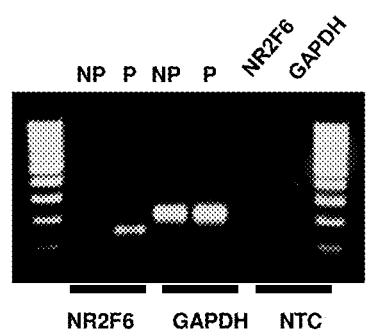
FIG. 50 shows that expression of NR2F6 correlates with clonogenic leukemia cells. NP—no proliferative ability (were not able to divide) or P—proliferative ability (were able to divide).

Expression of NR2F6 was assessed in OCI-AML4 single cells with either NP—no proliferative ability (were not able to divide) or P—proliferative ability (were able to divide). FIG. 50 shows that expression of NR2F6 correlates with clonogenic leukemia cells. OCI/AML-4 clonal siblings were used as reporters of the growth ability of a sibling cell that was sampled for global RT-PCR. Cells were plated at limiting dilutions. Localized clusters of four cells were identified and micromanipulated such that three of the constituent cells were placed separately into individual microtiter wells containing growth medium and a feeder layer of OP9 cells, while the fourth cell was lysed and processed for global RT-PCR. The cells in each culture well were counted at 2-3 day intervals until growth stopped. In this manner, cDNA was generated from 42 individual OCI/AML-4 cells for which the growth profile of clonal siblings had also been determined. Semi-quantitative PCR on pooled cDNA from cells with and without proliferative ability validated that NR2F6 is expressed in clonogenic leukemia cells greater than in non-clonogenic leukemia cells.

Figure 58:
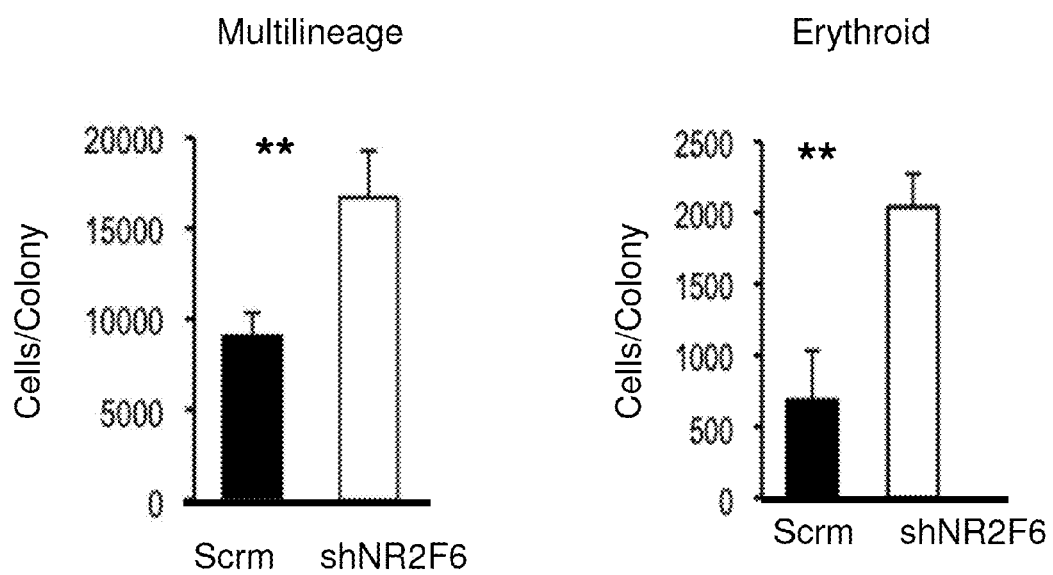
FIG. 58 shows that inhibition of NR2F6 with shRNA promotes differentiation of hematopoietic progenitor cells indicated by the increase in the size of colonies grown in methylcellulose with cytokines that promote multilineage progenitor cell differentiation or erthyroid progenitor cell differentiation.
Figure 59:
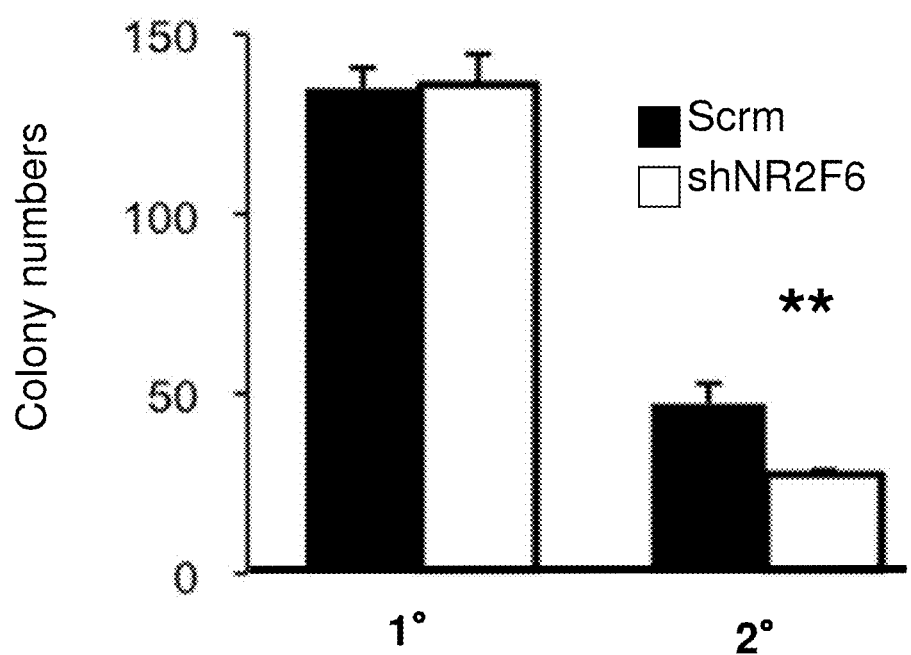
FIG. 59 shows that inhibition of NR2F6 inhibits the self-renewal of hematopoietic stem cells shown here by the decrease in the serial replating ability of colonies grown in methylcellulose with cytokines that promote multilineage cell differentiation.

We assessed the effects of silencing of EAR-2 expression on colony formation in vitro. While silencing of EAR-2 did not significantly reduce the number of colony forming units, it did significantly increase the colony size FIG. 58, Next, we tested whether silencing of EAR-2 reduced the clonogenicity and self-renewal of bone marrow cells. In replating experiments we observed a significant decrease in secondary colonies in cells in which EAR-2 expression was silenced FIG. 59. Taken together, these results show that EAR-2 is a negative regulator of hematopoietic differentiation in vitro.

Figure 60:
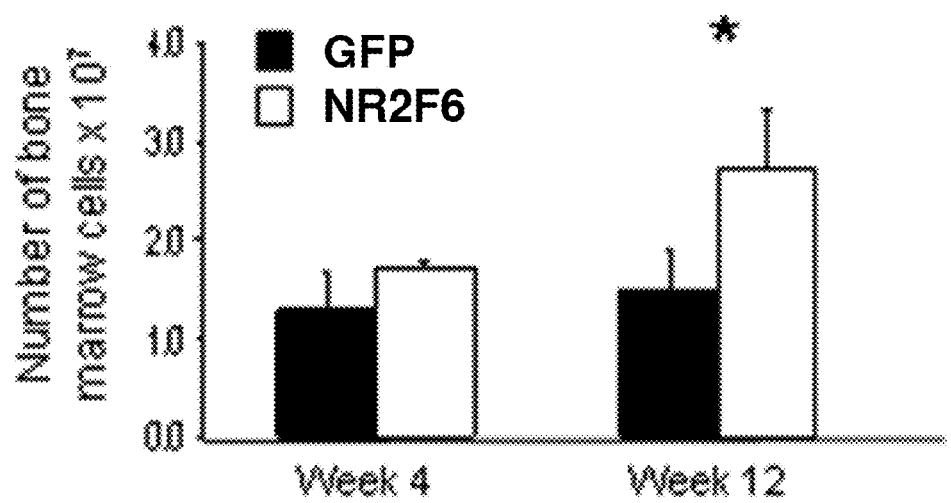
FIG. 60 shows that expression of NR2F6 in a chimerical bone marrow mouse model (30% NR2F6 transduced, 70% untransduced cells) increases the cellularity of the animal's bone marrow creating a condition of hyperplasia.
Figure 61:
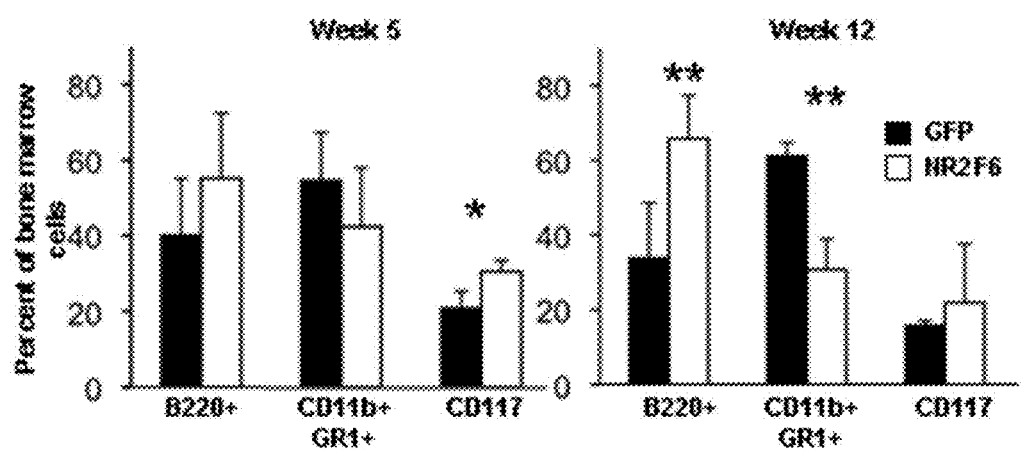
FIG. 61 shows that modulating the expression of NR2F6 in a chimerical bone marrow mouse model (30% NR2F6 transduced, 70% untransduced cells) induces the differentiation of bone marrow cells along certain cell lineages (B-cells), while inhibiting the differentiation of other cell lineages (myeloid cell lineages).
Figure 62:
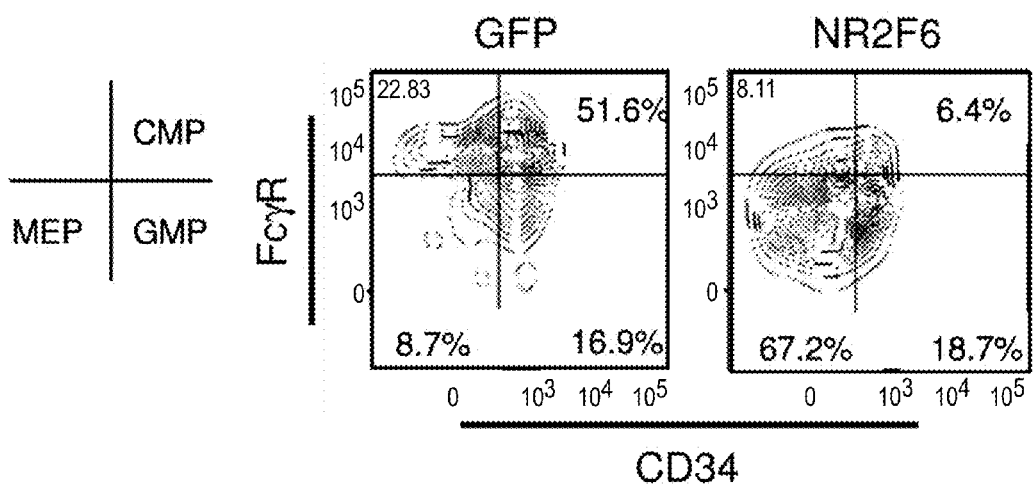
FIG. 62 shows that modulating the expression of NR2F6 in a chimerical bone marrow mouse model (30% NR2F6 transduced, 70% untransduced cells) causes a block in the ability of hematopoietic stem cells to differentiate into the megakaryocyte-erythroid progenitor cell (MEP) while decreasing the size of the common myeloid progenitor cell population as well as the granulocyte-monocyte progenitor (GMP) cell population.
Figure 63:
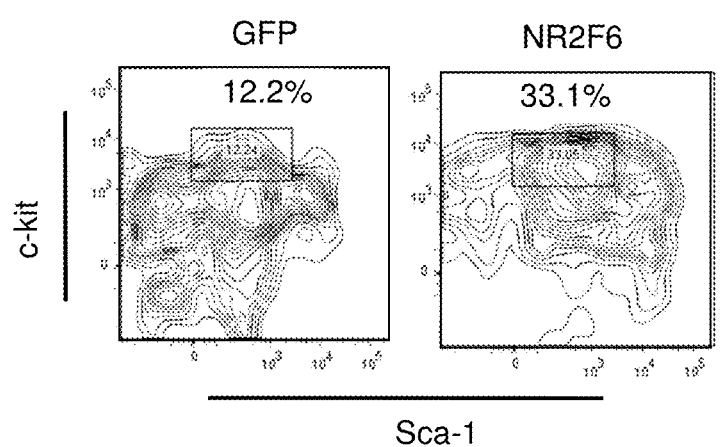
FIG. 63 shows that modulating the expression of NR2F6 in a chimerical bone marrow mouse model (30% NR2F6 transduced, 70% untransduced cells) increases hematopoietic stem cell differentiation into common lymphoid progenitor cells.
Figure 64:
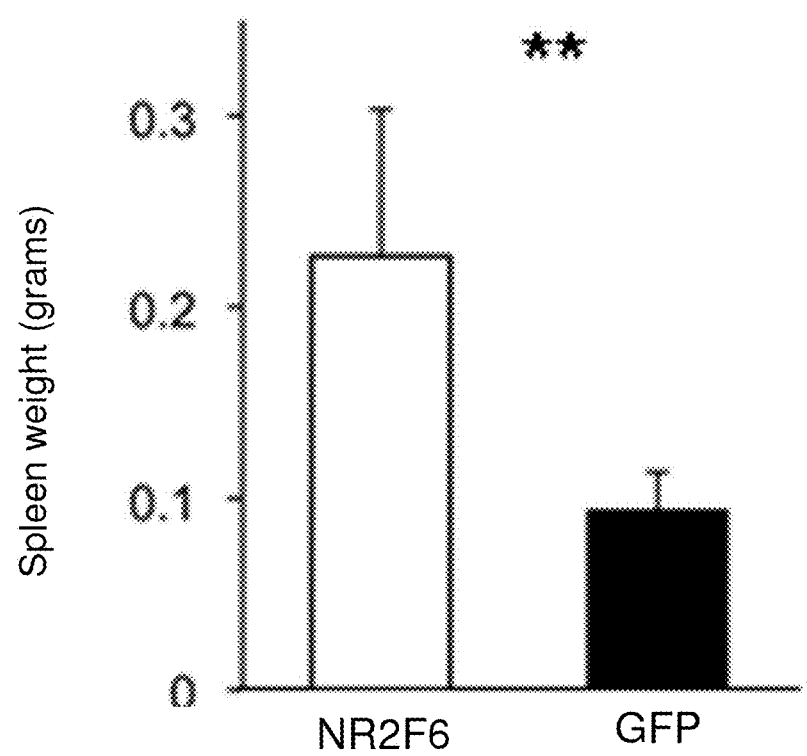
FIG. 64 shows that over-expression of NR2F6 in a mouse transplantation model where 100% of cells are transduced with NR2F6 induces splenomegaly in mammals in vivo.
Figure 65:
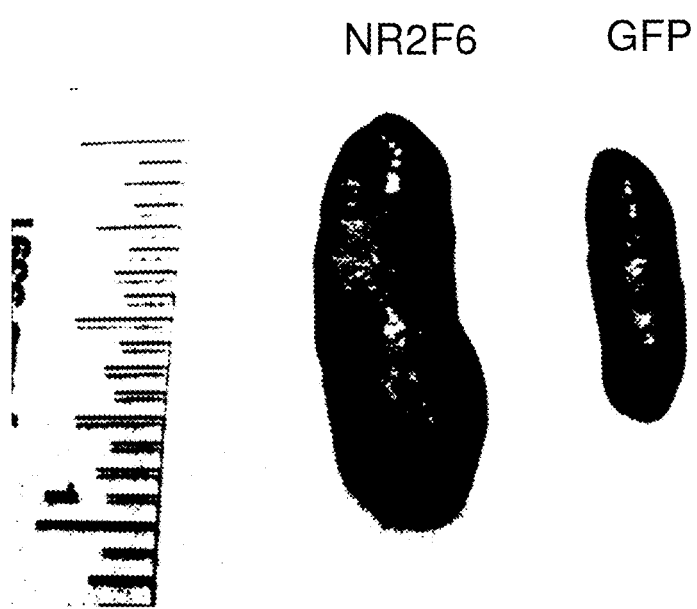
FIG. 65 shows that over-expression of NR2F6 in a mouse transplantation model where 100% of cells are transduced with NR2F6 induces splenomegaly in mammals in vivo.

To investigate the effects of exogenous expression of EAR-2 on hematopoiesis in vivo, we performed adoptive transfer of EAR-2-transduced hematopoietic cells into lethally irradiated syngeneic recipients in a competitive repopulation model. We observed that expression of NR2F6 in a chimerical bone marrow mouse model (30% NR2F6 transduced, 70% untransduced cells) increases the cellularity of the animal's bone marrow creating a condition of hyperplasia (FIG. 60). To assess the role of EAR-2 on hematopoietic lineage specification and differentiation in vivo we analyzed the composition of recipient bone marrow using flow cytometry. We observed a significant increase in the proportion of B cells (B220+ cells) (FIG. 61), as well as a significant decrease in the proportion of granulocytes (CD11b+, GR-1+ cells) in the GFP portion of bone marrow in recipients that overexpressed EAR-2 (FIG. 61). These data suggest that modulating NR2F6 function can be a method of directing the cell fate decisions of stem cells to induce them to differentiate along specific lineages. We further went on to analyze the distribution of bone marrow cells in progenitor cell subsets observing an accumulation of megakaryocyte-erythroid progenitor cells (MEPs) and a decrease in common myeloid progenitor cells (CMPs) in the bone marrow of animals transplanted with EAR-2 transduced bone marrow (FIG. 62), as well as an increase in common lymphoid progenitor cells (CLP) (FIG. 63). These data suggest that modulating NR2F6 function can be a method of directing the cell fate decisions of stem cells to induce them to differentiate along specific lineages. In another experimental series lethally irradiated C57Bl/6 mice transplanted with bone marrow graft sorted for expression of the EAR-2 transgene developed a rapidly progressing leukemia. In an initial cohort of 12 recipients (6 for each experimental group) we observed ill health early in the recipients of EAR-2-transduced grafts. Whereas the six GFP recipients remained healthy throughout the experiment, four of six EAR-2 recipients became moribund within five weeks of transplantation. Infiltration by myeloid cells was also seen in the spleen. In EAR-2 recipients, there was enlargement of the spleen (FIG. 64 and FIG. 65). These data suggest that modulation of NR2F6 can induce splenomegaly and hence modulating NR2F6 function can be a method of treating patients who suffer from splenomegaly.

Figure 51:
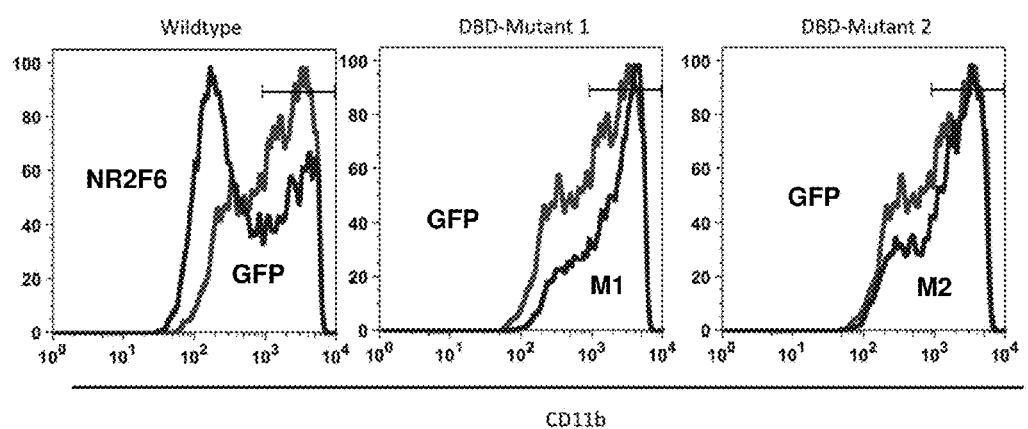
FIG. 51 shows that NR2F6 functions to inhibit differentiation in a DNA binding dependant manner in 32D hematopoietic cells.
Figure 52:
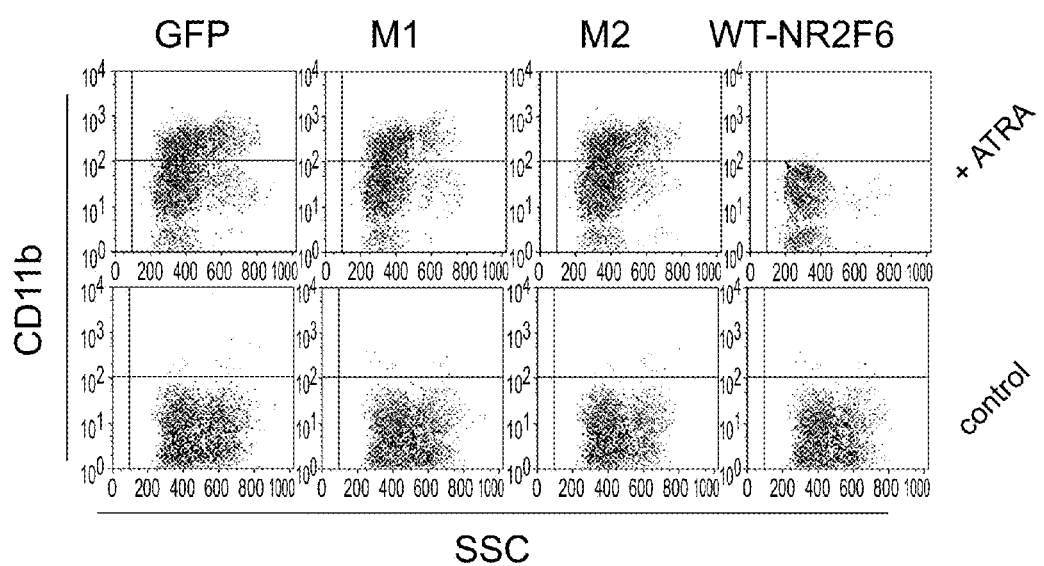
FIG. 52 shows that NR2F6 functions to inhibit differentiation in a DNA binding dependant manner in human U937 leukemia cells.

Nuclear receptors may possess DNA binding dependent as well as DNA binding independent function. To examine whether the ability of EAR-2 to inhibit differentiation is DNA-binding dependent we used constructs of EAR-2 with mutations that disrupt the DNA binding domain, specifically in the P-box (M1) and D-box (M2) of the zinc finger domains. We observed that mutation of either the P-box or the D-box abrogated the ability of EAR-2 to inhibit differentiation of 32Dcl3 cells (FIG. 51) and human leukemia U937 cells (FIG. 52) suggesting that this phenotype is dependent on the DNA-binding ability of EAR-2 and establishing that this effect is not simply a squelching phenomenon resulting from sequestration of nuclear receptor cofactors by EAR-2. These data establish the proof of the principle that a compound that block's the ability of NR2F6 to bind to DNA can be used as a drug that induces differentiation of normal hematopoietic cells or to induce differentiation in human leukemias.

Figure 53:
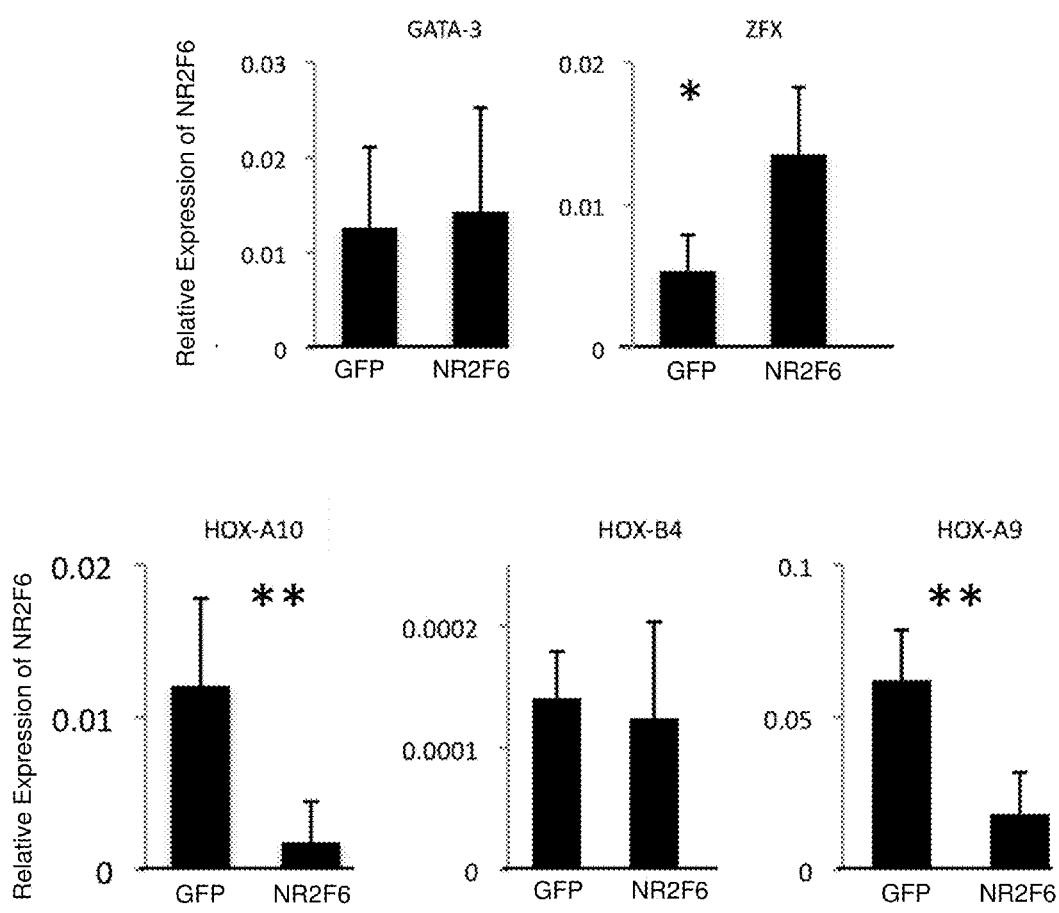
FIG. 53 shows that NR2F6 functions to modulate expression of genes associated with cancer and maintenance of the stem cell phenotype in KSL hematopoietic stem cells. The figure shows that overexpression of NR2F6 modulate expressions of the gene ZFX, HOX-A10 and HOX-A9.
Figure 54:
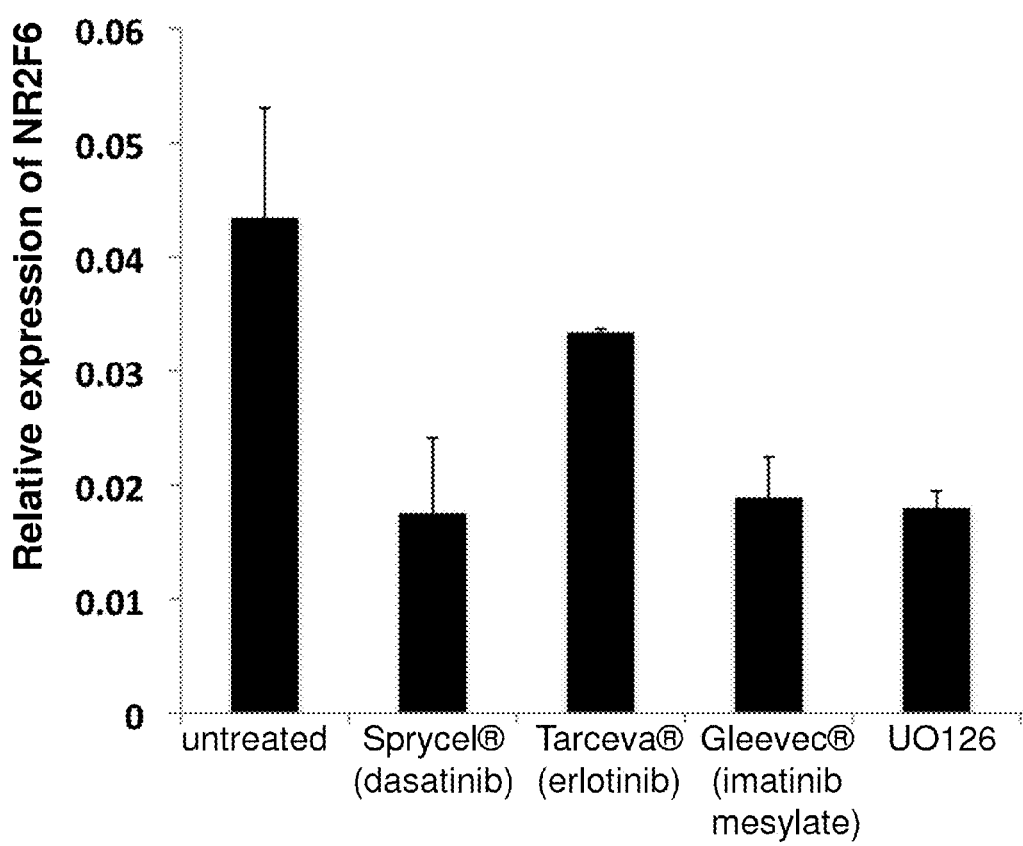
FIG. 54 shows treatment of U937 human leukemia cells with various tyrosine kinase inhibitor drugs decreases mRNA expression of NR2F6.

Given that EAR-2 function is consistent at least partially with that of a transcriptional repressor, we wished to identify changes in gene expression associated with expression of EAR-2 in early hematopoietic cells. Analysis of expression of select candidate genes associated with HSCs in mice (n=11) revealed reduced expression of HOX-A10 and HOX-A9 in bone marrow KSL bone marrow stem cells that overexpress EAR-2, while expression of ZFX is significantly increased (FIG. 53). While increased expression of HOXA9 is associated with proliferation of a specific type of leukemia, knockdown of HOXA9 increases self-renewal and prevents differentiation (1). Furthermore, downregulation of HOX-A9 is observed in several types of cancer (2-13). ZFX is associated with maintenance of self-renewal ability in embryonic and hematopoietic stem cells (14). These observations lead to a model in which EAR-2 represses hematopoietic differentiation by acting as a DNA-specific transcriptional repressor and altering the Hox program in the HSC. This experiment establishes proof of the principle that a compound that can modulate NR2F6 is able to alter expression of genes associated with cancer cell growth, stem cell self-renewal and differentiation. We then asked whether EAR-2 could be involved in leukemia drug resistance. Some types of leukemia can be treated with tyrosine kinase inhibitor drugs. We show that tyrosine kinase inhibitor drugs act by decreasing expression of NR2F6 (FIG. 54). This suggests that decreased expression of NR2F6 may be necessary for the function of tyrosine kinase inhibitors and that resistance to these drugs could come about by dysregulated expression of NR2F6. Therefore, compounds that modulate the function of NR2F6 could be used in combination with tyrosine kinase inhibitors to improve their function and treat resistance that can be mediated by deregulated expression of EAR-2 as we have previously shown in cancer patients.

Figure 55:
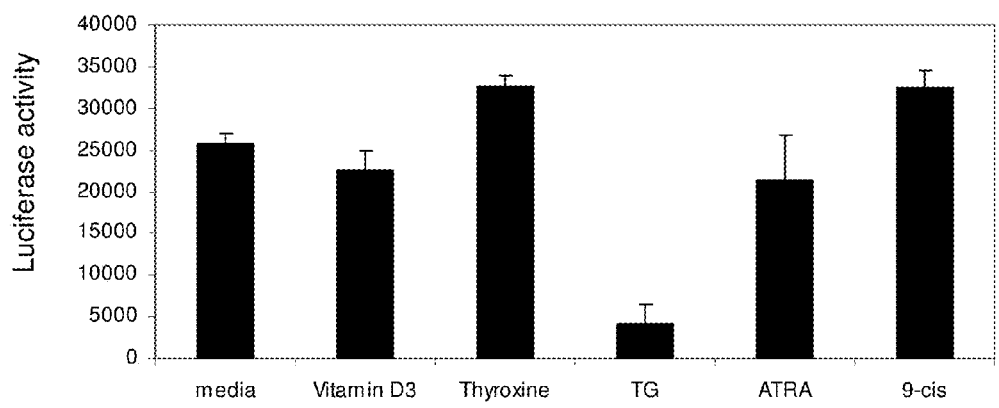
FIG. 55 shows the change in luciferase activity when various compounds are tested for the ability to modulate the function of NR2F6 using a system involving the GAL4 Upstream Activator Sequence (UAS) reporter vector that is activated by a chimerical protein containing the ligand binding domain of NR2F6 fused to a GAL4 DNA binding domain (DBD).
Figure 56:
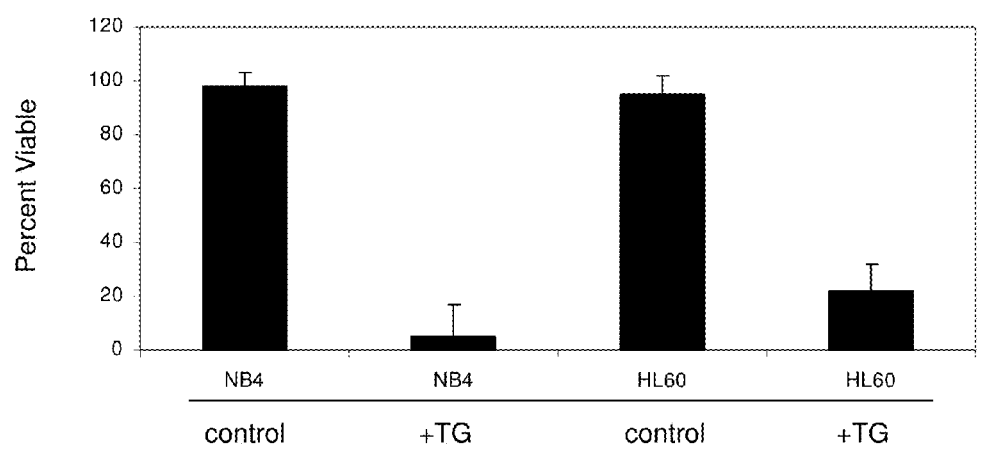
FIG. 56 shows the decrease in leukemia cell viability when one compound that was identified in FIG. 55. was tested for biological activity on human leukemia cells.
Figure 57:
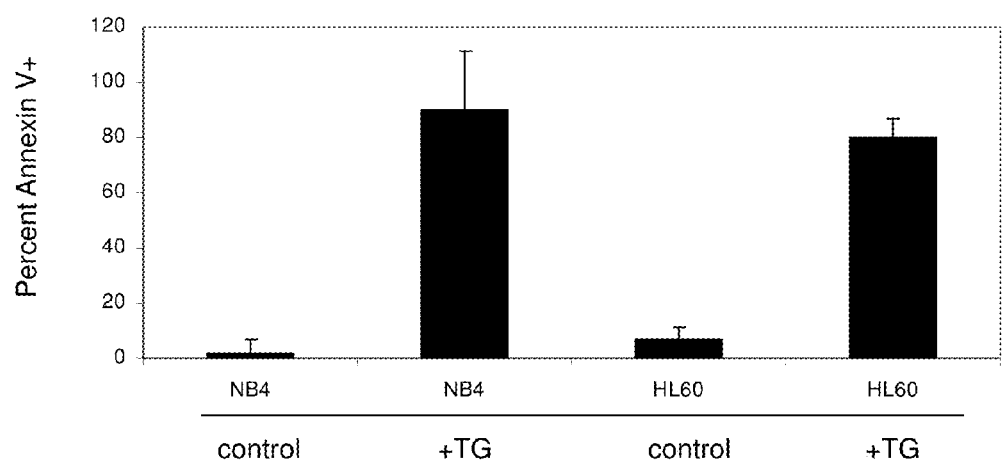
FIG. 57 shows that the decrease in leukemia cell viability when one compound that was identified in FIG. 55. was tested for biological activity on human leukemia cells is because of induction of apoptosis.

We then wished to devise a method of finding drugs that could have biological activity by identifying compounds that could modulate the function of NR2F6. In FIG. 55 the ligand binding domain (LBD) of NR2F6 was fused to a GAL4 DNA binding domain (DBD) on the pGL4 vector. This was then used to activate the luc2P luciferase reporter under the control of nine repeats of the GAL4 Upstream Activator Sequence (UAS). Here we have shown the proof of the principle that we have developed a screening tool to look for compounds that could modulate cell biological activity by modulating the transactivation ability of NR2F6. Using this screening tool we screened compounds and identified TG (troglitazone) as a compound that could exert biological activity on cancer cells and stem cells by modulating NR2F6 function. We then wanted to see if the compounds we identified could serve a biological function. In FIG. 56 We have shown the proof of the principle that a compound that we have identified in our screen of molecules that can modulate the transactivation ability of NR2F6 is able to exert biological activity on cancer cells and on stem cells. Here we show that 70 microM of troglitazone induces cell death in the human leukemia cell lines NB4 and HL60, showing that compounds found in a screen for molecules that modulate the transactivation ability of NR2F6 are able to effect not only stem cell parameters but also the viability of cancer cell populations. In FIG. 57 we show that that 70 microM of troglitazone induces apoptosis in the human leukemia cell lines NB4 and HL60 as detected by Annexin V staining, showing that compounds found in a screen for molecules that modulate the transactivation ability of NR2F6 are able to effect not only stem cell parameters but that when these processes are inhibited, you effect the viability of the cancer cell populations.

To summarize we have delineated a number of biological activities of the molecule NR2F6 and have devised a method that can be used to modulate these biological activities by screening for compounds that can alter the function of NR2F6. Here we show that by screening for compounds that alter the transcriptional activating or repressing activity of NR2F6 we can identify compounds that can act as targets for drug discovery.

Materials & Methods
Generation of Retroviruses
The 293GPG retroviral packaging cell line (a gift of Richard Mulligan, Harvard University) was grown in DMEM medium supplemented with 10% FBS, tetracycline (1 mg/mL), G418 (0.3 mg/mL) and puromycin (2 mg/mL). Human EAR-2 cDNA (a kind gift from John Ladias, Harvard University) or Mus EAR-2 cDNA (a kind gift from, Curt D. Sigmund, University of Iowa) was subcloned into the pcDNA3.1V5/HIS vector (Invitrogen). V5-tagged EAR-2 was subsequently subcloned into the murine myeloproliferative (MMP) retrovector such that it lay upstream of an IRES (internal ribosome entry sequence)-GFP cassette. VSV-G pseudotyped retroviral particles were generated by transient transfection of 293GPG cells as described (15).

Antibodies for Immunoblotting
Immunoblotting for human EAR-2 was performed using the PP-N2025-00 (Perseus Proteomics, Japan), or ab12982 (Abcam, Cambridge, Mass.) antibodies, while immunoblotting for mouse EAR-2 was performed using the LS-C40527 (LifeSpan Biosciences, Seattle, Wash.) antibody.

Real-Time PCR
RNA was isolated from 1×106 cells using Trizol reagent (Invitrogen) and first strand cDNA was synthesized using SuperScript reverse transcriptase (Qiagen) according to manufacturer's instructions. Real time PCR was performed according to manufacturer's instructions using SYBR Green Master Mix (Applied Biosystems, Foster City, Calif.) and analyzed using the delta-delta CT method (16).

Bone Marrow Transduction
Using the retroviral constructs described above, we forced expression of EAR-2 in primary murine BM cells and monitored the effects on differentiation using colony assays. Donor 12-week old C57BI/6 mice were given 5 fluorouracil, 150 g/g body mass, by intraperitoneal injection and humanely sacrificed ninety-six hours later. Bone marrow was collected from femurs and tibiae and cultured in Iscove's Modified Dulbecco's Medium (IMDM) supplemented with fetal bovine serum (5%), c-Kit ligand conditioned medium (3%), Flt-3 ligand (30 ng/mL), and TPO (30 ng/mL), conditions that minimize differentiation but initiate cycling of long-term repopulating cells. After 24 hours of culture, the cells were infected with MMP-GFP or MMP-EAR-2 retroviral supernatant at a multiplicity of infection (M01) of 100. Forty-eight hours after retroviral infection GFP-positive cells were collected by fluorescence activated cell sorting (FACS). We have shown that our transduction procedure preserves long-term multilineage potential by observing multilineage hematopoiesis at 12 months (data not shown).

Methylcellulose Colonies:
Bone marrow cells were collected from C57BI/6 mice 72 hour after intraperitoneal injection of 5-fluorouracil and were infected ex vivo either with retrovirus to overexpress EAR-2 or lentiviral particles to knock the gene down. GFP-positive cells were purified by fluorescence activated cell sorting (FACS) and cultured in methylcellulose medium containing hematopoietic growth factors that favored multilineage differentiation.

Following bone marrow transduction with MMP-GFP or MMP-EAR-2 GFP positive cells were collected by FACS and plated in methylcellulose medium (Methocult GF 3434, Stem Cell Technologies). Colony formation was evaluated after 10-14 days; clusters containing more than 30 cells were scored as a colony. Secondary colony formation was tested by harvesting entire primary colony cultures, washing the cells two times with PBS, and plating 10,000 cells in methylcellulose a second time. Secondary colonies were enumerated 12-14 days following secondary plating. We confirmed using fluorescent microscopy that all colonies continued to maintain transgene expression.

Hematopoietic Stem Cell Transplants
We generated bone marrow transplant recipients that received either chimeric EAR-2 or GFP transduced grafts or grafts that contained 100% bone marrow cells sorted for expression of GFP (and hence the transgene). To generate recipients transplanted with bone marrow grafts containing a mixture of transduced and wild-type cells 5FU-primed C57Bl/6 bone marrow cells were transduced with either MMP-GFP or MMP-EAR-2 as described above. Cells were then sorted by FACS. Grafts contained a mixture of transduced (GFP or EAR-2; $2.5 \times 10^4$ cells) and mock-transduced ($7.5 \times 10^4$ cells) donor cells. Primary chimeric transplants were performed as described. In some experiments chimeric transplant recipients were harvest at 4-6 weeks post transplant for analysis, and bone marrow was transplanted into another lethally irradiated mouse by tail-vein injection. Secondary recipients of chimeric bone marrow were harvested at either early time points 4-6 weeks or at late time points 12-16 weeks. To generate recipients transplanted with bone marrow grafts containing 100% transduced bone marrow cells 5FU-primed C57Bl/6 bone marrow cells were transduced with either MMP-GFP or MMP-EAR-2 as described above. Cells were then sorted by FACS and introduced into recipient mice by tail vein injection at a dosage of between $4 \times 10^4$ and $1 \times 10^5$ cells per recipient. All recipients of a given cohort received the same graft size. Recipient C57Bl/6 mice were irradiated in a Cs-137 small animal irradiator with 900 cGy, a dose we previously established to be lethal.

For the competitive transplant experiment primary grafts were prepared as described above except the transduced bone marrow was not sorted rather the percentage of marked cells was determined based on expression of GFP using flow cytometry.

Histological Sections and Cytospins

Immediately following sacrifice of animals tissues were rinsed in PBS and fixed for 24 hours in buffered formalin before being given to the Sunnybrook Research Institute Histology facility for paraffin embedding, slicing and staining with hematoxylin and eosin. Bone tissues were decalcified following fixation before further processing. Cytospins were prepared by centrifuging single celled suspensions onto glass slides using a Shandon cytocentrifuge. Cytospins were air dried, and fixed in methanol before staining with May-Grunwald and Giemsa stains. Cytospins were coverslipped following treatment with a toluene-based synthetic resin mounting medium.

Analysis of Hematopoietic Stem Cell Subsets:

For analysis of c-kit+, sca-1+, lineage−(KSL) cells, red blood cell depleted bone marrow cells were stained with a cocktail containing biotin CD3, biotin CD45R/B220 (RA3-6B2), biotin CD11b (M1/70), biotin erythroid marker (TER-119), biotin Ly-6G (RB6-8C5), c-kit APC, sca-1 PE-Cy7 and either CD34 PE or CD49b PE (all eBioscience) in the dark. Bone marrow was washed once and incubated with streptavidin PE-Cy5 for 20 minutes in the dark. Bone marrow was washed twice and analyzed using flow cytometry on a Becton Dickinson LSR II. All samples analyzed were gated based on FSC/SSC and GFP+ cells. The population of KSL cells is highly enriched for hematopoietic stem cell activity. This population was analyzed and further subdivided based on the expression of the CD34 and CD49b antigen.

Generation of shRNA

Oligonucleotides targeting human or mouse EAR-2 were synthesized (Sigma), annealed and cloned into the pSiren vector (Clontech), after which sequence was verified (The Centre for Applied Genomics, Toronto). Virus was prepared by transient transfection of plasmid in the 293GPG cell line as described above. Knockdown was confirmed by western blot for these vectors in cell lines and by qPCR in bone marrow cells (data not shown and (17)).

Statistical Analysis

Student's t-tests and one-way ANOVA followed by the Tukey Post-Hoc Test was used to assess statistical significance for normally distributed data. The Mann-Whitney U test or analysis of variance by Kruskal-Wallis test paired with Dunn's test was used for non-normally distributed data.

REFERENCES

1. Lawrence H J, Helgason C D, Sauvageau G, Fong S, Izon D J, Humphries R K, et al. Mice bearing a targeted interruption of the homeobox gene HOXA9 have defects in myeloid, erythroid, and lymphoid hematopoiesis. *Blood* 1997 March; 89(6): 1922-1930.
2. Alaminos M, Davalos V, Cheung N K, Gerald W L, Esteller M. Clustering of gene hypermethylation associated with clinical risk groups in neuroblastoma. *J Natl Cancer Inst* 2004 August; 96(16): 1208-1219.
3. Di Vinci A, Casciano I, Marasco E, Banelli B, Ravetti G L, Borzì L, et al. Quantitative methylation analysis of HOXA3, 7, 9, and 10 genes in glioma: association with tumor WHO grade and clinical outcome. *J Cancer Res Clin Oncol* 2012 January; 138(1): 35-47.
4. Enjuanes A, Fernàndez V, Hernandez L, Navarro A, Beà S, Pinyol M, et al. Identification of methylated genes associated with aggressive clinicopathological features in mantle cell lymphoma. *PLoS One* 2011; 6 (5): e19736.
5. Feng Q, Stern J E, Hawes S E, Lu H, Jiang M, Kiviat N B. DNA methylation changes in normal liver tissues and hepatocellular carcinoma with different viral infection. *Exp Mol Pathol* 2010 April; 88(2): 287-292.
6. Guerrero-Preston R, Soudry E, Acero J, Orera M, Moreno-Lopez L, Macìa-Colòn G, et al. NID2 and HOXA9 promoter hypermethylation as biomarkers for prevention and early detection in oral cavity squamous cell carcinoma tissues and saliva. *Cancer Prev Res (Phila)* 2011 July; 4(7): 1061-1072.
7. Hwang S H, Kim K U, Kim J E, Kim H H, Lee M K, Lee C H, et al. Detection of HOXA9 gene methylation in tumor tissues and induced sputum samples from primary lung cancer patients. *Clin Chem Lab Med* 2011 April; 49(4): 699-704.
8. Montavon C, Gloss B S, Warton K, Barton C A, Statham A L, Scurry J P, et al. Prognostic and diagnostic significance of DNA methylation patterns in high grade serous ovarian cancer. *Gynecol Oncol* 2012 March; 124(3): 582-588.
9. Nelson H H, Marsitg C J, Christensen B C, Houseman E A, Kontic M, Wiemels J L, et al. Key epigenetic changes associated with lung cancer development: Results from dense methylation array profiling. *Epigenetics* 2012 June; 7 (6).
10. Rauch T, Wang Z, Zhang X, Zhong X, Wu X, Lau S K, et al. Homeobox gene methylation in lung cancer studied by genome-wide analysis with a microarray-based methylated CpG island recovery assay. *Proc Natl Acad Sci USA* 2007 March; 104(13): 5527-5532.
11. Reinert T, Modin C, Castano F M, Lamy P, Wojdacz T K, Hansen L L, et al. Comprehensive genome methylation analysis in bladder cancer: identification and validation of novel methylated genes and application of these as urinary tumor markers. *Clin Cancer Res* 2011 September; 17(17): 5582-5592.
12. Shin S H, Kim B H, Jang J J, Suh K S, Kang G H. Identification of novel methylation markers in hepatocellular carcinoma using a methylation array. *J Korean Med Sci* 2010 August; 25(8): 1152-1159.

13. Son J W, Jeong K J, Jean W S, Park S Y, Jheon S, Cho H M, et al. Genome-wide combination profiling of DNA copy number and methylation for deciphering biomarkers in non-small cell lung cancer patients. *Cancer Lett* 2011 December; 311(1): 29-37.
14. Galan-Caridad J M, Harel S, Arenzana T L, Hou Z E, Doetsch F K, Mirny L A, et al. Zfx controls the self-renewal of embryonic and hematopoietic stem cells. *Cell* 2007 April; 129(2): 345-357.
15. Ichim C V, Wells R A. Generation of high-titer viral preparations by concentration using successive rounds of ultracentrifugation. *J Transl Med* 2011; 9: 137.
16. Livak K J, Schmittgen T D. Analysis of relative gene expression data using real-time quantitative PCR and the 2(-Delta Delta C(T)) Method. *Methods* 2001 December; 25(4): 402-408.
17. Ichim C V, Atkins H L, Iscove N N, Wells R A. Identification of a role for the nuclear receptor EAR-2 in the maintenance of clonogenic status within the leukemia cell hierarchy. *Leukemia* 2011 November; 25(11): 1687-1696.

One embodiment is the ligand binding domain of the protein with amino acid sequence of SEQ ID NO: 2 is fused to the Gal4 DNA binding domain. Another embodiment is the screening for compounds for identification of lead compounds for drug development. Yet another embodiment is the screening for compounds for drug development against cancer. Another embodiment is the screening for compounds to be used for drug development to treat disorders of t-cell over expression. Therefore, screening for compounds with biological activity can identify compounds that can inhibit T-cell development in order to promote graft tolerance following organ transplantation in vivo; prevent graft versus host disease following bone marrow transplantation in vivo; treat autoimmune disease including but not limited to rheumatoid arthritis, type I diabetes, systemic lupus erythematosus, multiple sclerosis, autoimmune lymphoproliferative syndrome, Crohn's disease Behcet's disease, psoriasis, psoriatic arthritis, scleroderma, and ankylosing spondylitis; treat allergy in vivo; prepare t-cell depleted grafts for allogenic bone marrow transplantation involving in vitro stem and progenitor cell culture. While another embodiment is screening for compounds with biological activity that can stimulate T-cell development in order to promote the differentiation of stem or progenitor cells into T-cells in vivo for the purposes of strengthening one's immune system to fight cancer, infection, parasites or to promote general health; promote the differentiation of stem or progenitor cells into T-cells in vivo for the treatment of immune deficiencies such as HIV and AIDS, genetic immune deficiency disorders, etc; promote the differentiation of stem or progenitor cells toward the T cell lineage in the ex vivo development of cancer vaccines, immunotherapy or cell therapy; promote the differentiation of stem or progenitor cells into T-cells in vivo following myeloablative regimens such as chemotherapy; promote the differentiation of stem or progenitor cells into T-cells in vitro for adoptive transfer into patients that have received myeloablative regimens such as chemotherapy; promote the differentiation of stem or progenitor cells into T-cells in vitro for adoptive transfer into patients that have immune deficiencies such as HIV and AIDS, genetic immune deficiency disorders, etc. Furthermore, in yet another embodiment an NR2F6 stimulatory compound identified using this screen could be used synergistically with cyclosporine A in the context of organ transplantation and transplantation of xenogenic organs; methotrexate for the treatment of autoimmunity.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Nucleotide and Amino Acid sequence of NR2F6 mRNA sequence of human NR2F6 Genbank ID BC063018:

```
cgagaggggt gcccggaggg aagagcgcgg tgggggcgcc ccggccccgc tgccctgggg
ctatggccat ggtgaccggc ggctgggcg gccccggcgg cgacacgaac ggcgtggaca
aggcgggcgg ctacccgcgc gcggccgagg acgactcggc ctcgcccccc ggtgccgcca
gcgacgccga gccgggcgac gaggagcggc cggggctgca ggtggactgc gtggtgtgcg
gggacaagtc gagcggcaag cattacggtg tcttcacctg cgagggctgc aagagctttt
tcaagcgaag catccgccgc aacctcagct acacctgccg gtccaaccgt gactgccaga
tcgaccagca ccaccggaat cagtgccogt actgccgtct caagaagtgc ttccgggtgg
gcatgaggaa ggaggcggtg cagcgcggcc gcatcccgca ctcgctgcct ggtgccgtgg
ccgcctcctc gggcagcccc ccgggctcgg cgctggcggc agtggcgagc ggcggagacc
tcttcccggg gcagccggtg tccgaactga tcgcgcagct gctgcgcgct gagccctacc
ctgcggcggc cggacgcttc ggcgcagggg gcggcgcggc gggcgcagtg ctgggcatcg
acaacgtgtg cgagctggcg gcgcggctgc tcttcagcac cgtggagtgg gcgcgccacg
cgcccttctt ccccgagctg ccggtggccg accaggtggc gctgctgcgc ctgagctgga
gcgagctctt cgtgctgaac gcggcgcagg cggcgctgcc cctgcacacg cgcccgctac
tggccgccgc cggcctccac gccgcgccta tggccgccga gcgcgccgtg gctttcatgg
accaggtgcg cgccttccag gagcaggtgg acaagctggg ccgcctgcag gtcgactcgg
ccgagtatgg ctgcctcaag gccatccgcc tcttcacgcc cgacgcctgt ggcctctcag
acccggccca cgttgagagc ctgcaggaga aggcgccaggt ggccctcacc gagtatgtgc
gggcgcagta cccgtccagc ccccagcgct tcggggcgct gctgctgcgg ctccccgccc
tgcgcgcggt ccctgcctcc ctcatctccc agctgttctt catgcgcctg gtggggaaga
cgccattga gacactgatc agagacatgc tgctgtcggg gagtaccttc aactggccct
acggctcggg ccagtgacca tgacggggcc acgtgtgctg tggccagggcc tgcagacaga
cctcaaggga cagggaatgc tgaggcctcg aggggccctcc cggggcccag gactctggct
tctctcctca gacttctatt ttttaaagac tgtgaaatgt ttgtctttc tgtttttaa
atgatcatga aaccaaaaag agactgatca tccaggcctc agcctcatcc tccccaggac
ccctgtccag gatggagggt ccaatcctag gacagccttg ttcctcagca ccctagcat
gaacttgtgg gatggtgggg ttggcttccc tggcatgatg gacaaaggcc tggcgtcggc
```

TABLE 1-continued

Nucleotide and Amino Acid sequence of NR2F6

```
cagaggggct gctccagtgg gcaggggtag ctagcgtgtg ccaggcagat cctctggaca
cgtaacctat gtcagacact acatgatgac tcaaggccaa taataaagac atttcctacc
tgcacaaaaa aaaaaaaaaa aaaaaaaaaa aaaaaaaaaa aaa
(SEQ ID NO: 1)
``` mRNA sequence of mouse NR2F6 Genbank ID BC008138.1:

```
cggacgcgtg ggcgggggcg cccgcgcgcg ctcggatggt gagccactaa gttggcctgg
gcggcggggc cgggccatgg ccccgcgac gctaccgggt cccaggact ccggaccacg
ggacctgggc gccccagact cgcgcctcta gcgcgccccc gtcgaccgcg ggcacgcgtg
ggaaagttgg cctggaaccg gcccgaccag ttcctgcctg gcgcgccggac cggccgcagg
aagttgccgc aaaactttt tcagggggt gtgcgaccgg agcccccga gagcgcgggc
tgcatgcgcc cggggtagcc gggtccctct cgggtcgcca ggcgtgccca gaggggacgg
actcgtcccg gggcgtcccg gccccgctgt ctccgggggct atggccatgg tgaccggtgg
ctggggcgac cccggaggcg acacgaacgg cgtggacaag gctggtggga gctacccacg
cgcgaccgag gacgattcgg cgtcacctcc cggggcgacc agcgacgcgg agccgggcga
cgaggagcgt ccggggttgc aggtggactg cgtggtgtgc ggggacaagt ccagtggaaa
gcattacggc gtgttcacct gcgagggctg caagagtttc ttcaagcgca gcatccgccg
caatctcagc tacacctgcc ggtccaaccg tgactgtcaa attgatcagc accaccggaa
ccagtgtcag tactgtcggc tcaagaagtg cttccgggtg ggcatgcgca aggaggccgt
gcagcgaggc cgcatcccgc atgcgctccc cggtccagcg gcctgcagtc ccccgggcgc
gacgggcgtc gaacctttca cggggccgcc agtgtccgag ctgattgcgc agctgctgcg
tgctgagccc taccccgcgg ccggacgctt tggtggcggc ggcgctgtac tgggcatcga
caacgtgtgc gagttggcgg cacgcctgct gttcagcacg gtcgagtggg ccgccacgc
gcccttcttc cccgagctgc cggccgccga ccaggtggcg ctgctgcggc tcagctggag
tgagctcttc gtgctgaacg cggcgcaggc ggcgctgccg ctgcatacgg caccgctgct
ggccgccgcg gggttcatg ccgcgcccat ggcagccgag cgggccgtgg ccttcatgga
ccaggtgcgt gccttccagg agcaggtgga caagctgggc cgcctgcagg tggatgctgc
ggagtacggc tgcctcaagg ccatcgcgct cttcacgcct gatgcctgtg gcctttctga
cccagcccat gtgagagcc tgcaggagaa ggcacaggtg gccctcaccg agtatgtgcg
tgcccagtac ccatcgcagc cccagcgctt gggcgtctg ctgctgcggc tgccagccct
gcgtgctgtg cccgcatccc tcatctccca gctcttcttc atgcgcctgg tgggcaagac
acccatcgag accctcatcc gggacatgct tctgtcaggg agcaccttta actgcccta
tggctcgggc tagtgatagt caccttccag gacacacatg gaaactgggg ccttgtgggg
accctgggga tcagggcccc agcttctctt ttgagactga tttcttttt taaagactgt
gaaatgtttg ttttgttta tttttaaat aatcatgaaa ccaaaagat ttggatctcc
caggcctag ccttgtcctg gcagaccttc aacagtctgg agccagcatg ctggtgcctc
tggtgtcatg ggtatctgga aaggccactg cagctaggca ggagtactat gggccaggag
gatccctgg atacatggtc cacggagggc accatgggat gatgaaaacc tggccaataa
taaaggtatt cccttaaaaa aaaaaaaaaa aaaaaaaa
(SEQ ID NO: 4)
```

Protein sequence of human NR2F6

```
mamvtggwgg pggdtngvdk aggypraaed dsasppgaas daepgdeerp glqvdcvvcg
dkssgkhygv ftcegcksff krsirrnlsy tcrsnrdcqi dqhhrnqcqy crlkkcfrvg
mrkeavqrgr iphslpgava assgsppgsa laavasggdl fpgqpvseli aqllraepyp
aaagrfgagg gaagavlgid nvcelaarll fstvewarha pffpelpvad qvallrlsws
elfvinaaqa alplhtapll aaaglhaapm aaeravafmd qvrafqeqvd klgrlqvdsa
eygclkaial ftpdacglsd pahveslqek aqvalteyvr agypsqpqrf grlllrlpal
ravpaslisq lffmrlvgkt pietlirdml lsgstfnwpy gsgq
(SEQ ID NO: 2)
```

Protein sequence of mouse NR2F6

```
mamvtggwgd pggdtngvdk aggsyprate ddsasppgat sdaepgdeer pglqvdcvvc
gdkssgkhyg vftcegcksf fkrsirrnls ytcrsnrdcq idqhhrnqcq ycrlkkcfrv
gmrkeavqrg riphalpgpa acsppgatgv epftgppvse liaqllraep ypaagrfggg
gavlgidnvc elaarllfst vewarhapff pelpaadqva llrlswself vlnaaqaalp
lhtapllaaa glhaapmaae ravafmdqvr afqeqvdklg rlqvdaaeyg clkaialftp
dacglsdpah veslqekaqv alteyvraqy psqpqrfgrl llrlpalrav paslisqlff
mrlvgktpie tlirdmllsg stfnwpygsg
(SEQ ID NO: 3)
```

Mus shNR2F6 sequence

```
GATCCGCATTACGGCGTGTTCACCTTCAAGAGAGGTGAACACGCCGTAATGCTTTTTTCT
AGAG
(SEQ ID NO: 5)
```

Human shNR2F6 sequence

```
GATCCGCATTACGGTGTCTTCACCTTCAAGAGAGGTGAAGACACCGTAATGCTTTTTTCTAGAG
(SEQ ID NO: 6)
```

The invention claimed is:

1. A method for identifying compounds that can modulate the function of NR2F6 in mammalian cells comprising the steps of:
   (i) selecting a cancer (a) cell line or (b) cell-free lysate to use;
   (ii) expressing in the cancer cell-line or cell-free lysate proteins encoded by one or more recombinant DNA vectors that comprise a reporter assay system, having a portion of the gene with SEQ ID NO:1 that has been predetermined to control the transcriptional activity of the gene NR2F6 and that encodes for expression of an amino acid sequence of at least 75% sequence identity to a portion of the amino acid sequence of SEQ ID NO: 2;
(iii) contacting the cancer cell-line or or cell-free lysate with a candidate compound;
(iv) measuring the ability of the candidate compound to inhibit or stimulate said reporter assay system; and
(v) comparing the measurement of the ability of the candidate compound to inhibit or stimulate said reporter assay system with a suitable control so as to determine whether said inhibition or stimulation of said reporter assay system is indicative of a compound for modulating the function of NR2F6 in a mammal.

2. The method of claim 1 wherein HeLa cells are used for the cancer (a) cell-line or (b) cell-free lysate.

3. The method of claim 1, wherein the method is a high-throughput screening.

4. The method of claim 1, wherein the portion of the nucleotide that encodes for expression of an amino acid sequence of at least 75% sequence identity of the amino acid sequence of SEQ ID NO: 2 is the ligand binding domain of NR2F6.

5. The method of claim 1, wherein the reporter assay system measures the ability of the candidate compound to cause a conformational change in the ligand binding domain of NR2F6.

6. The method of claim 1, wherein the reporter assay system measures the compound's ability to modulate the ability of NR2F6 to repress or activate transcription.

7. The method of claim 1 wherein a cell based assay is used in which the host cell contains an expression vector, said expression vector comprising a polynucleotide, said polynucleotide comprising a nucleotide sequence encoding a polypeptide comprising the amino acid sequence of SEQ ID NO: 2.

8. The method of claim 1 wherein a cell based assay using cultured mammalian cells transfected with a vector encoding for a protein with amino acid sequence of SEQ ID NO: 2 and a reporter construct, where the cells are treated with candidate compounds and assessed for the activity of the reporter construct.

9. The method of claim 1 wherein the reporter assay system consists of at least one or more DNA vectors, one of which contains a DNA binding site positioned adjacent to an expressible reporter element; another contains a chimeric transactivatable vector comprising nucleotides that encode for a portion of the NR2F6 gene and a DNA binding domain that specifically binds to the DNA binding site.

10. The method of claim 9 wherein the DNA binding site further comprises a GAL4 binding element.

11. The method of claim 9 wherein the expressible reporter element is luciferase.

12. A method of claim 9 wherein the DNA binding domain that specifically binds to the DNA binding site consists of multiple Gal4 Upstream Activator Sequences.

* * * * *

SEQUENCE LISTING

<160> NUMBER OF SEQ ID NOS: 10

<210> SEQ ID NO 1
<211> LENGTH: 1783
<212> TYPE: DNA
<213> ORGANISM: Homo sapiens

<400> SEQUENCE: 1

| | | | | | |
|---|---|---|---|---|---|
| cgagagggt | gcccggaggg | aagagcgcgg | tggggggcgcc | ccggcccccgc | tgccctgggg | 60 |
| ctatggccat | ggtgaccggc | ggctggggcg | gccccggcgg | cgacacgaac | ggcgtggaca | 120 |
| aggcgggcgg | ctacccgcgc | gcggccgagg | acgactcggc | ctcgcccccc | ggtgccgcca | 180 |
| gcgacgccga | gccggggcgac | gaggagcggc | cggggctgca | ggtggactgc | gtggtgtgcg | 240 |
| gggacaagtc | gagcggcaag | cattacggtg | tcttcacctg | cgagggctgc | aagagcttt | 300 |
| tcaagcgaag | catccgccgc | aacctcagct | acacctgccg | gtccaaccgt | gactgccaga | 360 |
| tcgaccagca | ccaccggaat | cagtgccagt | actgccgtct | caagaagtgc | ttccgggtgg | 420 |
| gcatgaggaa | ggaggcggtg | cagcgcggcc | gcatcccgca | ctcgctgcct | ggtgccgtgg | 480 |
| ccgcctcctc | gggcagcccc | ccgggctcgg | cgctggcggc | agtggcgagc | ggcggagacc | 540 |
| tcttcccggg | gcagccggtg | tccgaactga | tcgcgcagct | gctgcgcgct | gagccctacc | 600 |
| ctgcggcggc | cggacgcttc | ggcgcagggg | gcggcgcggc | gggcgcagtg | ctgggcatcg | 660 |
| acaacgtgtg | cgagctggcg | gcgcggctgc | tcttcagcac | cgtggagtgg | gcgcgccacg | 720 |
| cgccttctt | ccccgagctg | ccggtggccg | accaggtggc | gctgctgcgc | ctgagctgga | 780 |
| gcgagctctt | cgtgctgaac | gcggcgcagg | cggcgctgcc | cctgcacacg | gcgccgctac | 840 |
| tggccgccgc | cggcctccac | gccgcgccta | tggccgccga | gcgcgccgtg | gctttcatgg | 900 |
| accaggtgcg | cgccttccag | gagcaggtgg | acaagctggg | ccgcctgcag | gtcgactcgg | 960 |
| ccgagtatgg | ctgcctcaag | gccatcgcgc | tcttcacgcc | cgacgcctgt | ggcctctcag | 1020 |
| acccggccca | cgttgagagc | ctgcaggaga | aggcgcaggt | ggccctcacc | gagtatgtgc | 1080 |
| gggcgcagta | cccgtcccag | ccccagcgct | cgggcgcct | gctgctgcgg | ctccccgccc | 1140 |
| tgcgcgcggt | ccctgcctcc | ctcatctccc | agctgttctt | catgcgcctg | gtggggaaga | 1200 |
| cgcccattga | gacactgatc | agagacatgc | tgctgtcggg | gagtaccttc | aactggccct | 1260 |
| acggctcggg | ccagtgacca | tgacggggcc | acgtgtgctg | tggccaggcc | tgcagacaga | 1320 |
| cctcaaggga | cagggaatgc | tgaggcctcg | aggggcctcc | cggggcccag | gactctggct | 1380 |
| tctctcctca | gacttctatt | ttttaaagac | tgtgaaatgt | ttgtcttttc | tgttttttaa | 1440 |
| atgatcatga | aaccaaaaag | agactgatca | tccaggcctc | agcctcatcc | tccccaggac | 1500 |
| ccctgtccag | gatggagggt | ccaatcctag | gacagccttg | ttcctcagca | ccctagcat | 1560 |
| gaacttgtgg | gatggtgggg | ttggcttccc | tggcatgatg | gacaaaggcc | tggcgtcggc | 1620 |
| cagagggct | gctccagtgg | gcaggggtag | ctagcgtgtg | ccaggcagat | cctctggaca | 1680 |
| cgtaacctat | gtcagacact | acatgatgac | tcaaggccaa | taataaagac | atttcctacc | 1740 |
| tgcacaaaaa | aaaaaaaaaa | aaaaaaaaaa | aaaaaaaaaa | aaa | | 1783 |

<210> SEQ ID NO 2
<211> LENGTH: 404
<212> TYPE: PRT
<213> ORGANISM: Homo sapiens

<400> SEQUENCE: 2

Met Ala Met Val Thr Gly Gly Trp Gly Gly Pro Gly Gly Asp Thr Asn

```
1               5                   10                  15
Gly Val Asp Lys Ala Gly Tyr Pro Arg Ala Glu Asp Asp Ser
            20                  25                  30
Ala Ser Pro Pro Gly Ala Ala Ser Asp Ala Glu Pro Gly Asp Glu Glu
            35                  40                  45
Arg Pro Gly Leu Gln Val Asp Cys Val Val Cys Gly Asp Lys Ser Ser
50                      55                  60
Gly Lys His Tyr Gly Val Phe Thr Cys Glu Gly Cys Lys Ser Phe Phe
65                      70                  75                  80
Lys Arg Ser Ile Arg Arg Asn Leu Ser Tyr Thr Cys Arg Ser Asn Arg
                85                  90                  95
Asp Cys Gln Ile Asp Gln His His Arg Asn Gln Cys Gln Tyr Cys Arg
                100                 105                 110
Leu Lys Lys Cys Phe Arg Val Gly Met Arg Lys Glu Ala Val Gln Arg
                115                 120                 125
Gly Arg Ile Pro His Ser Leu Pro Gly Ala Val Ala Ala Ser Ser Gly
                130                 135                 140
Ser Pro Pro Gly Ser Ala Leu Ala Ala Val Ala Ser Gly Gly Asp Leu
145                 150                 155                 160
Phe Pro Gly Gln Pro Val Ser Glu Leu Ile Ala Gln Leu Leu Arg Ala
                165                 170                 175
Glu Pro Tyr Pro Ala Ala Ala Gly Arg Phe Gly Ala Gly Gly Ala
                180                 185                 190
Ala Gly Ala Val Leu Gly Ile Asp Asn Val Cys Glu Leu Ala Ala Arg
                195                 200                 205
Leu Leu Phe Ser Thr Val Glu Trp Ala Arg His Ala Pro Phe Phe Pro
            210                 215                 220
Glu Leu Pro Val Ala Asp Gln Val Ala Leu Leu Arg Leu Ser Trp Ser
225                 230                 235                 240
Glu Leu Phe Val Leu Asn Ala Ala Gln Ala Ala Leu Pro Leu His Thr
                245                 250                 255
Ala Pro Leu Leu Ala Ala Ala Gly Leu His Ala Ala Pro Met Ala Ala
                260                 265                 270
Glu Arg Ala Val Ala Phe Met Asp Gln Val Arg Ala Phe Gln Glu Gln
            275                 280                 285
Val Asp Lys Leu Gly Arg Leu Gln Val Asp Ser Ala Glu Tyr Gly Cys
            290                 295                 300
Leu Lys Ala Ile Ala Leu Phe Thr Pro Asp Ala Cys Gly Leu Ser Asp
305                 310                 315                 320
Pro Ala His Val Glu Ser Leu Gln Glu Lys Ala Gln Val Ala Leu Thr
                325                 330                 335
Glu Tyr Val Arg Ala Gln Tyr Pro Ser Gln Pro Gln Arg Phe Gly Arg
                340                 345                 350
Leu Leu Leu Arg Leu Pro Ala Leu Arg Ala Val Pro Ala Ser Leu Ile
                355                 360                 365
Ser Gln Leu Phe Phe Met Arg Leu Val Gly Lys Thr Pro Ile Glu Thr
                370                 375                 380
Leu Ile Arg Asp Met Leu Leu Ser Gly Ser Thr Phe Asn Trp Pro Tyr
385                 390                 395                 400
Gly Ser Gly Gln

<210> SEQ ID NO 3
<211> LENGTH: 390
```

<212> TYPE: PRT
<213> ORGANISM: Mus musculus

<400> SEQUENCE: 3

```
Met Ala Met Val Thr Gly Gly Trp Gly Asp Pro Gly Gly Asp Thr Asn
1               5                   10                  15

Gly Val Asp Lys Ala Gly Gly Ser Tyr Pro Arg Ala Thr Glu Asp Asp
            20                  25                  30

Ser Ala Ser Pro Pro Gly Ala Thr Ser Asp Ala Glu Pro Gly Asp Glu
        35                  40                  45

Glu Arg Pro Gly Leu Gln Val Asp Cys Val Val Cys Gly Asp Lys Ser
    50                  55                  60

Ser Gly Lys His Tyr Gly Val Phe Thr Cys Glu Gly Cys Lys Ser Phe
65                  70                  75                  80

Phe Lys Arg Ser Ile Arg Arg Asn Leu Ser Tyr Thr Cys Arg Ser Asn
                85                  90                  95

Arg Asp Cys Gln Ile Asp Gln His His Arg Asn Gln Cys Gln Tyr Cys
            100                 105                 110

Arg Leu Lys Lys Cys Phe Arg Val Gly Met Arg Lys Glu Ala Val Gln
        115                 120                 125

Arg Gly Arg Ile Pro His Ala Leu Pro Gly Pro Ala Ala Cys Ser Pro
    130                 135                 140

Pro Gly Ala Thr Gly Val Glu Pro Phe Thr Gly Pro Pro Val Ser Glu
145                 150                 155                 160

Leu Ile Ala Gln Leu Leu Arg Ala Glu Pro Tyr Pro Ala Ala Gly Arg
                165                 170                 175

Phe Gly Gly Gly Ala Val Leu Gly Ile Asp Asn Val Cys Glu Leu
            180                 185                 190

Ala Ala Arg Leu Leu Phe Ser Thr Val Glu Trp Ala Arg His Ala Pro
        195                 200                 205

Phe Phe Pro Glu Leu Pro Ala Ala Asp Gln Val Ala Leu Leu Arg Leu
    210                 215                 220

Ser Trp Ser Glu Leu Phe Val Leu Asn Ala Ala Gln Ala Ala Leu Pro
225                 230                 235                 240

Leu His Thr Ala Pro Leu Leu Ala Ala Ala Gly Leu His Ala Ala Pro
                245                 250                 255

Met Ala Ala Glu Arg Ala Val Ala Phe Met Asp Gln Val Arg Ala Phe
            260                 265                 270

Gln Glu Gln Val Asp Lys Leu Gly Arg Leu Gln Val Asp Ala Ala Glu
        275                 280                 285

Tyr Gly Cys Leu Lys Ala Ile Ala Leu Phe Thr Pro Asp Ala Cys Gly
    290                 295                 300

Leu Ser Asp Pro Ala His Val Glu Ser Leu Gln Glu Lys Ala Gln Val
305                 310                 315                 320

Ala Leu Thr Glu Tyr Val Arg Ala Gln Tyr Pro Ser Gln Pro Gln Arg
                325                 330                 335

Phe Gly Arg Leu Leu Leu Arg Leu Pro Ala Leu Arg Ala Val Pro Ala
            340                 345                 350

Ser Leu Ile Ser Gln Leu Phe Phe Met Arg Leu Val Gly Lys Thr Pro
        355                 360                 365

Ile Glu Thr Leu Ile Arg Asp Met Leu Leu Ser Gly Ser Thr Phe Asn
    370                 375                 380

Trp Pro Tyr Gly Ser Gly
385                 390
```

<210> SEQ ID NO 4
<211> LENGTH: 1959
<212> TYPE: DNA
<213> ORGANISM: Mus musculus

<400> SEQUENCE: 4

```
cggacgcgtg ggcggggcg cccgcgcgcg ctcggatggt gagccactaa gttggcctgg        60
gcggcggggc cgggccatgg cccccgcgac gctaccgggt ccccaggact ccggaccacg       120
ggacctgggc gccccagact cgcgcctcta gcgcgccccc gtcgaccgcg gcacgcgtg        180
ggaaagttgg cctggaaccg gcccgaccag ttcctgcctg gcgcgcggac cggccgcagg       240
aagttgccgc aaaactttt tcagggggt gtgcgaccgg agcccccga gagcgcgggc         300
tgcatgcgcc cggggtagcc gggtccctct cgggtcgcca ggcgtgccca gaggggacgg       360
actcgtcccg gggcgtcccg gccccgctgt ctccggggct atggccatgg tgaccggtgg       420
ctggggcgac cccggaggcg acacgaacgg cgtggacaag gctggtggga gctacccacg       480
cgcgaccgag gacgattcgg cgtcacctcc cggggcgacc agcgacgcgg agccgggcga       540
cgaggagcgt ccggggttgc aggtggactg cgtggtgtgc ggggacaagt ccagtggaaa       600
gcattacggc gtgttcacct gcgagggctg caagagtttc ttcaagcgca gcatccgccg       660
caatctcagc tacacctgcc ggtccaaccg tgactgtcag attgatcagc accaccggaa       720
ccagtgtcag tactgtcggc tcaagaagtg cttccgggtg ggcatgcgca aggaggccgt       780
gcagcgaggc gcatcccgc atgcgctccc cggtccagcg gcctgcagtc ccccgggcgc       840
gacgggcgtc gaacctttca cggggccgcc agtgtccgag ctgattgcgc agctgctgcg       900
tgctgagccc tacccccgcg gccggacgct tggtggcggc ggcgctgtac tgggcatcga       960
caacgtgtgc gagttggcgg cacgcctgct gttcagcacg gtcgagtggg cccgccacgc      1020
gcccttcttc cccgagctgc cggccgccga ccaggtggcg ctgctgcggc tcagctggag      1080
tgagctcttc gtgctgaacg cggcgcaggc ggcgctgccg ctgcatacgg caccgctgct      1140
ggccgccgcg gggttgcatg ccgcgcccat ggcagccgag cgggccgtgg ccttcatgga      1200
ccaggtgcgt gccttccagg agcaggtgga caagctgggc cgcctgcagg tggatgctgc      1260
ggagtacggc tgcctcaagg ccatcgcgct cttcacgcct gatgcctgtg gccttcctga      1320
cccagcccat gtgagagcc tgcaggagaa ggcacaggtg ccctcaccg agtatgtgcg       1380
tgcccagtac ccatcgcagc cccagcgctt tgggcgtctg ctgctgcggc tgccagccct      1440
gcgtgctgtg cccgcatccc tcatctccca gctcttcttc atgcgcctgg tgggcaagac      1500
acccatcgag accctcatcc gggacatgct tctgtcaggg agcaccttta actggcccta      1560
tggctcgggc tagtgatagt caccttccag gacacacatg gaaactgggg ccttgtgggg      1620
accctgggga tcagggcccc agcttctctt ttgagactga tttctttttt taaagactgt      1680
gaaatgtttg ttttgtttta tttttaaat aatcatgaaa ccaaaaagat ttggatctcc      1740
caggccctag ccttgtcctg gcagaccttc aacagtctgg agccagcatg ctggtgcctc      1800
tggtgtcatg ggtatctgga aaggccactg cagctaggca ggagtactat gggccaggag      1860
gatcccctgg atacatggtc cacggagggc accatgggat gatgaaaacc tggccaataa      1920
taaaggtatt cccttaaaaa aaaaaaaaa aaaaaaaa                               1959
```

<210> SEQ ID NO 5
<211> LENGTH: 64
<212> TYPE: DNA

```
<213> ORGANISM: Artificial Sequence
<220> FEATURE:
<223> OTHER INFORMATION: Mus shNR2F6 sequence

<400> SEQUENCE: 5
gatccgcatt acggcgtgtt caccttcaag agaggtgaac acgccgtaat gctttttcct      60
agag                                                                   64

<210> SEQ ID NO 6
<211> LENGTH: 64
<212> TYPE: DNA
<213> ORGANISM: Artificial Sequence
<220> FEATURE:
<223> OTHER INFORMATION: Human shNR2F6 sequence

<400> SEQUENCE: 6
gatccgcatt acggtgtctt caccttcaag agaggtgaag acaccgtaat gctttttcct      60
agag                                                                   64

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tctcccagct gttcttcatg c                                                21

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ccagttgaag gtactccccg                                                  20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ggcctccaag gagtaagacc                                                  20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
aggggtctac atggcaactg                                                  20
```